(12) United States Patent
Jin et al.

(10) Patent No.: US 10,260,070 B2
(45) Date of Patent: *Apr. 16, 2019

(54) APTAMER FOR NGF AND USE THEREOF

(75) Inventors: Ling Jin, Tokyo (JP); Shin Miyakawa, Tokyo (JP); Masatoshi Fujiwara, Tokyo (JP); Yoshikazu Nakamura, Tokyo (JP); Hisanao Hiramatsu, Osaka (JP)

(73) Assignees: RIBOMIC INC., Tokyo (JP); FUJIMOTO PHARMACEUTICAL CORPORATION, Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/120,650

(22) PCT Filed: Sep. 18, 2009

(86) PCT No.: PCT/JP2009/066457
§ 371 (c)(1),
(2), (4) Date: Jun. 15, 2011

(87) PCT Pub. No.: WO2010/035725
PCT Pub. Date: Apr. 1, 2010

(65) Prior Publication Data
US 2011/0251266 A1    Oct. 13, 2011

(30) Foreign Application Priority Data
Sep. 24, 2008    (JP) ................. 2008-244982

(51) Int. Cl.
*C12N 15/11* (2006.01)
*C12N 15/115* (2010.01)
*C07K 1/22* (2006.01)

(52) U.S. Cl.
CPC ............. *C12N 15/115* (2013.01); *C07K 1/22* (2013.01); *C12N 2310/16* (2013.01)

(58) Field of Classification Search
None
See application file for complete search history.

(56) References Cited

U.S. PATENT DOCUMENTS

| | | | |
|---|---|---|---|
| 5,660,985 A | 8/1997 | Pieken et al. | |
| 5,958,691 A * | 9/1999 | Pieken et al. | 435/6.11 |
| 6,933,116 B2 * | 8/2005 | Gold et al. | 435/5 |
| 2003/0198989 A1 * | 10/2003 | Gold et al. | 435/6 |
| 2005/0037343 A1 * | 2/2005 | Fagnani et al. | 435/6 |
| 2005/0136395 A1 * | 6/2005 | Mittmann | C12Q 1/701 435/5 |
| 2005/0215506 A1 * | 9/2005 | Bennett et al. | 514/44 |
| 2006/0003322 A1 * | 1/2006 | Bentwich | C12N 15/113 435/6.16 |
| 2007/0042380 A1 * | 2/2007 | Bentwich et al. | 435/6 |
| 2007/0259350 A1 * | 11/2007 | Bentwich et al. | 435/6 |
| 2010/0004432 A1 | 1/2010 | Miyakawa et al. | |
| 2011/0177578 A1 | 7/2011 | Nakamura et al. | |

FOREIGN PATENT DOCUMENTS

| | | |
|---|---|---|
| WO | WO-91/19813 A1 | 12/1991 |
| WO | WO-94/08050 A1 | 4/1994 |
| WO | WO-95/07364 A1 | 3/1995 |
| WO | WO 0159103 A2 * | 8/2001 |
| WO | WO-02/077262 A2 | 10/2002 |
| WO | WO 02095023 A2 * | 11/2002 |
| WO | WO-03/070984 A1 | 8/2003 |
| WO | WO-2004/032870 A2 | 4/2004 |
| WO | WO-2004/073653 A2 | 9/2004 |
| WO | WO-2004/096122 A2 | 11/2004 |
| WO | WO-2005/000194 A2 | 1/2005 |
| WO | WO 2005014607 A2 * | 2/2005 |
| WO | WO-2005/111077 A2 | 11/2005 |
| WO | WO-2006/110883 A2 | 10/2006 |
| WO | WO-2008059877 A1 | 5/2008 |
| WO | WO-2010008001 A1 | 1/2010 |

OTHER PUBLICATIONS

Mantyh et al, Molecular Mechanisms of Cancer Pain, 2002, Nature Reviews, vol. 2: 201-209.*
Bentwich et al-2, Sequence search result, 2013, STIC, 2 pages.*
Govoni et al, NGF and heart: Is there a role in heart disease?, 2011, Pharmacological Research, 63: 266-277.*
Binkley, J. et al., "RNA Ligands to Human Nerve Growth Factor," Nucleic Acids Research, vol. 23, No. 16, pp. 3198-3205, (1995).
Sproat, B. et al., "New Synthetic Routes to Synthons Suitable for 2'-O-allyloligoribonucleotide Assembly," Nucleic Acids Research, vol. 19, No. 14, pp. 733-738, (1991).
Cotten, M. et al., "2'-O-methyl, 2'-O-ethyl Oligoribonucleotides and Phosphorothioate Oligodeoxyribonucleotides as Inhibitors of the In Vitro U7 snRNP-dependent mRNA Processing Event," Nucleic Acids Research, vol. 19, No. 10, pp. 2629-2635, (1991).
Hobbs, J. et al., "Polynucleotides Containing 2'-Amino-2'-deoxyribose and 2'-Azido-2'-deoxyribose," Biochemistry, vol. 12, No. 25, pp. 5138-5145, (1973).
Ellington, A. and Szostak, J., " In Vitro Selection of RNA Molecules That Bind Specific Ligands," Nature, vol. 346, pp. 818-822, (1990).
Tuerk, C. et al., "Systematic Evolution of Ligands by Exponential Enrichment: RNA Ligands to Bacteriophage T4 DNA Polymerase," Science, vol. 249, pp. 505-510, (1990).

(Continued)

*Primary Examiner* — Ekaterina Poliakova-Georgantas
(74) *Attorney, Agent, or Firm* — Birch, Stewart, Kolasch & Birch, LLP

(57) ABSTRACT

Provided are an aptamer having an inhibitory activity against NGF; a complex containing an aptamer having a binding activity or inhibitory activity against NGF and a functional substance (e.g., affinity substances, labeling substances, enzymes, drug delivery vehicles, drugs and the like); a medicament, a diagnostic agent, a labeling agent and the like containing an aptamer having a binding activity or inhibitory activity against NGF, or a complex containing the aptamer and the functional substance; and the like.

14 Claims, 16 Drawing Sheets

Specification includes a Sequence Listing.

(56) References Cited

OTHER PUBLICATIONS

Zuker, M., "Mfold Web Server for Nucleic Acid Folding and Hybridization Prediction," Nucleic Acids Research, vol. 31, No. 13, pp. 3406-3415, (2003).
Fitzwater, T. and Polisky, B., "A SELEX Primer," Methods in Enzymology, vol. 267, pp. 275-301, (1996).
Miyagawa, S., "Aptamer Iyaku," Protein, Nucleic Acid and Enzyme, vol. 51, pp. 2521-2527, (2006).
Extended European Search Report, dated Feb. 16, 2012, for European Application No. 09816140.9.
Hermann, T. et al., "Adaptive Recognition by Nucleic Acid Aptamers," Science, vol. 287, XP-002952233, pp. 820-825 (2000).
Ulrich, H., "RNA Aptamers: From Basic Science Towards Therapy," HEP (Handbook of Experimental Phamacology), vol. 173, pp. 305-326 (2006).
Proske, D, et al., "Aptamers—basic research, drug development, and clinical applications," Appl. Microbiol. Biotechnol., vol. 69, 2005 (Published online: Nov. 11, 2005), pp. 367-374.
Lee, J.F. et al., "Aptamer therapeutics advance," Current Opinion in Chemical Biology, vol. 10, 2006 (available online Apr. 18, 2006), pp. 282-289.
Stoltenburg, R., et al., "SELEX-a (r)evolutionary method to generate high-affinity nucleic acid ligands," Biomol. Eng., vol. 24, No. 4, pp. 381-403, (2007).
Osborne, S.E., et al., "Nucleic Acid Selection and the Challenge of Combinatorial Chemistry," Chem. Rev., vol. 97, No. 2, pp. 349-370, (1997).
English Language International Search Report dated Jun. 14, 2011, issued in International Appl. No. PCT/JP2011/057105 of which copending U.S. Appl. No. 13/636,974 is the National Stage of.

* cited by examiner

APTAMER FOR NGF AND USE THEREOF

This application is the National Stage of International Application PCT/W2009/066457, filed Sep. 18, 2009, which claims priority under 35 USC § 119(a)-(d) of Japanese Application No. 244982/2008, filed Sep. 24, 2008.

TECHNICAL FIELD

The present invention relates to an aptamer for NGF, a method of utilizing the same, and the like.

BACKGROUND ART

Nerve growth factor (NGF) is the first neurotrophin identified in 1951, and is an important secretory protein involved in the development and survival of peripheral and central neurons. It consists of 118 amino acids, has a molecular weight of 13 kDa, and has S—S bonds at 3 positions in a molecule. BDNF, NT-3 and NT-4/5 are present in the family protein, which are structurally well conserved and form a homodimer by a noncovalent bond. It has a β sheet structure facing 3 different directions, and is considered to be dimerized in this part. It also has four loop structures with low homology among families, and these parts are considered to define specificity to receptors.

As NGF receptors, tyrosine kinase-type receptor TrkA with high affinity and p75 with low affinity which belongs to a tumor necrosis factor receptor superfamily are known. These receptors act as a homodimer or heterodimer and are deeply involved in the development and maintenance of the nervous system. TrkA is a single-pass transmembrane receptor and has a tyrosine kinase structure in the intracellular domain. When NGF is bound, tyrosine phosphorylation occurs, the signal is transmitted to the downstream, and promotion of differentiation and survival maintenance of the cell occur.

As family receptors of TrkA, TrkB and TrkC are known. TrkB is bound to BDNF and NT-4/5, and TrkC is bound to NT-3. p75 shows lower ligand specificity as compared to TrkA and is also bound to BDNF, NT-3 and NT-4/5 besides NGF. While p75 is a single-pass transmembrane receptor, it does not have a tyrosine kinase domain on the cytoplasmic side. Like TrkA, it is expressed not only in nerve cells but also in non-nerve cells. This receptor is known to be involved in the promotion of differentiation and survival maintenance of the cell, as well as related to the induction of apoptosis and cell migration. The results of crystal structure analysis have suggested that an NGF homodimer binds to TrkA at 2:2 and to p75 at 2:1. An NGF homodimer sometimes binds to a heterodimer of TrkA and p75.

NGF is produced by Schwann cell, keratinized cell, bronchial epithelial cell, fibroblast, T lymphocyte, macrophage, mast cell, B lymphocyte, keratinocyte, smooth muscle cell, renal glomerular cell, skeletal muscle cell and the like. On the other hand, TrkA is known to be expressed in nerve cell, as well as monocyte, T lymphocyte, B lymphocyte and mast cell other than nerve cell. Similarly, p75 is expressed in nerve cell as well as non-nerve cells.

It is well known that NGF plays a key role in the nervous system. It has been clarified that NGF has an action to maintain survival of cholinergic neuron and is considered to be related in some way to Alzheimer's disease. In addition, since intracerebral administration of NGF improves memory disorders of old rats, it is also expected as a therapeutic drug for senile dementia.

It has been found that NGF also acts on the tissues and cells other than the nervous system, and involved in the body's defense and tissue repair process. For example, it is known that administration of NGF to an animal increases blood vessel permeability, enhances immune responses of T cell and B cell, induces differentiation of lymphocytes, induces growth of mast cells, induces release of various cytokines from mast cells and the like.

NGF is related to inflammation, and increased expression of NGF has been observed in patients with inflammatory diseases and inflammatory animal models. Systemic lupus erythematosus, multiple sclerosis, psoriasis, arthritis, interstitial cystitis, asthma and the like are the examples thereof. It has been reported that the synovial fluid of patients with rheumatoid arthritis shows higher NGF concentration. In addition, increased NGF expression in rheumatoid arthritis model rats, and increase in mast cells and increased NGF expression in arthritis model mouse have been reported.

NGF is deeply involved in pain. When NGF is subcutaneously administered to human, a deep pain such as muscular pain continues for several days, and hyperalgesia of the injection site occurs. NGF knockout mouse and TrkA knockout mouse lacks unmyelinated nerve and do not feel pain. When NGF is intraperitoneally administered at 1 mg/kg to a mature rat, hyperalgesia against noxious heat and mechanical stimuli occurs. NGF transgenic mouse shows hyperalgesia unaccompanied by inflammatory conditions. In addition, it is known that the TrkA gene of patients with congenital insensitivity to pain with anhidrosis (CIPA) has abnormality, and pain sensation decreases when NGF gene has abnormality.

From the above, an NGF inhibitor can be used as a therapeutic drug for pain such as nociceptive pain, inflammatory pain, neuropathic pain, carcinomatous pain, fibromyalgia pain and the like. A combination therapy of NGF antibody and NSAID (WO04/073653), a combination therapy of NGF antibody and opioid analgesic (WO04/096122), a treatment method of postsurgical pain using an NGF antibody (WO04/032870, WO05/000194), a treatment method of pain of bone cancer using an NGF antibody (WO05/111077), and a treatment method of pain of osteoarthritis using an NGF antibody (WO06/110883) have been reported.

Tanezumab (PF-4383119 or RN624) is an antibody against NGF, shows effect in pain model experiment using an osteoarthritis animal model, and is currently under clinical trial. While the presence or absence of inhibitory activity of NGF and NGF receptor is unknown, there is a report relating to natural RNA that binds to NGF (non-patent document 1).

In recent years, applications of RNA aptamers to medicaments, diagnostic agents, and test drugs have been drawing attention; some RNA aptamers have already been in clinical study stage or in practical use. In December 2004, the world's first RNA aptamer drug, Macugen, was approved as a therapeutic drug for age-related macular degeneration in the US. An RNA aptamer refers to an RNA that binds specifically to a target molecule such as a protein, and can be prepared using the SELEX (Systematic Evolution of Ligands by Exponential Enrichment) method (Patent references 1-3). In the SELEX method, an RNA that binds specifically to a target molecule is selected from an RNA pool with about $10^{14}$ different nucleotide sequences. The RNA structure used has a random sequence of about 40 residues, which is flanked by primer sequences. This RNA pool is allowed to be assembled with a target substance, and only the RNA that has bound to the target substance is collected using a filter and the like. The RNA collected is amplified by RT-PCR, and this is used as a template for the next round. By repeating this operation about 10 times, an RNA aptamer that binds specifically to the target substance can be acquired.

Aptamer drugs, like antibody drugs, can target extracellular factors. With reference to many scientific papers and other reference materials in the public domain, aptamer drugs are judged to potentially surpass antibody drugs in some aspects. For example, aptamers often show higher binding force and higher specificity than do antibodies. Aptamers are unlikely to undergo immune elimination, and adverse reactions characteristic of antibodies, such as antibody-dependent cell-mediated cytotoxicity (ADCC) and complement-dependent cytotoxicity (CDC), are unlikely to occur with the use of aptamers. From the aspect of delivery, since aptamers are about 1/10 of antibody in size, delivery of a drug to the object site is easier. Since aptamers are produced by chemical synthesis, various modifications can be made easily, reduction of cost by large-scale production is possible. Meanwhile, the blood half-lives of aptamers are generally shorter than those of antibodies; however, this property is sometimes advantageous in view of toxicity. These facts lead to the conclusion that even when the same molecule is targeted, aptamer drugs potentially surpass antibody drugs.

DOCUMENT LIST

Patent Documents patent document 1: WO91/19813
patent document 2: WO94/08050
patent document 3: WO95/07364

Non-Patent Document non-patent document 1: Binkley J et al., (1995) Nucleic Acids Res, 23, 3198-3205

SUMMARY OF THE INVENTION

Problems to be Solved by the Invention

The present invention is directed to providing an aptamer for NGF and a method of utilizing the same, and the like.

Means of Solving the Problems

The present inventors investigated diligently to solve the problem described above and succeeded in preparing an aptamer of good quality for NGF, which resulted in the completion of the present invention.

Accordingly, the present invention provides the following:

[1] An aptamer that binds to NGF and inhibits binding of NGF and an NGF receptor;
[2] An aptamer that binds to NGF and inhibits a neurite outgrowth activity of NGF;
[3] The aptamer according to [2], having a 50% inhibitory concentration (IC50) of not more than 100 nM;
[4] The aptamer according to [2], having a 50% inhibitory concentration (IC50) of not more than 10 nM;
[5] The aptamer according to any one of [1] to [4], wherein at least one nucleotide is modified;
[6] The aptamer according to any one of [1] to [4], comprising a sequence shown by HGAANNNANCY (SEQ ID NO: 106), wherein N is any nucleotide, H is a nucleotide excluding G, Y is a pyrimidine nucleotide, and at least one nucleotide of the aforementioned sequence is modified;
[7] The aptamer according to any one of [1] to [4], comprising a sequence shown by UGAAANNANCY (SEQ ID NO: 107), CGAANNAAACY (SEQ ID NO: 108) or AGAANNAAACY (SEQ ID NO: 109), wherein N is any nucleotide, Y is a pyrimidine nucleotide and at least one nucleotide of the aforementioned sequence is modified;
[8] The aptamer according to any one of [1] to [4], comprising a sequence shown by UGAAAAAAACY (SEQ ID NO: 110), UGAAAGAAACY (SEQ ID NO: 111), CGAACAAAACY (SEQ ID NO: 112) or CGAAAGAAACY (SEQ ID NO: 113), wherein Y is a pyrimidine nucleotide and at least one nucleotide of the aforementioned sequence is modified;
[9] The aptamer according to any one of [5] to [8], wherein the hydroxyl groups at the 2'-position of a ribose of respective pyrimidine nucleotides are the same or different and unreplaced or replaced by an atom or group selected from the group consisting of a hydrogen atom, a fluorine atom and a methoxy group;
[10] The aptamer according to any one of [5] to [8], wherein the hydroxyl groups at the 2'-position of a ribose of respective purine nucleotides are the same or different and unreplaced or replaced by an atom or group selected from the group consisting of a hydrogen atom, a fluorine atom and a methoxy group;
[11] The aptamer according to [1], comprising any one of the nucleotide sequences (a), (b) and (c) below:
  (a) an aptamer comprising a nucleotide sequence selected from among SEQ ID NOs: 1-9, 12, 24-55 and 57-90 (wherein uracil may be thymine);
  (b) an aptamer comprising a nucleotide sequence selected from among SEQ ID NOs: 1-9, 12, 24-55 and 57-90 (wherein uracil may be thymine), wherein 1 or several nucleotides are replaced, deleted, inserted or added; and
  (c) a nucleotide sequence having an identity of 70% or more to a nucleotide sequence selected from among SEQ ID NOs: 1-9, 12, 24-55 and 57-90 (wherein uracil may be thymine);
[12] The aptamer according to [11], wherein at least one of the nucleotides has been modified;
[13] The aptamer according to [12], wherein the hydroxy groups at the 2'-position of respective pyrimidine nucleotides are the same or different and unreplaced or replaced by an atom or a group selected from the group consisting of a hydrogen atom, a fluorine atom and a methoxy group;
[14] The aptamer according to [12], wherein the hydroxy groups at the 2'-position of respective purine nucleotides are the same or different and unreplaced or replaced by an atom or a group selected from the group consisting of a hydrogen atom, a fluorine atom and a methoxy group;
[15] A complex comprising the aptamer of any one of [1] to [14] and a functional substance;
[16] The complex according to [15], wherein the functional substance is an affinity substance, a labeling substance, an enzyme, a drug delivery vehicle or a drug;
[17] A medicament comprising the aptamer of any one of [1] to [14] or the complex of [15] or [16];
[18] An anti-pain agent comprising the aptamer of any one of [1] to [14] or the complex of [15] or [16];
[19] An anti-inflammatory agent comprising the aptamer of any one of [1] to [14] or the complex of [15] or [16];
[20] A diagnostic agent comprising the aptamer of any one of [1] to [14] or the complex of [15] or [16];

[21] A probe for NGF detection, comprising the aptamer of any one of [1] to [14] or the complex of [15] or [16];
[22] A solid phase carrier for NGF purification, comprising the aptamer of any one of [1] to [14] or the complex of [15] or [16];
[23] A method of detecting NGF, comprising using the aptamer of any one of [1] to [14] or the complex of [15] or [16];
[24] A method of purifying NGF, comprising using the aptamer of any one of [1] to [14] or the complex of [15] or [16];
[25] A method of treating or preventing a disease accompanying a pain or inflammation, comprising administering the aptamer of any one of [1] to [14] or the complex of [15] or [16] to a subject in need thereof;
[26] Use of the aptamer of any one of [1] to [14] or the complex of [15] or [16] for a medicament for the treatment or prophylaxis of a disease accompanying a pain or inflammation;
[27] Use of the aptamer of any one of [1] to [14] or the complex of [15] or [16] for use as a medicament for the treatment or prophylaxis of a disease accompanying a pain or inflammation;
[28] Use of the aptamer of any one of [1] to [14] or the complex of [15] or [16] for use as a medicament for the treatment or prophylaxis of a disease accompanying a pain or inflammation;
[29] Use of the aptamer of any one of [1] to [14] or the complex of [15] or [16] for the production of a medicament for the treatment or prophylaxis of a disease accompanying a pain or inflammation.

Effect of the Invention

The aptamer and the complex of the present invention can be useful as medicaments, diagnostic agents or reagents for diseases such as pain, inflammatory disease and the like. The aptamer and the complex of the present invention can also be useful for the purification and concentration of NGF, as well as detection and quantification of NGF.

DESCRIPTION OF EMBODIMENTS

Figure 1:
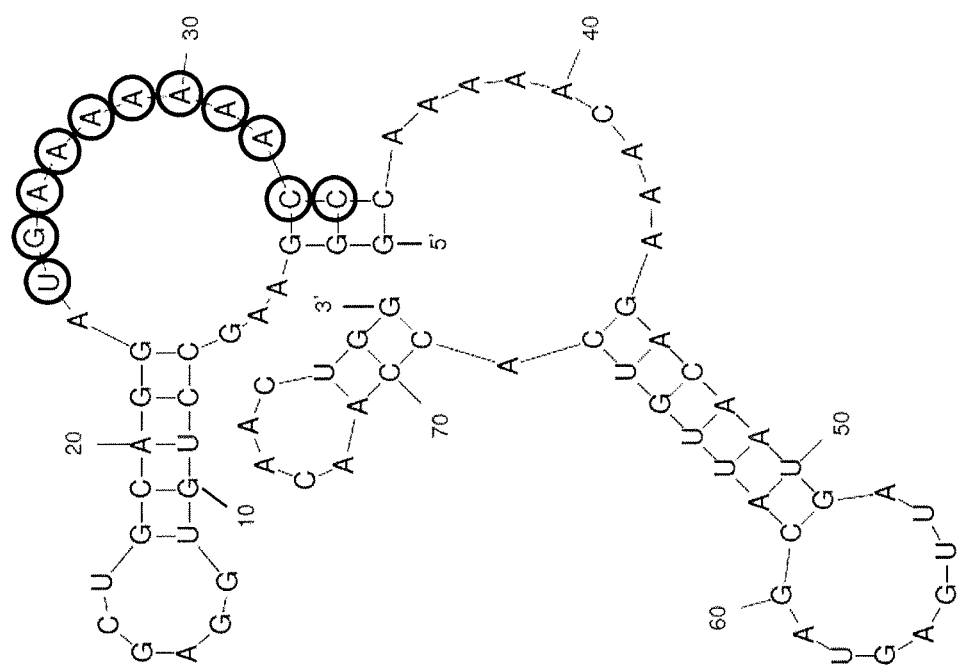
FIG. 1 shows the secondary structure of aptamer shown by SEQ ID NO: 1 predicted by the MFOLD program, wherein the part enclosed in a black circle shows a consensus sequence.
Figure 2:
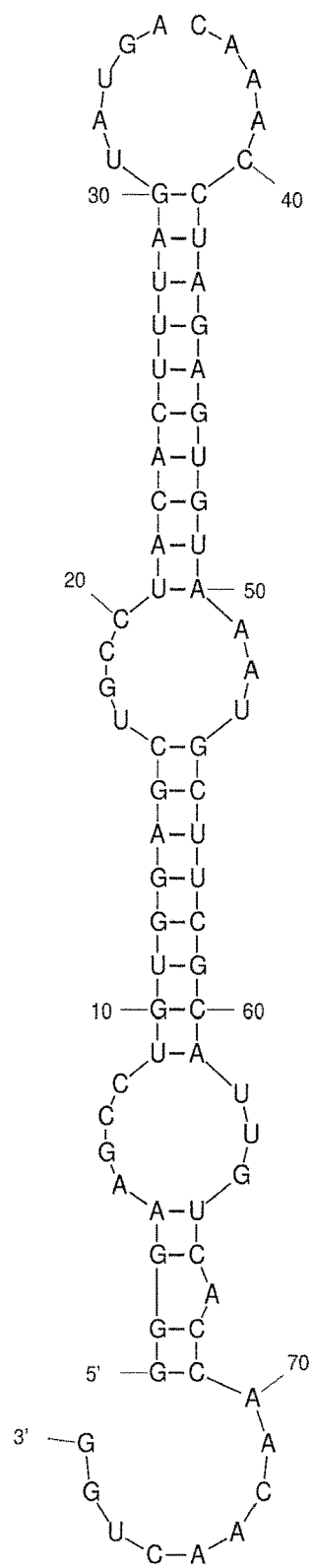
FIG. 2 shows the secondary structure of aptamer shown by SEQ ID NO: 2 predicted by the MFOLD program
Figure 3:
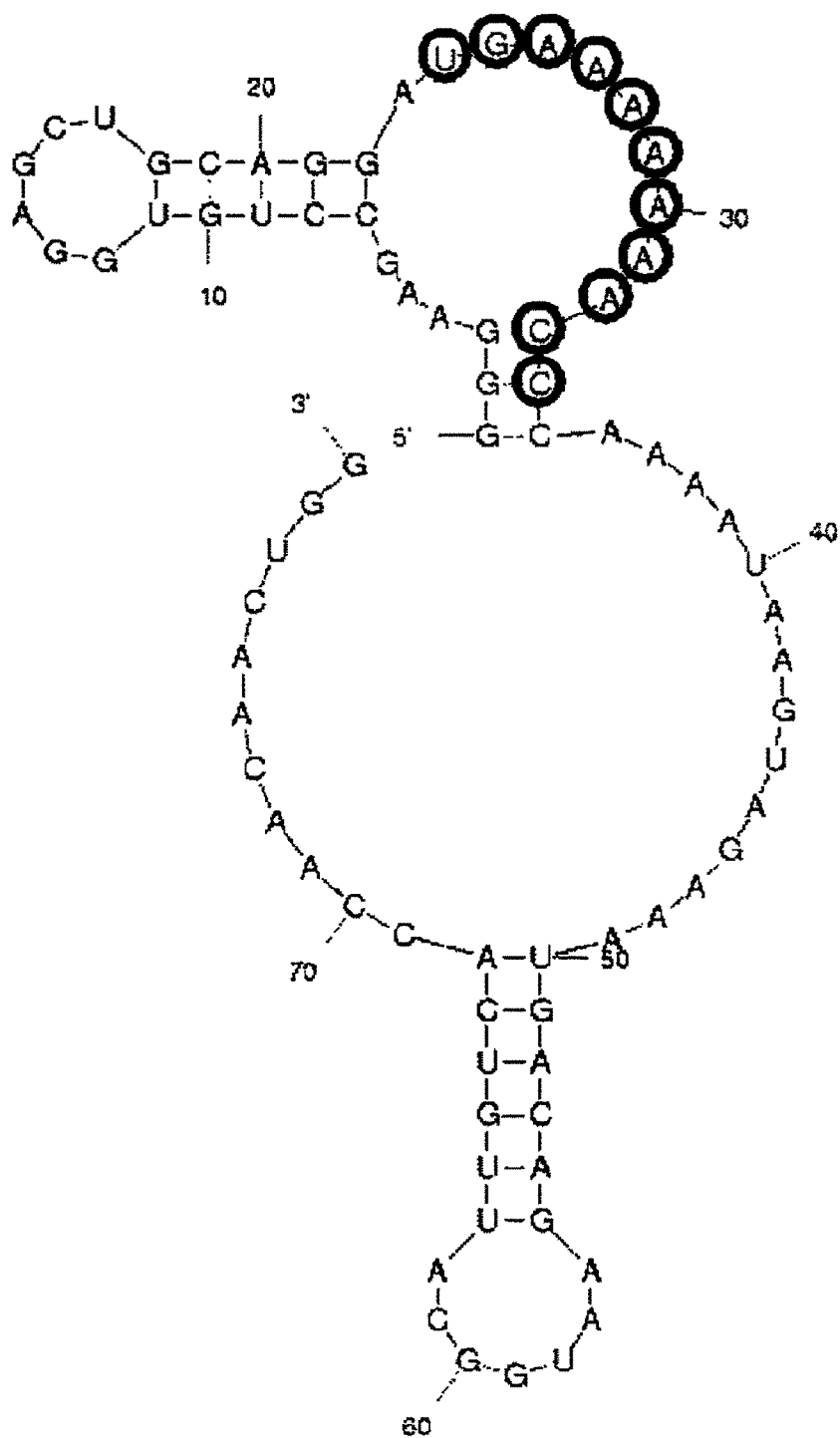
FIG. 3 shows the secondary structure of aptamer shown by SEQ ID NO: 3 predicted by the MFOLD program, wherein the part enclosed in a black circle shows a consensus sequence.
Figure 4:
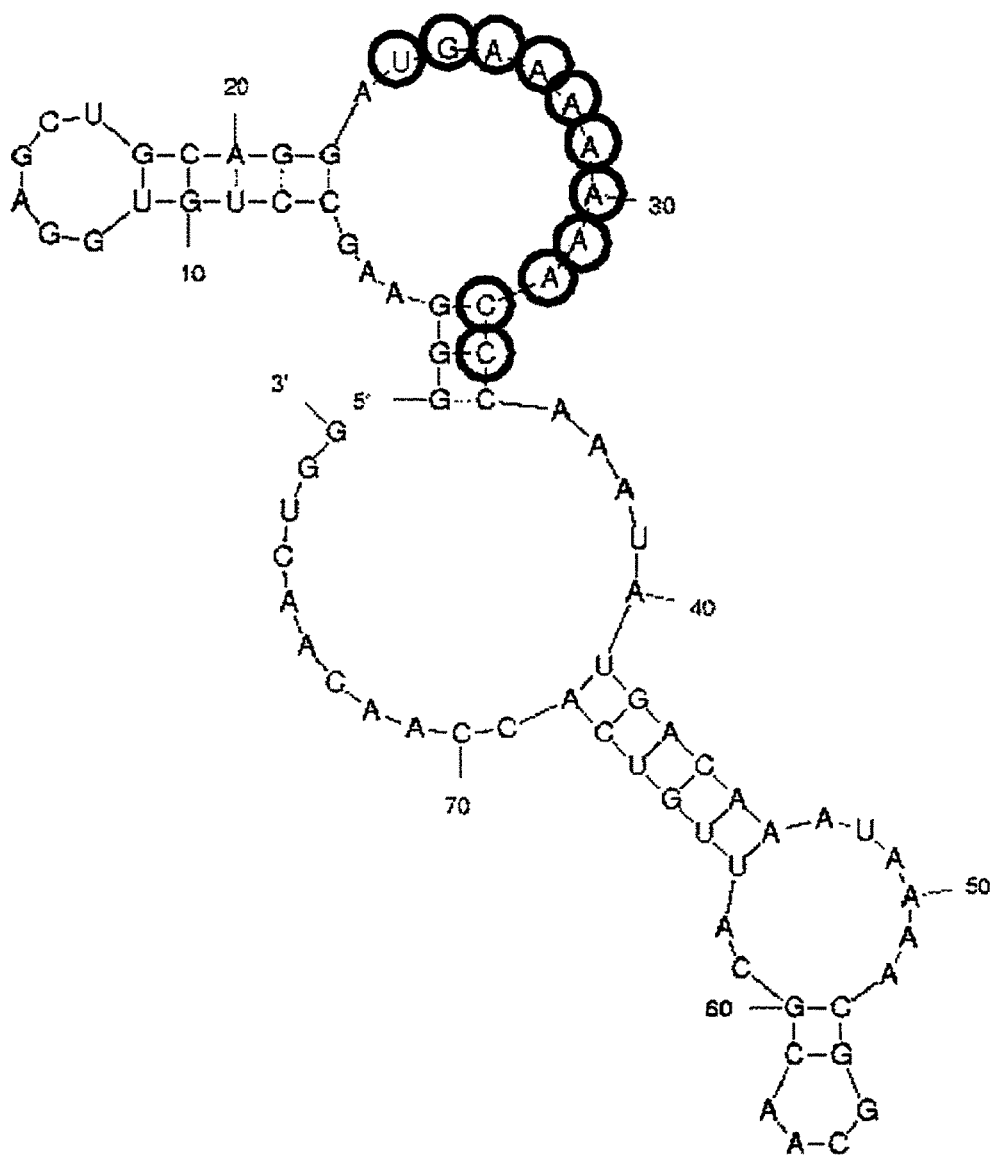
FIG. 4 shows the secondary structure of aptamer shown by SEQ ID NO: 4 predicted by the MFOLD program, wherein the part enclosed in a black circle shows a consensus sequence.
Figure 5:
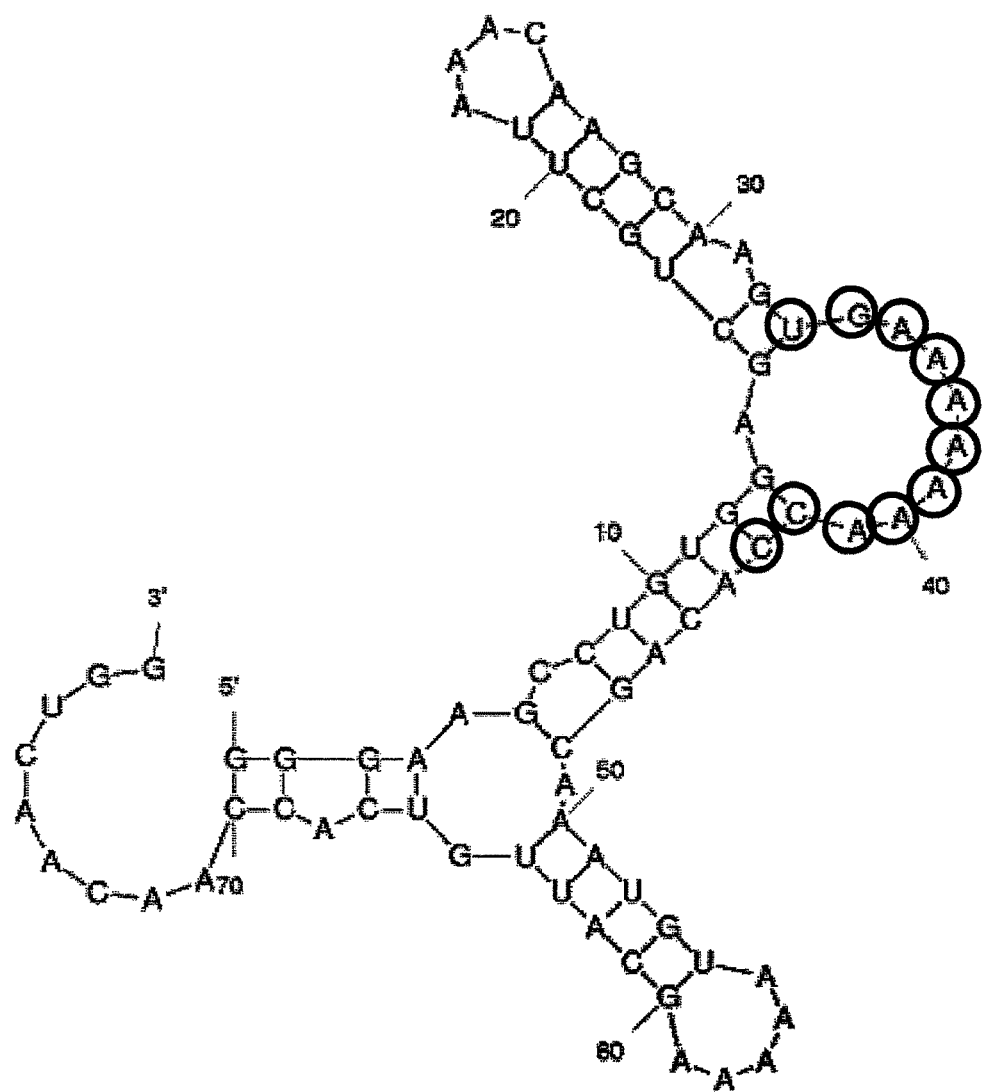
FIG. 5 shows the secondary structure of aptamer shown by SEQ ID NO: 5 predicted by the MFOLD program, wherein the part enclosed in a black circle shows a consensus sequence.
Figure 6:
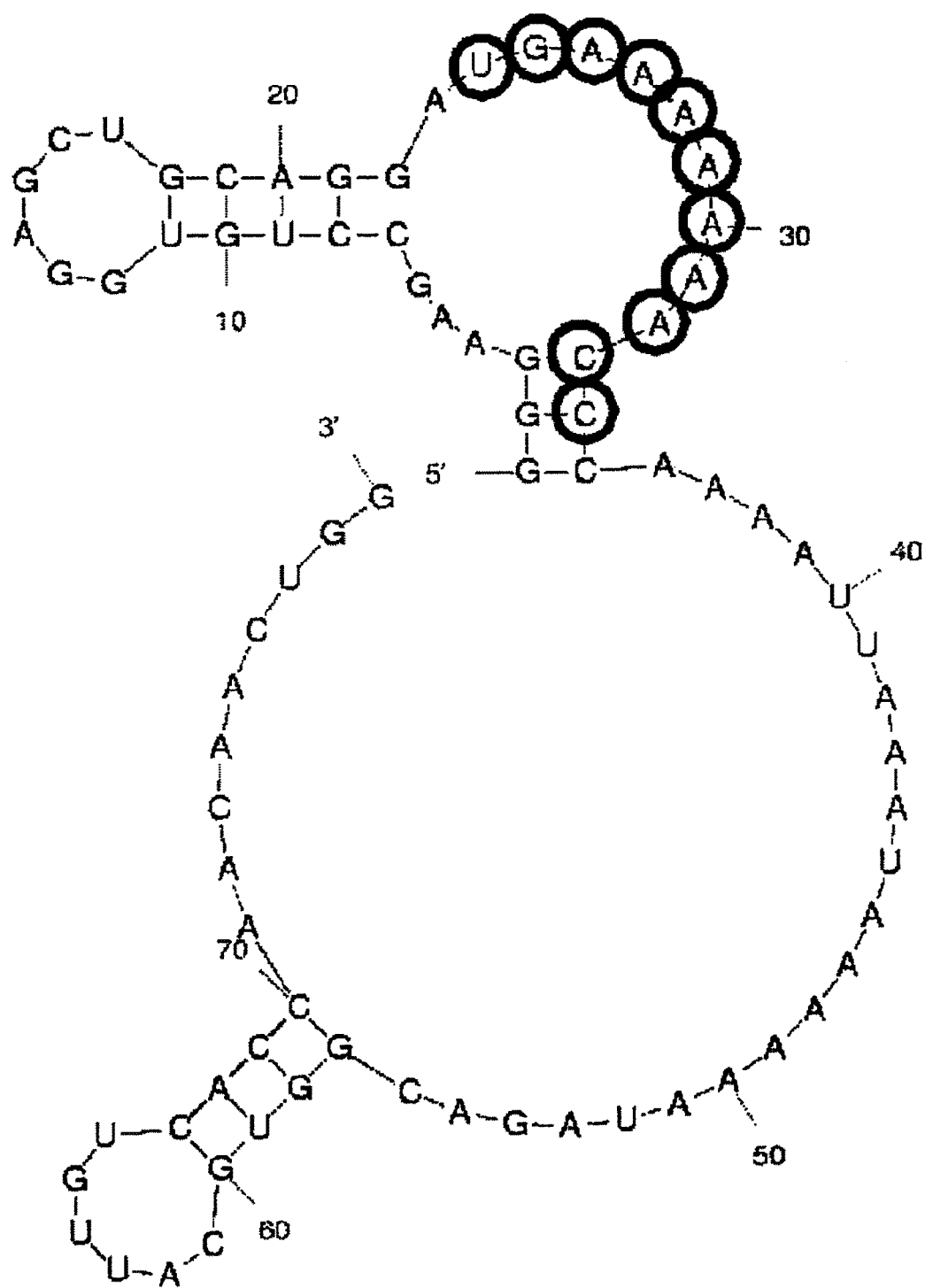
FIG. 6 shows the secondary structure of aptamer shown by SEQ ID NO: 6 predicted by the MFOLD program, wherein the part enclosed in a black circle shows a consensus sequence.
Figure 7:
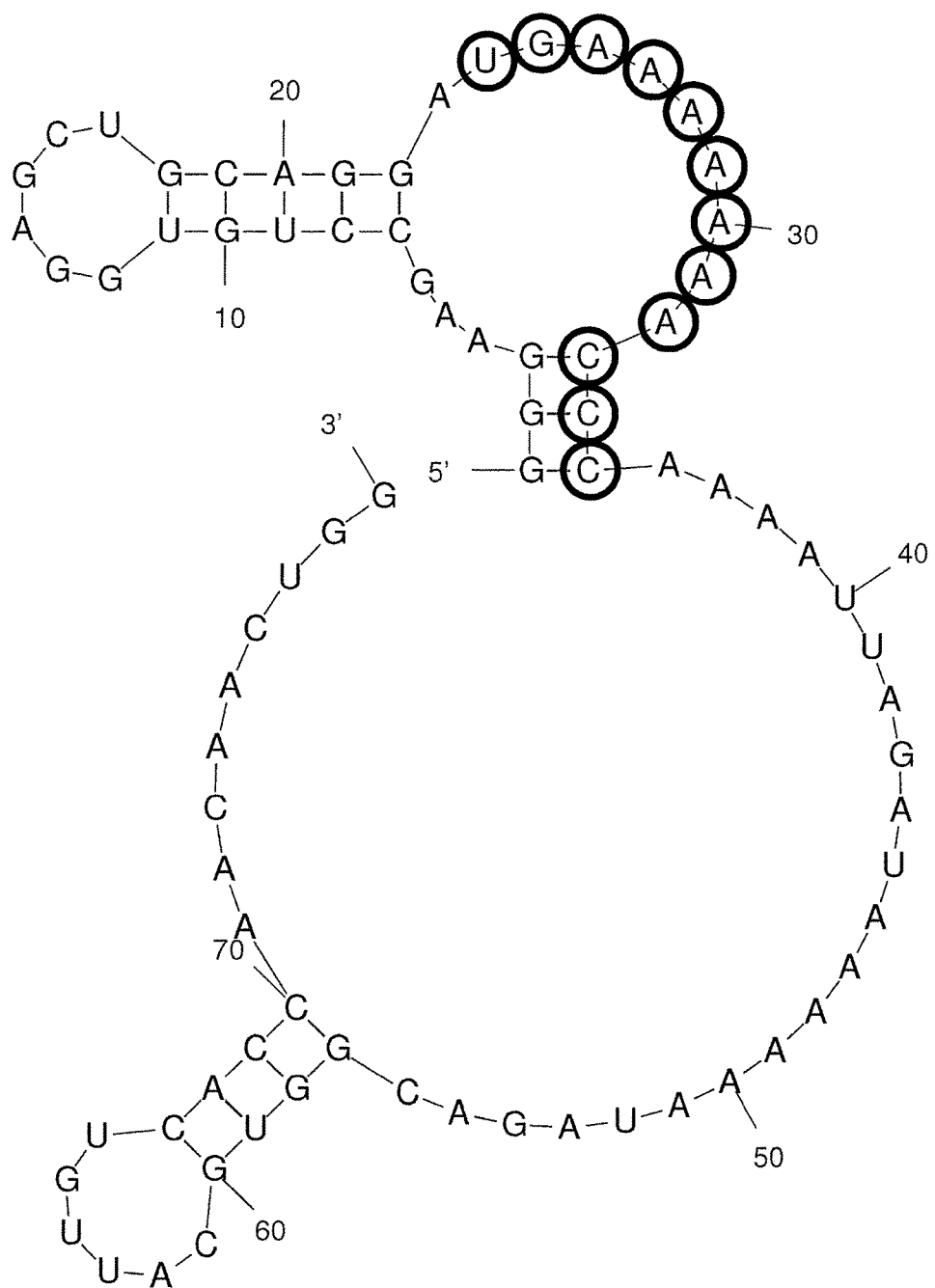
FIG. 7 shows the secondary structure of aptamer shown by SEQ ID NO: 7 predicted by the MFOLD program, wherein the part enclosed in a black circle shows a consensus sequence.
Figure 8:
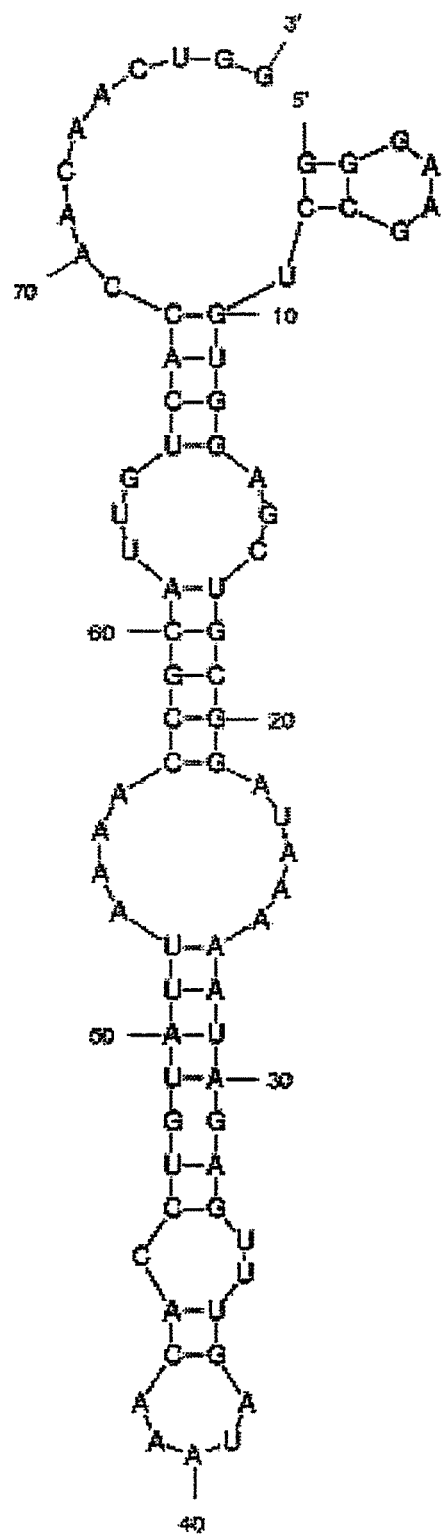
FIG. 8 shows the secondary structure of aptamer shown by SEQ ID NO: 8 predicted by the MFOLD program.
Figure 9:
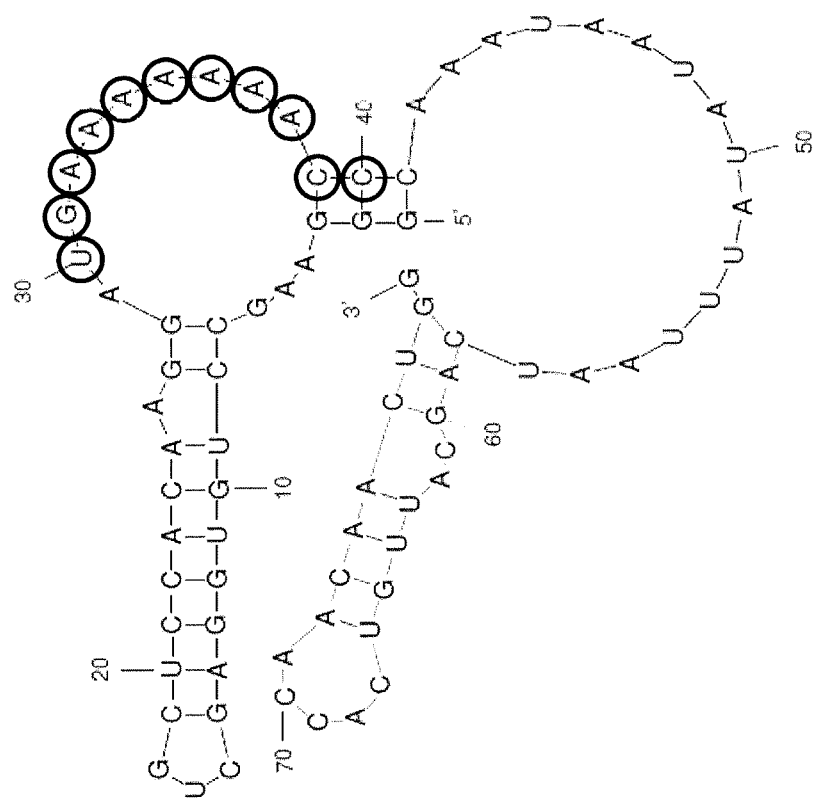
FIG. 9 shows the secondary structure of aptamer shown by SEQ ID NO: 9 predicted by the MFOLD program, wherein the part enclosed in a black circle shows a consensus sequence.
Figure 10A:
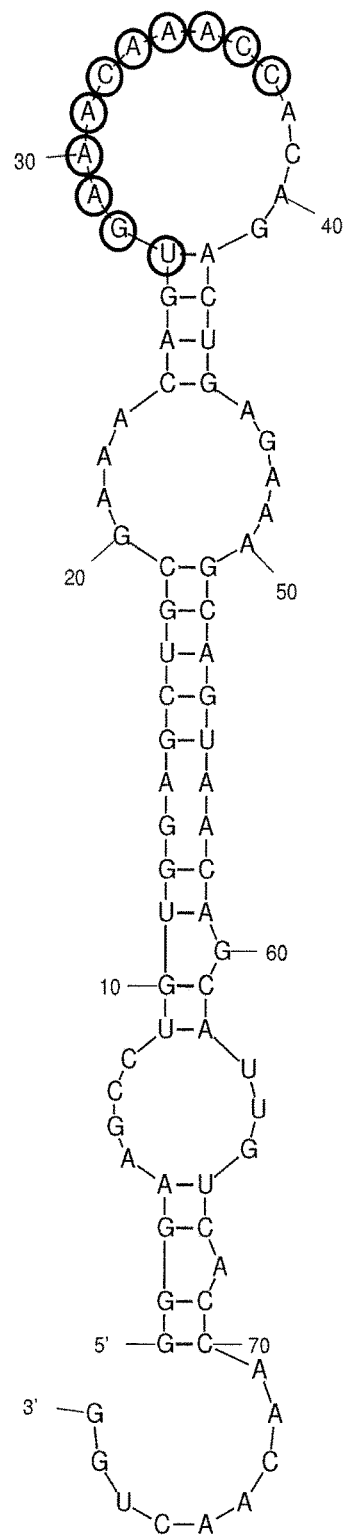
FIG. 10a shows the secondary structure of aptamer shown by SEQ ID NO: 12 predicted by the MFOLD program.
Figure 10B:
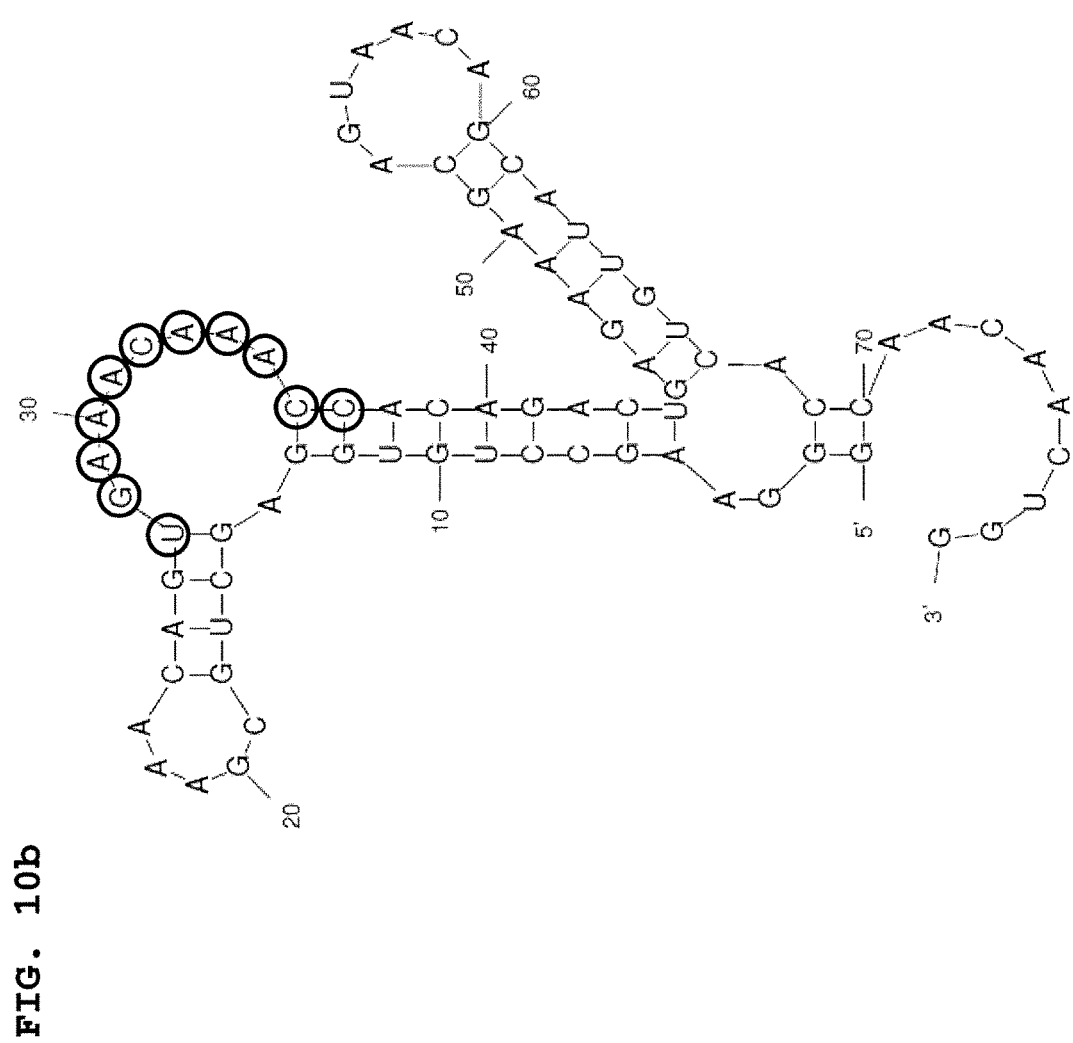
FIG. 10b shows the secondary structure of aptamer shown by SEQ ID NO: 12 predicted by the MFOLD program.

The present invention provides an aptamer having a binding activity to NGF. The aptamer of the present invention binds to NGF, and can inhibit the activity of NGF by inhibiting the binding of NGF and NGF receptor.

An aptamer refers to a nucleic acid molecule having a binding affinity for a particular target molecule. The aptamer can inhibit the activity of a particular target molecule by binding to the particular target molecule. The aptamer of the present invention may be an RNA, a DNA, a modified nucleic acid or a mixture thereof. The aptamer of the present invention can also be in a linear or circular form.

NGF is a known neurotrophin, and is an important secretory protein involved in the development and survival of peripheral and central neurons. NGF is an abbreviation of Nerve Growth Factor. In the present invention, NGF particularly means a β type NGF. The amino acid sequences of human β-NGF are those shown by Accession Numbers NP002497, P01138, AAI26151, AAI26149 and CAB75625, which may also be one with mutation, its domain or peptide. It may be not only a monomer but also a dimer or multimer.

The aptamer of the present invention binds to NGF in a physiological buffer (for example, solution A: see Example 1). The aptamer of the present invention binds to NGF at an intensity detectable by the following test.

For the measurement, BIAcore2000 manufactured by BIAcore is used. An aptamer is immobilized on a sensorchip. The amount to be immobilized is set to 1000 RU. A physiological buffer containing 0.3M NaCl (solution A: see Example 1) is used to prepare NGF solution (0.5 µM). This NGF solution (20 µL) is injected and the binding of NGF to the aptamer is detected. Using RNA containing a random nucleotide sequence consisting of 40 nucleotides as a negative control, when NGF significantly strongly binds to the aptamer as compared to the control RNA, the aptamer is evaluated to have bindability to NGF.

The aptamer of the present invention inhibits the activity of NGF by binding to NGF and inhibiting the binding of NGF and NGF receptor. In the present specification, the "inhibitory activity against NGF" means an inhibitory ability on any activity NGF has. For example, it means an activity to inhibit NGF from binding to NGF receptor.

In addition, examples of other "inhibitory activity against NGF" include inhibition of signal transduction in the downstream of NGF receptor (Ras-MAP kinase pathway, PI3 kinase pathway), inhibition of increased expression of TRPV1, SP, BDNF and the like, inhibitory activity of expression of HA, BK, PG, NGF and other cytokine released from mast cells etc. and the like, which result from the binding of NGF to NGF receptor.

Furthermore, differentiation of nerve cell induced by NGF, increase of survival, neurite outgrowth and blood vessel permeability, enhancement of immune response of T cells and B cells, differentiation of lymphocytes, inhibition of growth and the like of various cells such as mast cells, erythroleukemic cells, cancer cells and the like, relief of pain, hyperalgesia and the like can be mentioned.

Preferable "inhibitory activity against NGF" that the aptamer of the present invention has is an activity to inhibit the binding of NGF to NGF receptor, and an activity to inhibit neurite outgrowth activity induced by NGF.

In the present specification, the "NGF receptor" means a cell surface protein to which NGF binds. As the NGF receptor, TrkA and p75 are known. The NGF receptor referred to in the present invention may be a protein containing a natural amino acid sequence or a variant thereof. Here, the "variant thereof" means a protein or peptide wherein several amino acids of an amino acid sequence of "NGF receptor" have been replaced or a partial amino acid sequence thereof, which has a binding activity to NGF and inhibits the binding of NGF and NGF receptor.

The aptamer of the present invention binds to NGF and inhibits the binding of NGF and NGF receptor. Whether or not the aptamer inhibits the binding of NGF to NGF receptor can be evaluated by the following test.

For the measurement, BIAcore2000 manufactured by BIAcore is used. On a CM5 sensorchip is immobilized a fusion protein of NGF receptor and Fc (e.g., Trk A-Fc (175-TK, R&D systems)) or p75-Fc (R&D systems)). The amount to be immobilized is 1100 RU. NGF (0.1 µM) and an aptamer (0.33 µM) are mixed in a physiological buffer (solution A: see Example 1), and the mixture is prepared for 30 min. This mixture (20 µL) is injected, and the binding of NGF to NGF receptor is detected. When the inhibitory activity (%) is not less than 60%, the aptamer is evaluated to inhibit the binding of NGF to NGF receptor. The inhibitory activity (%) is calculated with the binding amount of NGF free of an aptamer and NGF receptor as 0, and a binding amount by injection of an NGF-free solution as 100. Here, the binding amount means RU value at a peak top of the sensorgram of BIAcore (RU value immediately after completion of NGF injection).

In one embodiment, the aptamer of the present invention can inhibit both the binding of NGF and TrkA, and that of NGF and p75.

The aptamer of the present invention can exhibit inhibitory activity against NGF derived from any mammals. Such mammals include primates (e.g., human, monkey), rodents (e.g., mouse, rat and guinea pig), and companion animals, domestic animals and working animals (e.g., dog, cat, horse, bovine, goat, sheep, swine).

The aptamer of the present invention is not particularly limited as long as it binds to any portion of NGF and can inhibit the binding of NGF and NGF receptor.

In one preferable embodiment, the aptamer of the present invention contains a sequence shown by HGAANNNANCY (SEQ ID NO: 106) wherein N is any nucleotide, H is a nucleotide excluding G, and Y is a pyrimidine nucleotide, binds to NGF, and inhibits the binding of NGF and NGF receptor. The nucleotide sequence shown by SEQ ID NO: 106 is included in the aptamer that binds to NGF and inhibits the binding of NGF and NGF receptor, which is obtained by the below-mentioned SELEX method. At least one nucleotide of the aforementioned sequence is preferably modified.

In one preferable embodiment, the aptamer of the present invention contains a consensus sequence shown by UGAAANNANCY (SEQ ID NO: 107), CGAANNAAACY (SEQ ID NO: 108) or AGAANNAAACY (SEQ ID NO: 109) wherein N is any nucleotide, and Y is a pyrimidine nucleotide, binds to NGF, and inhibits the binding of NGF and NGF receptor. The nucleotide sequences shown by SEQ ID NO: 107, SEQ ID NO: 108 and SEQ ID NO: 109 are included in the aptamer that binds to NGF and inhibits the binding of NGF and NGF receptor, which is obtained by the below-mentioned SELEX method. At least one nucleotide of these sequences is preferably modified.

In one preferable embodiment, the aptamer of the present invention contains a consensus sequence shown by UGAAAAAAACY (SEQ ID NO: 110), UGAAAGAAACY (SEQ ID NO: 111), CGAACAAAACY (SEQ ID NO: 112) or CGAAAGAAACY (SEQ ID NO: 113) wherein Y is a pyrimidine nucleotide, binds to NGF, and inhibits the binding of NGF and NGF receptor. The nucleotide sequences shown by SEQ ID NO: 110, SEQ ID NO: 111, SEQ ID NO: 112 and SEQ ID NO: 113 are included in the aptamer that binds to NGF and inhibits the binding of NGF and NGF receptor, which is obtained by the below-mentioned SELEX method. At least one nucleotide of these sequences is preferably modified.

In addition, the aptamer of the present invention can be an aptamer that binds to NGF and inhibits a neurite outgrowth activity of NGF. Whether or not the aptamer inhibits the neurite outgrowth activity of NGF can be evaluated by the test described in Example 7 or Example 8.

In addition, the aptamer concentration (IC50) to afford a neurite outgrowth activity of 50% can also be determined by performing the test described in Example 8 with different aptamer concentrations. The IC50 of the aptamer of the present invention is preferably not more than 100 nM, more preferably not more than 10 nM.

The length of the aptamer of the present invention is not limited, and can usually be about 10 to about 200 nucleotides, and can be, for example, not more than about 100 nucleotides, preferably not more than about 60 nucleotides, more preferably not more than about 50 nucleotides, most preferably not more than about 45 nucleotides. When the total number of nucleotides is smaller, chemical synthesis and mass-production will be easier, and there is a major advantage in terms of cost. It is also thought that chemical modification is easier, stability in the body is higher, and toxicity is lower.

Each nucleotide contained in the aptamer of the present invention is the same or different and can be a nucleotide comprising a hydroxyl group at the 2' position of ribose (e.g., ribose of pyrimidine nucleotide, ribose of purine nucleotide) (i.e., an unreplaced nucleotide) or a nucleotide replaced by any atom or group at the 2' position of ribose. As examples of any such atom or group, a nucleotide replaced by a hydrogen atom, a fluorine atom or an —O-alkyl group (e.g., —O-Me group), an —O-acyl group (e.g., —O—CHO group), or an amino group (e.g., —NH$_2$ group) can be mentioned.

The aptamer of the present invention can also be the nucleotide wherein at least one kind (e.g., 1, 2, 3 or 4% kinds) of nucleotide comprises a hydroxyl group, or the above-described any atom or group, for example, at least two kinds (e.g., 2, 3 or 4 kinds) of groups selected from the group consisting of a hydrogen atom, a fluorine atom, a hydroxyl group and a —O-Me group, at the 2' position of ribose.

Also, in the aptamer of the present invention, all pyrimidine nucleotides are the same or different and each can be a nucleotide replaced by a fluorine atom, or a nucleotide replaced by any atom or group mentioned above, preferably an atom or group selected from the group consisting of a hydrogen atom, a hydroxyl group and a methoxy group at the 2' position of ribose.

In the aptamers of the present invention, moreover, all purine nucleotides are the same or different and each can be a nucleotide replaced by a hydroxyl group at the 2'-position of ribose, or a nucleotide replaced by any atom or group mentioned above, preferably an atom or a group selected from the group consisting of a hydrogen atom, a methoxy group, and a fluorine atom.

The aptamer of the present invention can also be one wherein all nucleotides comprise a hydroxyl group, or any atom or group mentioned above, for example, the identical group selected by the group consisting of a hydrogen atom, a fluorine atom, a hydroxyl group and a —O-Me group, at the 2' position of ribose.

In this specification, the nucleotides constituting the aptamer are assumed to be RNAs (i.e., the sugar groups are assumed to be ribose) in describing how the sugar groups are modified in the nucleotides. However, this does not mean that DNA is exempted from the aptamer-constituting nucleotides, and a modification of RNA should read as a modification of DNA as appropriate. When the nucleotide constituting the aptamer is DNA, for example, substitution of the hydroxyl group at the 2' position of ribose by X should read as a substitution of one hydrogen atom at the 2' position of deoxyribose by X.

The aptamer of the present invention can also be:
(a) an aptamer comprising a nucleotide sequence selected from among SEQ ID NO:1-9, 12, 24-55 and 57-90 (with the provision that the uracil may be thymine);
(b) an aptamer comprising a nucleotide sequence selected from among SEQ ID NO:1-9, 12, 24-55 and 57-90 (with the provision that the uracil may be thymine), wherein one to several nucleotides are replaced, deleted, inserted or added;
(c) an aptamer comprising a nucleotide sequence having an identity of 70% or more (preferably 80% or more, more preferably 90% or more, most preferably 95% or more) to a nucleotide sequence selected from among SEQ ID NO: 1-9, 12, 24-55 and 57-90 (with the provision that the uracil may be thymine); or
(d) a conjugate selected from the group consisting of a conjugate of a plurality of aptamers (a) above, a conjugate of a plurality of aptamers (b) above, a conjugate of a plurality of aptamers (c) above, and a conjugate of a plurality of aptamers (a), (b) and (c) above.

The aptamers of the above-mentioned (b)-(d) can bind to NGF and/or inhibit the activity of NGF (NGF receptor binding activity etc.).

In addition, preferably, the aptamers of the above-mentioned (b)-(d) bind to NGF and inhibit the binding of NGF and NGF receptor, and/or bind to NGF, and inhibit the neurite outgrowth activity of NGF.

More preferably, the aptamers of the above-mentioned (b)-(d) show an NGF neurite outgrowth inhibitory concentration of not more than 100 nM, more preferably not more than 10 nM.

In (b) above, the number of nucleotides replaced, deleted, inserted or added is not particularly limited as long as the aptamer binds to NGF, and can inhibit the activity of NGF (NGF receptor binding activity etc.). It can be, for example, not more than about 30, preferably not more than about 20, more preferably not more than about 10, still more preferably not more than 5, most preferably 4, 3, 2 or 1.

With respect to (c) above, "an identity" means a ratio (%) of identical nucleotide residues to all overlapping nucleotide residues in the optimal alignment where two nucleotide sequences are aligned using a mathematical algorithm known in the technical field (preferably, the algorithm considers introduction of gaps on one or both of the sequences for the best alignment).

Nucleotide sequence identity in the present specification can be calculated by, for example, aligning the two nucleotide sequences using the homology calculation algorithm NCBI BLAST-2 (National Center for Biotechnology Information Basic Local Alignment Search Tool) under the following conditions (gap open=5 penalties; gap extension=2 penalties; x_dropoff=50; expectation value=10; filtering=ON).

In (d) above, conjugation can be achieved by tandem binding. In the conjugation, a linker may be utilized. As the linker, nucleotide chains (e.g., 1 to about 20 nucleotides) and non-nucleotide chains (e.g., —(CH$_2$)$_n$— linker, —(CH$_2$CH$_2$O)$_n$— linker, hexaethylene glycol linker, TEG linker, peptide-containing linker, —S—S— bond-containing linker, —CONH— bond-containing linker, —OPO$_3$— bond-containing linker) can be mentioned. The plurality as mentioned in the above-described plural conjugates is not particularly limited, as long as it is two or more, and the plurality can be, for example, 2, 3 or 4. Each of the nucleotides in (a) to (d) above, whether the same or different, can be a nucleotide comprising a hydroxyl group at the 2' position of ribose, or a nucleotide replaced by any groups (e.g., a hydrogen atom, fluorine atom or —O-Me group) at the 2' position of ribose (e.g., ribose of pyrimidine nucleotide).

The aptamer of the present invention may be one wherein a sugar residue (e.g., ribose) of each nucleotide has been modified to increase the NGF binding activity, NGF-NGF receptor binding inhibitory activity, NGF neurite outgrowth inhibitory activity, stability of aptamer, drug deliverability and the like. As examples of the modification in a sugar residue, replacement of oxygen atom at the 2'-position, 3'-position and/or 4'-position of the sugar residue with another atom, and the like can be mentioned. As the kind of the modification, fluorination, O-alkylation (e.g., O-methylation, O-ethylation), O-arylation, S-alkylation (e.g., S-methylation, S-ethylation), S-arylation, and amination (e.g., —$NH_2$) can be mentioned. Such alterations in the sugar residue can be performed by a method known per se (see, for example, Sproat et al., (1991) Nucl. Acid. Res. 19, 733-738; Cotton et al., (1991) Nucl. Acid. Res. 19, 2629-2635; Hobbs et al., (1973) Biochemistry 12, 5138-5145).

The aptamer of the present invention may also have a nucleic acid base (e.g., purine or pyrimidine) altered (e.g., chemical substitution) to increase the NGF binding activity, NGF-NGF receptor binding inhibitory activity, NGF neurite outgrowth inhibitory activity and the like. As examples of such alterations, pyrimidine alteration at 5-position, purine alteration at 6- and/or 8-position(s), alteration with an extracyclic amine, substitution with 4-thiouridine, and substitution with 5-bromo or 5-iodo-uracil can be mentioned. The phosphate group contained in the aptamer of the present invention may be altered to confer resistance to nuclease and hydrolysis. For example, the P(O)O group may be replaced with P(O)S (thioate), P(S)S (dithioate), P(O)$NR_2$ (amidate), P(O)R, R(O)OR', CO or $CH_2$ (formacetal) or 3'-amine (—NH—$CH_2$—$CH_2$—) [wherein each unit of R or R' is independently H or a replaced or unreplaced alkyl (e.g., methyl, ethyl)].

The joining group is, for example, —O—, —N— or —S—, and nucleotides can bind to an adjoining nucleotide via these joining groups.

The alterations may also include alterations such as capping at 3' and 5'.

An alteration can further be performed by adding to an end a polyethyleneglycol, amino acid, peptide, inverted dT, nucleic acid, nucleosides, Myristoyl, Lithocolic-oleyl, Docosanyl, Lauroyl, Stearoyl, Palmitoyl, Oleoyl, Linoleoyl, other lipids, steroids, cholesterol, caffeine, vitamins, pigments, fluorescent substances, anticancer agent, toxin, enzymes, radioactive substance, biotin and the like. For such alterations, see, for example, U.S. Pat. Nos. 5,660,985 and 5,756,703.

The aptamer of the present invention can be chemically synthesized as disclosed herein and by a method known per se in the art. An aptamer binds to the target molecule in a wide variety of binding modes, such as ionic bonds based on the negative charge of the phosphate group, hydrophobic bonds and hydrogen bonds based on ribose, and hydrogen bonds and stacking interaction based on nucleic acid bases. In particular, ionic bonds based on the negative charge of the phosphate group, which are present in the same number as the number of constituent nucleotides, are strong, and bind to lysine and arginine being present on the surface of the positive charge of protein. For this reason, nucleic acid bases not involved in the direct binding to the target molecule can be substituted. In particular, because the region of stem structure has already formed base pairs and faces the inside of the double helical structure, nucleic acid bases are unlikely to bind directly to the target molecule. Therefore, even when a base pair is replaced with another base pair, the activity of the aptamer often does not decrease. In structures wherein no base pairs are formed, such as loop structures, provided that the nucleic acid base is not involved in the direct binding to the target molecule, base substitution is possible. Regarding modifications of the 2'-position of ribose, the functional group at the 2'-position of ribose infrequently interacts directly with the target molecule, but in many cases, it is of no relevance, and can be substituted by another modified molecule. Hence, an aptamer, unless the functional group involved in the direct binding to the target molecule is substituted or deleted, often retains the activity thereof. It is also important that the overall three-dimensional structure does not change substantially.

An aptamer can be prepared by utilizing the SELEX method or an improved version thereof (e.g., Ellington et al., (1990) Nature, 346, 818-822; Tuerk et al., (1990) Science, 249, 505-510). In the SELEX method, by increasing the number of rounds or using a competing substance, an aptamer exhibiting a stronger binding potential for the target molecule is concentrated and selected. Hence, by adjusting the number of rounds of SELEX and/or changing the competitive condition, aptamers with different binding forces, aptamers with different binding modes, and aptamers with the same binding force or binding mode but different base sequences can be obtained in some cases. The SELEX method comprises a process of amplification by PCR; by causing a mutation by using manganese ions and the like in the process, it is possible to perform SELEX with higher diversity.

The aptamers obtained by SELEX are nucleic acids that exhibit high affinity for the target substance, but this does not mean binding to an active site of the target substance. Therefore, the aptamers obtained by SELEX do not necessarily act on the function of the target substance. NGF is a basic protein, and is thought to be likely to allow nucleic acids to bind thereto nonspecifically. An aptamer that does not bind to an active site does not influence the activity of the target substance. In fact, the RNA used for control did not inhibit the binding of NGF and NGF receptor.

Based on an active aptamer thus selected, SELEX can be performed by further changing a primer to acquire an aptamer possessing higher activity. Specifically, after preparing a template wherein an aptamer with a determined sequence is partially randomized or a template doped with about 10 to 30% of random sequences, SELEX is performed again.

An aptamer obtained by SELEX has a length of about 80 nucleotides, and this is difficult to prepare as a pharmaceutical as it is. Hence, it is necessary to repeat try-and-error efforts to shorten the aptamer to a length of about 50 nucleotides or less enabling easy chemical synthesis. Depending on the primer design for an aptamer obtained by SELEX, the ease of the subsequent minimization operation changes. Unless the primer is designed successfully, subsequent development will be impossible even if an aptamer with activity is selected by SELEX. In the present invention, an aptamer retaining activity even with 38 nucleotides was obtained.

Aptamers are modified easily since they permit chemical synthesis. For aptamers, by predicting the secondary structure using the MFOLD program, or by predicting the steric structure by X-ray analysis or NMR analysis, it is possible to predict to some extent which nucleotide can be substituted or deleted, and where to insert a new nucleotide. A predicted aptamer with the new sequence can easily be chemically synthesized, and it can be determined whether or not the aptamer retains the activity using an existing assay system.

If a region important to the binding of the obtained aptamer with the target molecule is identified by repeated try-and-error efforts as described above, the activity remains unchanged in many cases even when a new sequence is added to both ends of the sequence. The length of the new sequence is not particularly limited. Particularly, the aforementioned sequences shown by HGAANNNANCY (SEQ ID NO: 106), UGAAANNANCY (SEQ ID NO: 107), CGAANNAAACY (SEQ ID NO: 108), AGAANNAAACY (SEQ ID NO: 109), UGAAAAAAACY (SEQ ID NO: 110), UGAAAGAAACY (SEQ ID NO: 111), CGAACAAAAC (SEQ ID NO: 112) and CGAAAGAAAC (SEQ ID NO: 113) are important portions for binding of the aptamer of the present invention to NGF and inhibition of the binding of NGF and NGF receptor. Even when a new sequence is added to both ends of these sequences, the activity remains unchanged in many cases.

Modifications, like sequences, afford a wide range of design or alterations.

As stated above, aptamers permit a wide range of design or alterations of modifications. The present invention also provides a production method of aptamer that enables a wide range of design or alteration of an aptamer comprising a specified sequence (e.g., a sequence corresponding to a portion selected from among stem regions, internal loop regions, hairpin loop regions and single-strand regions: hereinafter, abbreviated as fixed sequence as required).

For example, the production method of such aptamer includes production of an aptamer comprising a fixed sequence by using a single kind of nucleic acid molecule consisting of a nucleotide sequence shown by:

Primer sequence (i)-(N)a-fixed sequence-(N)b-Primer sequence (ii)

[wherein (N)a represents a nucleotide chain consisting of "a" units of N; (N)$_b$ represents a nucleotide chain consisting of "b" units of N; each of the units of N, whether identical or different, is a nucleotide selected from the group consisting of A, G, C, U and T (preferably, A, G, C and U). Each of "a" and "b", whether identical or different, can be any numbers, and can be, for example, 1 to about 100, preferably 1 to about 50, more preferably 1 to about 30, still more preferably 1 to about 20 or 1 to about 10], or plural kinds of nucleic acid molecules (e.g., library of nucleic acid molecule different in the number of a, b etc.) and primer pairs corresponding to the primer sequences (i) and (ii), respectively.

The present invention also provides a complex comprising the aptamer of the present invention and a functional substance bound thereto. The bond between the aptamer and the functional substance in the complex of the present invention can be a covalent bond or a non-covalent bond. The complex of the present invention can be one wherein the aptamer of the present invention and one or more (e.g., 2 or 3) of functional substances of the same kind or different kinds are bound together. The functional substance is not particularly limited, as far as it newly confers a certain function to an aptamer of the present invention, or is capable of changing (e.g., improving) a certain characteristic which an aptamer of the present invention can possess. As examples of the functional substance, proteins, peptides, amino acids, lipids, sugars, monosaccharides, polynucleotides, and nucleotides can be mentioned. As examples of the functional substance, affinity substances (e.g., biotin, streptavidin, polynucleotides possessing affinity for target complementary sequence, antibodies, glutathione Sepharose, histidine), substances for labeling (e.g., fluorescent substances, luminescent substances, radioisotopes), enzymes (e.g., horseradish peroxidase, alkaline phosphatase), drug delivery vehicles (e.g., liposome, microspheres, peptides, polyethyleneglycols), drugs (e.g., those used in missile therapy such as calicheamycin and duocarmycin; nitrogen mustard analogues such as cyclophosphamide, melphalan, ifosfamide or trofosfamide; ethylenimines such as thiotepa; nitrosoureas such as carmustine; alkylating agents such as temozolomide or dacarbazine; folate-like metabolic antagonists such as methotrexate or raltitrexed; purine analogues such as thioguanine, cladribine or fludarabine; pyrimidine analogues such as fluorouracil, tegafur or gemcitabine; vinca alkaloids such as vinblastine, vincristine or vinorelbine and analogues thereof; podophyllotoxin derivatives such as etoposide, taxans, docetaxel or paclitaxel; anthracyclines such as doxorubicin, epirubicin, idarubicin and mitoxantrone, and analogues thereof; other cytotoxic antibiotics such as bleomycin and mitomycin; platinum compounds such as cisplatin, carboplatin and oxaliplatin; pentostatin, miltefosine, estramustine, topotecan, irinotecan and bicalutamide), and toxins (e.g., ricin toxin, liatoxin and Vero toxin) can be mentioned. These functional molecules are finally removed in some cases. Furthermore, the molecules may be peptides that can be recognized and cleaved by enzymes such as thrombin, matrix metalloproteinase (MMP), and Factor X, and may be polynucleotides that can be cleaved by nucleases or restriction endonuclease.

The aptamer or the complex of the present invention can be used as, for example, a medicament or a diagnostic agent, a test drug, a reagent, an additive for drinking water and food, an enhancer and a mitigator.

The aptamer and complex of the present invention can have an activity to inhibit the function of NGF by binding to NGF and inhibiting the binding of NGF and NGF receptor. As mentioned above, NGF is deeply involved in the pain and inflammation. Therefore, the aptamer and complex of the present invention are useful as medicaments for the treatment or prophylaxis of diseases accompanying pain or inflammation (anti-pain agent, anti-inflammatory agent etc.).

Here, examples of the pain include nociceptive pain (muscular pain, back pain, upper limb pain, whiplash injury, arthralgia, osteoarthritis, gout, chronic rheumatoid arthritis, headache, migraine headache, catatonic headache, cluster headache, secondary headache, orofacial pain, toothache, causalgia after tooth extraction, phantom tooth pain, visceral pain, cardiac pain, abdominal pain, mittelschmerz, dysmenorrhea, labor pain, nephralgia, ureteralgia, ostalgia and the like), inflammatory pain, neuropathic pain (diabetic neuropathy, toxic neuropathy, pain after operation, phantom limb pain, stump pain, reflex sympathetic dystrophy, causalgia, postherpetic pain, trigeminal neuralgia, central pain), carcinomatous pain (pain due to cancer infiltration into visceral organ, pain caused by blood vessel obstruction due to blood vessel infiltration of cancer tissue, pain of bone metastasis, pain associated with intracerebral metastasis, pain caused by peripheral nerve infiltration of cancer tissue), fibromyalgia pain and the like.

While the disease associated with inflammation here is not particularly limited, systemic lupus erythematosus, multiple sclerosis, psoriasis, osteoarthritis, chronic rheumatoid arthritis, interstitial cystitis, asthma and the like can be mentioned.

While the above-mentioned cancer is not particularly limited, esophagus cancer, thyroid cancer, urinary bladder cancer, colorectal cancer, gastric cancer, pancreatic cancer, thoracic cancer, liver cancer, lung cancer, non-small cell lung cancer, breast cancer, neuroblastoma, neuroblastoma, glioblastoma, uterine cancer, cervical cancer, ovarian cancer, Wilms' tumor, prostate cancer and the like can be mentioned.

When NGF binds to a receptor thereof, TrkA, it activates tyrosine phosphorylation of TrkA and Ras-MAPK, PLC-γ, PI3K and the like at the downstream of TrkA, and exhibits physiological actions such as survival and differentiation of nerve cells. On the other hand, it induces cell death in the signal pathway via p75 receptor. Therefore, the aptamer and complex of the present invention can be used as medicaments, diagnostic agents, test drugs, or reagents for diseases relating to activation of these signal transduction pathways. Examples of the diseases relating to the activation of these signal transduction pathways include the above-mentioned pains and cancers.

When the aptamer and complex of the present invention are used as medicaments, diagnostic agents, test drugs, reagents and the like, the subject of administration of the aptamer is not particularly limited and, for example, primates (e.g., human, monkey), rodents (e.g., mouse, rat, guinea pig), and companion animals, domestic animals and working animals (e.g., dog, cat, horse, bovine, goat, sheep, swine) can be mentioned.

The aptamer and complex of the present invention are capable of binding specifically to NGF. Therefore, the aptamer and complex of the present invention are useful as probes for NGF detection. The probes are useful in in vivo imaging of NGF, measurements of blood concentrations, tissue staining, ELISA and the like. The probes are also useful as diagnostic agents, test drugs, reagents and the like for diseases involved by NGF (diseases accompanied by pain or inflammation, and the like).

Based on their specific binding to NGF, the aptamer and complex of the present invention can be used as ligands for purification of NGF.

In addition, the aptamer and complex of the present invention can be used as test drugs for examining the mental condition of romance and the like, or medicaments, regulators, enhancers or mitigators for controlling the mental condition.

The aptamer and complex of the present invention can be used as drug delivery vehicles.

The pharmaceutical of the present invention can be one formulated with a pharmaceutically acceptable carrier. As examples of the pharmaceutically acceptable carrier, excipients such as sucrose, starch, mannit, sorbit, lactose, glucose, cellulose, talc, calcium phosphate, and calcium carbonate; binders such as cellulose, methylcellulose, hydroxylpropylcellulose, polypropylpyrrolidone, gelatin, gum arabic, polyethylene glycol, sucrose, and starch; disintegrants such as starch, carboxymethylcellulose, hydroxylpropylstarch, sodium-glycol-starch, sodium hydrogen carbonate, calcium phosphate, and calcium citrate; lubricants such as magnesium stearate, Aerosil, talc, and sodium lauryl sulfate; flavoring agents such as citric acid, menthol, glycyrrhizin-ammonium salt, glycine, and orange powder; preservatives such as sodium benzoate, sodium hydrogen sulfite, methylparaben, and propylparaben; stabilizers such as citric acid, sodium citrate, and acetic acid; suspending agents such as methylcellulose, polyvinylpyrrolidone, and aluminum stearate; dispersing agents such as surfactants; diluents such as water, physiological saline, and orange juice; base waxes such as cacao butter, polyethylene glycol, and kerosene; and the like can be mentioned, but these are not limitative.

Preparations suitable for oral administration are a solution prepared by dissolving an effective amount of ligand in a diluent such as water, physiological saline, or orange juice; capsules, sachets or tablets comprising an effective amount of ligand in solid or granular form; a suspension prepared by suspending an effective amount of active ingredient in an appropriate dispersant; an emulsion prepared by dispersing and emulsifying a solution of an effective amount of active ingredient in an appropriate dispersant, and the like.

The pharmaceutical of the present invention can be coated by a method known per se for the purpose of taste masking, enteric dissolution, sustained release and the like. As examples of coating agents used for the coating, hydroxypropylmethylcellulose, ethylcellulose, hydroxymethylcellulose, hydroxypropylcellulose, polyoxyethylene glycol, Tween 80, Pluronic F68, cellulose acetate phthalate, hydroxypropylmethylcellulose phthalate, hydroxymethylcellulose acetate succinate, Eudragit (manufactured by Rohm, Germany, methacrylic acid/acrylic acid copolymer), pigments (e.g., ferric oxide red, titanium dioxide and the like) and the like are used. The pharmaceutical may be a rapid-release preparation or sustained-release preparation. Examples of sustained-release bases include liposome, atelocollagen, gelatin, hydroxyapatite, PLGA and the like.

As preparations suitable for parenteral administration (e.g., intravenous administration, subcutaneous administration, intramuscular administration, topical administration, intraperitoneal administration, intranasal administration, pulmonary administration and the like), aqueous and non-aqueous isotonic sterile injectable liquids are available, which may comprise an antioxidant, a buffer solution, a bacteriostatic agent, an isotonizing agent and the like. Aqueous and non-aqueous sterile suspensions can also be mentioned, which may comprise a suspending agent, a solubilizer, a thickener, a stabilizer, an antiseptic and the like. The preparation can be included in a container such as an ampoule or a vial in a unit dosage volume or in several divided doses. An active ingredient and a pharmaceutically acceptable carrier can also be freeze-dried and stored in a state that may be dissolved or suspended in an appropriate sterile vehicle just before use. Sustained-release preparations are also suitable preparations. The sustained-release preparations include sustained release from carriers or containers embedded in the body, such as artificial bones, biodegradable or non-degradable sponges, bags, drug pumps, osmotic pressure pumps and the like. Devices for continuous or intermittent, systemic or topical delivery from outside the body are also included in the scope of sustained-release preparations. Biodegradable bases include liposome, cationic liposome, Poly(lactic-co-glycolic) acid (PLGA), atherocollagen, gelatin, hydroxyapatite, polysaccharide sizofiran. In addition to liquid injections and sustained release preparation, inhalants and ointments are also acceptable. In the case of an inhalant, an active ingredient in a freeze-dried state is micronized and administered by inhalation using an appropriate inhalation device. An inhalant can be formulated as appropriate with a conventionally used surfactant, oil, seasoning, cyclodextrin or derivative thereof and the like as required.

Here, as examples of the surfactant, oleic acid, lecithin, diethylene glycol dioleate, tetrahydroflufuryl oleate, ethyl oleate, isopropyl myristate, glyceryl trioleate, glyceryl monolaurate, glyceryl monooleate, glyceryl monostearate, glyceryl monolysinoate, cetyl alcohol, stearyl alcohol, polyethyleneglycol 400, cetylpyridinium chloride, sorbitan trioleate (trade name, Span 85), sorbitan monooleate (trade name, Span 80), sorbitan monolaurate (trade name, Span 20), polyoxyethylene hardened castor oil (trade name, HCO-60), polyoxyethylene (20) sorbitan monolaurate (trade name, Tween 20), polyoxyethylene (20) sorbitan monooleate (trade name, Tween 80), lecithin of natural resource origin (trade name, EPICLON), oleylpolyoxyethylene (2) ether (trade name, Brij 92), stearyl polyoxyethylene (2) ether (trade name, Brij 72), lauryl polyoxyethylene (4) ether (trade name, Brij 30), oleylpolyoxyethylene (2) ether (trade name, Genapol 0-020), block copolymer of oxyethylene and oxypropylene (trade name, Synperonic) and the like can be mentioned. As examples of the oil, corn oil, olive oil, cottonseed oil, sunflower oil and the like can be mentioned. In the case of an ointment, an appropriate pharmaceutically acceptable base (yellow petrolatum, white petrolatum, paraffin, plastibase, silicone, white ointment, beeswax, lard, vegetable oils, hydrophilic ointment, hydrophilic petrolatum, purified lanolin, hydrolyzed lanolin, water-absorbing ointment, hydrophilic plastibase, macrogol ointment and the like) is blended with an active ingredient, and used as a preparation.

An inhalant can be produced according to a conventional method. Specifically, an inhalant can be produced by powdering or liquefying the above-described aptamer and complex of the present invention, blending it in an inhalation propellant and/or carrier, and filling them in an appropriate inhalation vessel. When the above-described aptamer and complex of the present invention is a powder, an ordinary mechanical powder inhalator can be used; in the case of a liquid, an inhalator such as a nebulizer can be used. Here, as the propellant, conventionally known one can be widely used; chlorofluorocarbon-series compounds such as chlorofluorocarbon-11, chlorofluorocarbon-12, chlorofluorocarbon-21, chlorofluorocarbon-22, chlorofluorocarbon-113, chlorofluorocarbon-114, chlorofluorocarbon-123, chlorofluorocarbon-142c, chlorofluorocarbon-134a, chlorofluorocarbon-227, chlorofluorocarbon-C318, and 1,1,1,2-tetrafluoroethane, hydrocarbons such as propane, isobutane, and n-butane, ethers such as diethyl ether, compressed gases such as nitrogen gas and carbon dioxide gas and the like can be mentioned.

The dosage of the pharmaceutical of the present invention varies depending on the kind and activity of active ingredient, seriousness of disease, animal species being the subject of administration, drug tolerability of the subject of administration, body weight, age and the like, and the usual dosage, based on the amount of active ingredient per day for an adult, can be about 0.0001 to about 100 mg/kg, for example, about 0.0001 to about 10 mg/kg, preferably about 0.005 to about 1 mg/kg.

The present invention also provides a solid phase carrier having the aptamer and the complex of the present invention immobilized thereon. As examples of the solid phase carrier, a substrate, a resin, a plate (e.g., multiwell plate), a filter, a cartridge, a column, and a porous material can be mentioned. The substrate can be one used in DNA chips, protein chips and the like; for example, nickel-PTFE (polytetrafluoroethylene) substrates, glass substrates, apatite substrates, silicon substrates, alumina substrates and the like, and substrates prepared by coating these substrates with a polymer and the like can be mentioned. As examples of the resin, agarose particles, silica particles, a copolymer of acrylamide and N,N'-methylenebisacrylamide, polystyrene-crosslinked divinylbenzene particles, particles of dextran crosslinked with epichlorohydrin, cellulose fiber, crosslinked polymers of aryldextran and N,N'-methylenebisacrylamide, monodispersed synthetic polymers, monodispersed hydrophilic polymers, Sepharose, Toyopearl and the like can be mentioned, and also resins prepared by binding various functional groups to these resins were included. The solid phase carrier of the present invention can be useful in, for example, purifying, detecting and quantifying NGF.

The aptamer and the complex of the present invention can be immobilized onto a solid phase carrier by a method known per se. For example, a method that introduces an affinity substance (e.g., those described above) or a predetermined functional group into the aptamer or the complex of the present invention, and then immobilizes the aptamer and complex onto a solid phase carrier via the affinity substance or predetermined functional group can be mentioned. The present invention also provides such methods. The predetermined functional group can be a functional group that can be subjected to a coupling reaction; for example, an amino group, a thiol group, a hydroxyl group, and a carboxyl group can be mentioned. The present invention also provides an aptamer having such a functional group introduced thereto.

The present invention also provides a method of purifying and concentrating NGF. In particular, the present invention makes it possible to separate NGF from the proteins of other family proteins. The method of purification and concentration of the present invention can comprise adsorbing NGF to the solid phase carrier of the present invention, and eluting the adsorbed NGF with an eluent. Adsorption of NGF to the solid phase carrier of the present invention can be achieved by a method known per se. For example, a NGF-containing sample (e.g., bacterial or cell culture or culture supernatant, blood) is introduced into the solid phase carrier of the present invention or a composition containing the same. NGF can be eluted using an eluent such as a neutral solution. There is no limitation on the neutral eluent, which can have a pH of, for example, about 6 to about 9, preferably about 6.5 to about 8.5, and more preferably about 7 to about 8. The neutral solution can also comprise, for example, urea, a chelating agent (e.g., EDTA), a potassium salt (e.g., KCl), a magnesium salt (e.g., $MgCl_2$), a surfactant (e.g., Tween 20, Triton, NP40), and glycerin. The method of purification and concentration of the present invention can further comprise washing the solid phase carrier using a washing solution after NGF adsorption. Examples of the washing solution include those containing urea, a chelating agent (e.g., EDTA), Tris, an acid, an alkali, Transfer RNA, DNA, surfactants such as Tween 20, salts such as NaCl and the like. The method of purification and concentration of the present invention can still further comprise heating the solid phase carrier. This step enables the regeneration and sterilization of the solid phase carrier.

The present invention also provides a method of detecting and quantifying NGF. In particular, the present invention makes it possible to detect and quantify NGF separately from the proteins of other family proteins. The method of detection and quantitation of the present invention can comprise measuring NGF by utilizing the aptamer of the present invention (e.g., by the use of the complex and solid phase carrier of the present invention). The method of detecting and quantifying NGF can be performed in the same manner as an immunological method, except that the aptamer of the present invention is used in place of an antibody. Therefore, by using the aptamer of the present invention as a probe in place of an antibody, in the same manner as such methods as enzymeimmunoassay (EIA) (e.g., direct competitive ELISA, indirect competitive ELISA, sandwich ELISA), radioimmunoassay (RIA), fluorescent immunoassay (FIA), Western blot technique, immunohistochemical staining method, and cell sorting method, detection and quantitation can be performed. The aptamer of the present invention can also be used as a molecular probe for PET and the like. These methods can be useful in, for example, measuring NGF contents in living organisms or biological samples, and in diagnosing a disease associated with NGF.

The disclosures in all publications mentioned herein, including patents and patent application specifications, are

19 incorporated by reference herein in the present invention to the extent that all of them have been given expressly.

EXAMPLES

The present invention is hereinafter described in more detail by means of the following Examples, which, however, never limit the scope of the invention.

Example 1

Preparation of RNA Aptamers that Bind Specifically to NGF 1

RNA aptamers that bind specifically to NGF were prepared using the SELEX method. The SELEX was performed by reference to the method of Ellington et al. (Ellington and Szostak, Nature 346, 818-822, 1990) and the method of Tuerk et al. (Tuerk and Gold, Science 249, 505-510, 1990). Human NGF (manufactured by R&D Systems) was used as a target substance.

The RNA used in the first round (40N-RNA) was obtained by transcribing a chemically synthesized DNA using the DuraScribe™ T7 Transcription Kit (manufactured by Epicentre). The RNA obtained by this method has the 2'-position of the ribose of the pyrimidine nucleotide fluoro-replaced. The DNA 79 nucleotides long shown below, having a primer sequence at each end of a 40-nucleotide random sequence was used as DNA template. The DNA template and the primers were prepared by chemical synthesis.

```
DNA template:
                                    (SEQ ID NO: 114)
5'-ccagttgttggtgacaatgc-40N-gcagctccacaggcttccc-3' primer Fwd:
                                    (SEQ ID NO: 115)
5'-taatacgactcactatagggaagcctgtggagctgc-3' primer Rev:
                                    (SEQ ID NO: 116)
5'-ccagttgttggtgacaatgc-3'
```

N represents any one of A, G, C and T. The primer Fwd comprises a promoter sequence of T7 RNA polymerase. The variation of the RNA pool used in the first round was theoretically $10^{14}$.

After 10 rounds of SELEX, the sequences were sequenced; sequence convergence was seen. In 48 clones, 6 sequences shown by SEQ ID NO: 1, and 5 sequences shown by SEQ ID NO: 2 were present. Three sequences shown by SEQ ID NOs: 3-5, and two sequences shown by SEQ ID NOs: 6-8 were present. Only one sequence was shown by SEQ ID NOs: 9-23. Many sequences contained a consensus sequence of UGAAAAAAACC (SEQ ID NO: 91). The secondary structures of these sequences were predicted using the MFOLD program (M. Zuker, Nucleic Acids Res. 31(13), 3406-3415, 2003) and bulge structures having similar consensus sequence portions were predicted. Putative secondary structures of the aptamers of the sequences shown by SEQ ID NOs: 1-9 and 12 are given in FIGS. 1-10, wherein the consensus sequences are enclosed in a circle.

The nucleotide sequences actually obtained, which correspond to each SEQ ID NO, are shown below. The parentheses in each nucleotide show modifications at the 2'-position and F is fluorine atom (hereinafter the same).

20

```
SEQ ID NO: 1:
gggaagc(F)c(F)u(F)gu(F)ggagc(F)u(F)gc(F)aggau(F)ga
aaaaaac(F)c(F)c(F)aaaaac(F)aaagac(F)aau(F)gau(F)u
(F)gagu(F)agc(F)au(F)u(F)gu(F)c(F)ac(F)c(F)aac(F)a
ac(F)u(F)gg SEQ ID NO: 2:
gggaagc(F)c(F)u(F)gu(F)ggagc(F)u(F)gc(F)c(F)u(F)ac
(F)ac(F)u(F)u(F)u(F)agu(F)au(F)gac(F)aaac(F)c(F)u
(F)agagu(F)gu(F)aaau(F)gc(F)u(F)u(F)c(F)gc(F)au(F)
u(F)gu(F)c(F)ac(F)c(F)aac(F)aac(F)u(F)gg SEQ ID NO: 3:
gggaagc(F)c(F)u(F)gu(F)ggagc(F)u(F)gc(F)aggau(F)ga
aaaaaac(F)cF)c(F)aaaau(F)aagu(F)agaaau(F)gac(F)aga
au(F)ggc(F)au(F)u(F)gu(F)c(F)ac(F)c(F)aac(F)aac(F)
u(F)gg SEQ ID NO: 4:
gggaagc(F)c(F)u(F)gu(F)ggagc(F)u(F)gc(F)aggau(F)ga
gaaaaaac(F)c(F)c(F)aaau(F)au(F)gac(F)aaau(F)aaaac
(F)ggc(F)aac(F)gc(F)au(F)u(F)gu(F)c(F)ac(F)c(F)aac
(F)aac(F)u(F)gg SEQ ID NO: 5:
gggaagc(F)c(F)u(F)gu(F)ggagc(F)u(F)gc(F)u(F)u(F)aa
ac(F)aagc(F)aagu(F)gaaaaaaac(F)c(F)ac(F)agc(F)aaau
(F)gu(F)aaaaagc(F)au(F)u(F)gu(F)c(F)ac(F)c(F)aac
(F)aac(F)u(F)gg SEQ ID NO: 6:
gggaagc(F)c(F)u(F)gu(F)ggagc(F)u(F)gc(F)aggau(F)ga
aaaaaac(F)c(F)c(F)aaaau(F)u(F)aaau(F)aaaaaau(F)aga
c(F)ggu(F)gc(F)au(F)u(F)gu(F)c(F)ac(F)c(F)aac(F)aa
c(F)u(F)gg SEQ ID NO: 7:
gggaagc(F)c(F)u(F)gu(F)ggagc(F)u(F)gc(F)aggau(F)ga
aaaaaac(F)c(F)c(F)aaaau(F)u(F)agau(F)aaaaaau(F)aga
c(F)ggu(F)gc(F)au(F)u(F)gu(F)c(F)ac(F)c(F)aac(F)aa
c(F)u(F)gg SEQ ID NO: 8:
gggaagc(F)c(F)u(F)gu(F)ggagc(F)u(F)gc(F)ggau(F)aaa
aau(F)agagu(F)u(F)u(F)gau(F)aaac(F)ac(F)c(F)u(F)gu
(F)au(F)u(F)aaaac(F)c(F)gc(F)au(F)u(F)gu(F)c(F)ac
(F)c(F)aac(F)aac(F)u(F)gg SEQ ID NO: 9:
gggaagc(F)c(F)u(F)gu(F)ggagc(F)u(F)gc(F)u(F)c(F)c
(F)ac(F)aaggau(F)gaaaaaaac(F)c(F)c(F)aaau(F)aau(F)
au(F)au(F)u(F)u(F)aau(F)c(F)agc(F)au(F)u(F)gu(F)c
(F)ac(F)c(F)aac(F)aac(F)u(F)gg SEQ ID NO: 10:
gggaagc(F)c(F)u(F)gu(F)ggagc(F)u(F)gc(F)aggau(F)ga
aaaaaac(F)c(F)c(F)aaau(F)u(F)aaagagc(F)u(F)u(F)gac
(F)aaaac(F)au(F)gc(F)au(F)u(F)gu(F)c(F)ac(F)c(F)aa
c(F)aac(F)u(F)gg SEQ ID NO: 11:
gggaagc(F)c(F)u(F)gu(F)ggagc(F)u(F)gc(F)u(F)c(F)c
(F)ac(F)aaggau(F)gaaaaaaac(F)c(F)c(F)aaau(F)aau
(F)au(F)au(F)u(F)aau(F)c(F)agc(F)au(F)u(F)gu
(F)c(F)ac(F)c(F)aac(F)aac(F)u(F)gg SEQ ID NO: 12:
gggaagc(F)c(F)u(F)gu(F)ggagc(F)u(F)gc(F)gaaac(F)ag
u(F)gaaac(F)aaac(F)c(F)ac(F)agac(F)u(F)gagaaagc(F)
agu(F)aac(F)agc(F)au(F)u(F)gu(F)c(F)ac(F)c(F)aac
(F)aac(F)u(F)gg SEQ ID NO: 13:
gggaagc(F)c(F)u(F)gu(F)ggagc(F)u(F)gc(F)aggau(F)ga
aaaaaac(F)c(F)c(F)aaaau(F)u(F)aaau(F)aaaaaaaau(F)
ggac(F)ggu(F)gc(F)au(F)u(F)gu(F)c(F)ac(F)c(F)
aac(F)aac(F)u(F)gg
```

-continued

Figure 11:
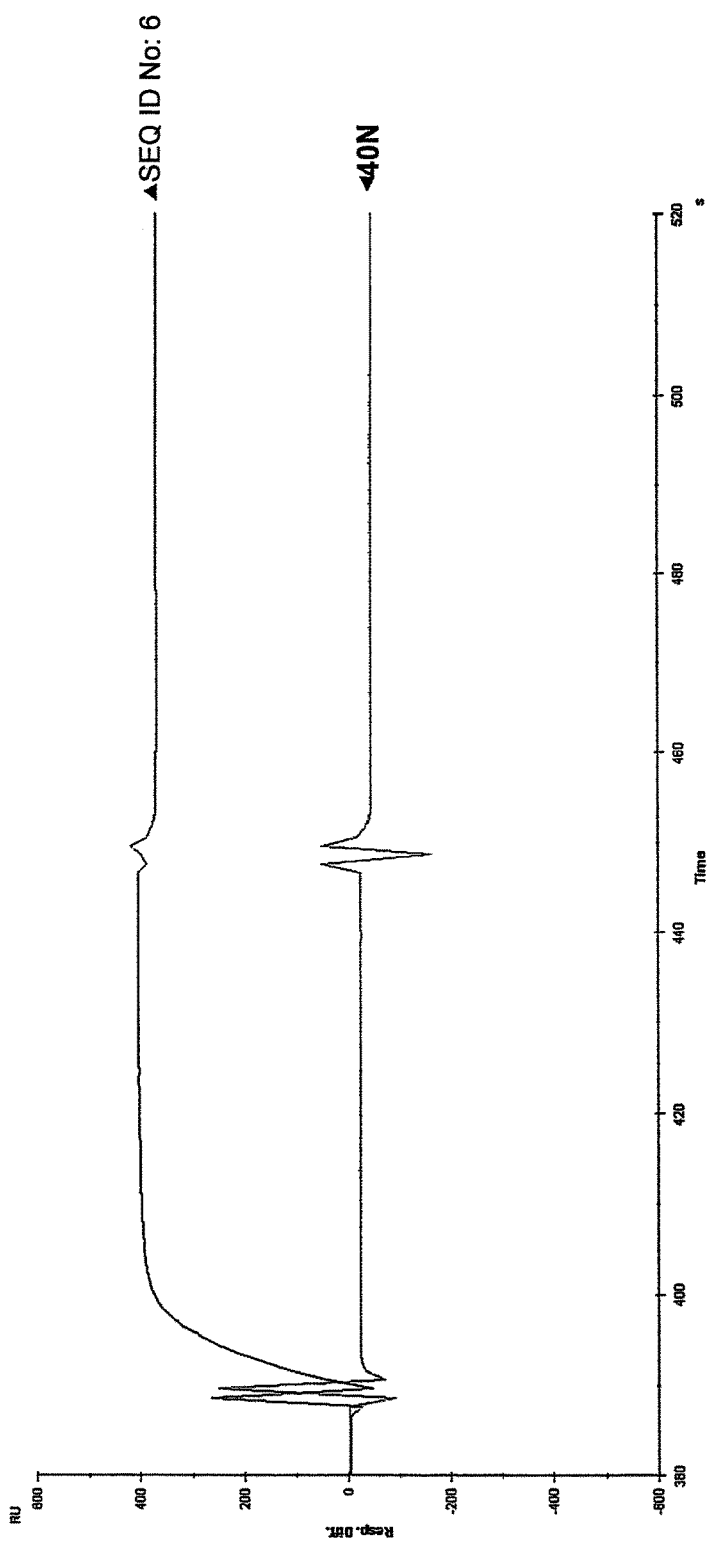
FIG. 11 is a sensorgram showing that the aptamer (Apt) shown by SEQ ID NO: 6 binds to human NGF, wherein 40N is an RNA containing a random sequence with 40 nucleotides. Using, as a ligand, Apt or 40N as a negative control, and human NGF as an analyte, the measurement was performed by BIAcore2000 manufactured by BIAcore.

SEQ ID NO: 14:
gggaagc(F)c(F)u(F)gu(F)ggagc(F)u(F)gc(F)u(F)gaau
(F)u(F)ggau(F)ac(F)agau(F)agu(F)u(F)gaaaaaaac(F)c
(F)aau(F)gau(F)c(F)agc(F)au(F)u(F)gu(F)c(F)ac(F)c
(F)aac(F)aac(F)u(F)gg SEQ ID NO: 15:
gggaagc(F)c(F)u(F)gu(F)ggagc(F)u(F)gc(F)u(F)c(F)c
(F)ac(F)aaggau(F)gaaaaaaac(F)c(F)c(F)aaau(F)aau(F)
au(F)au(F)u(F)u(F)gau(F)c(F)agc(F)au(F)u(F)gu(F)c
(F)ac(F)c(F)aac(F)aac(F)u(F)gg SEQ ID NO: 16:
gggaagc(F)c(F)u(F)gu(F)ggagc(F)u(F)gc(F)u(F)c(F)c
(F)ac(F)aaggau(F)gaaaaaaac(F)c(F)c(F)c(F)aaau(F)aa
u(F)gu(F)au(F)u(F)u(F)aau(F)c(F)agc(F)au(F)u(F)gu
(F)c(F)ac(F)c(F)aac(F)aac(F)u(F)gg SEQ ID NO: 17:
gggaagc(F)c(F)u(F)gu(F)ggagc(F)u(F)gc(F)aggau(F)gg
aaaaaac(F)c(F)c(F)aaau(F)aagu(F)agaaau(F)gac(F)ag
aau(F)ggc(F)au(F)u(F)gu(F)c(F)ac(F)c(F)aac(F)aac
(F)u(F)gg SEQ ID NO: 18:
gggaagc(F)c(F)u(F)gu(F)ggagc(F)u(F)gc(F)c(F)gaaau
(F)ggac(F)u(F)gu(F)aaagc(F)au(F)gaaaaaaac(F)c(F)au
(F)u(F)c(F)aau(F)c(F)gaggc(F)au(F)u(F)gu(F)c(F)ac
(F)c(F)aac(F)aac(F)u(F)gg SEQ ID NO: 19:
gggaagc(F)c(F)u(F)gu(F)ggagc(F)u(F)gc(F)aggau(F)ga
aaaaaac(F)c(F)c(F)aaac(F)u(F)aaagu(F)u(F)u(F)aaaac
(F)u(F)gau(F)ac(F)gagc(F)au(F)u(F)gu(F)c(F)ac(F)c
(F)aac(F)aac(F)u(F)gg SEQ ID NO: 20:
gggaagc(F)c(F)u(F)gu(F)ggagc(F)u(F)gc(F)aggau(F)ga
aaaaaac(F)c(F)c(F)aaau(F)u(F)aaaac(F)u(F)u(F)gc
(F)c(F)gagc(F)au(F)u(F)gu(F)c(F)ac(F)c(F)aac(F)aac
(F)u(F)gg SEQ ID NO: 21:
gggaagc(F)c(F)u(F)gu(F)ggagc(F)u(F)gc(F)aggau(F)ga
aaaaaaac(F)c(F)c(F)aaaac(F)aaagac(F)aac(F)gau(F)u
(F)gagu(F)agc(F)au(F)u(F)gu(F)c(F)ac(F)c(F)aac(F)
aac(F)u(F)gg SEQ ID NO: 22:
gggaagc(F)c(F)u(F)gu(F)ggagc(F)u(F)gc(F)aggau(F)ga
aaaaaac(F)c(F)c(F)aaau(F)u(F)gu(F)c(F)c(F)ac(F)ag
aaaau(F)ggau(F)u(F)gc(F)au(F)u(F)gu(F)c(F)ac(F)c
(F)aac(F)aac(F)u(F)gg SEQ ID NO: 23:
gggaagc(F)c(F)u(F)gu(F)ggagc(F)u(F)gc(F)gaaac(F)ag
u(F)gaaac(F)aaac (F)c(F)ac(F)agac(F)u (F)gagaaagc
(F)agu(F)aaaagc(F)au(F)u(F)gu(F)c(F)ac(F)c(F)aac
(F)aac(F)u(F)gg The binding activities for NGF of the nucleic acids shown by SEQ ID NOs:1-9 and 12 were evaluated by the surface plasmon resonance method. The measurements were taken using BIAcore 2000 (manufactured by BIAcore). The SA chip was used as the sensor chip, which had streptavidin immobilized thereon. Bound thereto was about 1500 RU of a 16-nucleotide Poly dT with biotin bound to the 5' end thereof. The ligand nucleic acid had a 16-nucleotide Poly A added to the 3' end thereof, and was immobilized on the SA chip via a bond between T and A. The amount immobilized was about 1000 RU. 20 μL of NGF for analyte, prepared at 0.5 μM, was injected, with the addition of a final concentration of 0.3M NaCl to lessen nonspecific adsorption. Solution A was used as a running buffer. Here, solution A is a mixed solution of 145 mM sodium chloride, 5.4 mM potassium chloride, 1.8 mM calcium chloride, 0.8 mM magnesium chloride, 20 mM Tris (pH 7.6), and 0.05% Tween 20. As a result of the measurement, it was found that all of the nucleic acids shown by SEQ ID NOs:1-9 and 12 bind to NGF significantly more than the control 40N. Here, 40N refers to the nucleic acid pool used for the first round, comprising a 40-nucleotide random sequence. As an example, a sensorgram showing a status of the binding of the aptamer shown by SEQ ID NO:6 and NGF is shown in FIG. 11. From the above, it was shown that these nucleic acids are aptamers that bind to NGF.

Example 2

Preparation of RNA Aptamers that Bind Specifically to NGF 2

SELEX was performed in the same manner as in Example 1 except that a template having a 30 nucleotide random sequence and primer sequences different from those used in Example 1 were used. The template and the primer sequences used are shown below. As the template, a 30 nucleotide random sequence was used. The DNA template and primers were produced by chemical synthesis.

DNA template:
(SEQ ID NO: 117)
5'-tgaggatccatgtatgcgcacata-30N-cttctggtcgaagtt
ctccc-3' primer Fwd:
(SEQ ID NO: 118)
5'-cggaattctaatacgactcactatagggagaacttcgaccagaa
g-3' primer Rev:
(SEQ ID NO: 119)
5'-tgaggatccatgtatgcgcacata-3'

After 13 rounds of SELEX, the sequences were sequenced. Although sequence convergence was not seen yet, many sequences contained a consensus sequence of UGAAAAAAACC (SEQ ID NO: 91). In addition, some sequences contained mutation in the consensus sequence of UGAAAAAAACC (SEQ ID NO: 91) such as UGAAAGAAACC (SEQ ID NO: 92), UGAAAAGAACC (SEQ ID NO: 95), UGAAAGGAACC (SEQ ID NO: 105) and the like.

While the primary sequence is somewhat different, AGAAUGAAACU (SEQ ID NO: 102) was present as a sequence expected to have a similar bulge structure by the MFOLD program.

A subset of these sequences is shown by SEQ ID NOs: 37-42.

After 16 rounds of SELEX, the sequences were sequenced again. Convergence of other sequences was not seen but two sequences shown by SEQ ID NOs: 43 and 51 were present. Many of these sequences contained, like the sequences after 13 rounds, the consensus sequence of UGAAAAAAACC (SEQ ID NO: 91). In addition, some sequences contained mutation in the consensus sequence of UGAAAAAAACC (SEQ ID NO: 91) such as UGAAAGAAACC (SEQ ID NO: 92), UGAAACAAACC (SEQ ID NO: 94), UGAAAAGAACC (SEQ ID NO: 95), UGAAAGGAACC (SEQ ID NO: 105), UGAAAAAACCU (SEQ ID NO: 97), and the like.

A subset of these sequences is shown by SEQ ID NOs: 43-53.

After 19 rounds of SELEX, the sequences were sequenced again. Although 3 sequences shown by SEQ ID NO: 56 and 2 sequences shown by each of SEQ ID NOs: 54, 57 and 67 were present, convergence of other sequences was not seen yet. Many of these sequences contained a consensus sequence such as UGAAAAAAACC (SEQ ID NO: 91), UGAAAGAAACC (SEQ ID NO: 92) and UGAAAAGAACC (SEQ ID NO: 95).

A subset of these sequences is shown by SEQ ID NOs: 54-59.

After 22 rounds of SELEX, the sequences were sequenced again. 6 sequences shown by SEQ ID NO: 67 and 3 sequences shown by SEQ ID NO: 68 were present. These sequences contained sequences of CGAACAAAACU (SEQ ID NO: 103) and CGAAAGAAACU (SEQ ID NO: 104) similar to the consensus sequence shown by SEQ ID NO: 91. Convergences of other sequences was not seen, but many sequences contained the consensus sequences of UGAAAAAAACC (SEQ ID NO: 91) and UGAAAGAAACC (SEQ ID NO: 92).

A subset of these sequences is shown by SEQ ID NOs: 60-68.

The nucleotide sequences actually obtained which correspond to SEQ ID NOs mentioned above are shown below. The parentheses in the nucleotides show the modification at the 2'-position and F is a fluorine atom.

```
SEQ ID NO: 37:
gggagaac(F)u(F)u(F)c(F)gac(F)c(F)agaagu(F)u(F)
(F)gaaagaaac(F)c(F)c(F)aaaggu(F)gaaac(F)aac(F)a
au(F)au(F)gu(F)gc(F)gc(F)au(F)ac(F)au(F)ggau(F)
c(F)c(F)u(F)c(F)a SEQ ID NO: 38:
gggagaac(F)u(F)u(F)c(F)gac(F)c(F)agaagagaau(F)g
aaac(F)u(F)c(F)c(F)ac(F)aaagu(F)ac(F)au(F)aaaac
(F)au(F)au(F)gu(F)gc(F)gc(F)au(F)ac(F)au(F)ggau
(F)c(F)c(F)u(F)c(F)a SEQ ID NO: 39:
gggagaac(F)u(F)u(F)c(F)gac(F)c(F)agaagu(F)gu(F)
gaaaagaac(F)c(F)c(F)aaau(F)aaaac(F)aac(F)aau(F)
gu(F)au(F)gu(F)gc(F)gc(F)au(F)ac(F)au(F)ggau(F)
c(F)c(F)u(F)c(F)a SEQ ID NO: 40:
gggagaac(F)u(F)u(F)c(F)gac(F)c(F)agaagu(F)u(F)
(F)gaaaaaac(F)c(F)c(F)aggaaaau(F)ggaagac(F)gu
(F)au(F)gu(F)gc(F)gc(F)au(F)ac(F)au(F)ggau(F)c
(F)c(F)u(F)c(F)a SEQ ID NO: 41:
gggagaac(F)u(F)u(F)c(F)gac(F)c(F)agaagu(F)u(F)
(F)gaaaggaac(F)c(F)c(F)aaagc(F)gaaac(F)aaaac(F)
gu(F)au(F)gu(F)gc(F)gc(F)au(F)ac(F)au(F)ggau(F)
c(F)c(F)u(F)c(F)a SEQ ID NO: 42:
gggagaac(F)u(F)u(F)c(F)gac(F)c(F)agaagu(F)u(F)u
(F)gaaaaaac(F)c(F)c(F)aaaagagc(F)agc(F)agagau
(F)au(F)gu(F)gc(F)gc(F)au(F)ac(F)au(F)ggau(F)c
(F)c(F)u(F)c(F)a SEQ ID NO: 43:
gggagaac(F)u(F)u(F)c(F)gac(F)c(F)agaagc(F)u(F)u
(F)gaaaaaac(F)c(F)c(F)c(F)aau(F)au(F)gagaau(F)c
(F)au(F)au(F)au(F)gu(F)gc(F)gc(F)au(F)ac(F)au
(F)ggau(F)c(F)c(F)u(F)c(F)a SEQ ID NO: 44:
gggagaac(F)u(F)u(F)c(F)gac(F)c(F)agaagu(F)u(F)u
(F)gaaagaaac(F)c(F)c(F)aaaau(F)u(F)agc(F)ac(F)c
(F)au(F)aau(F)au(F)gu(F)gc(F)gc(F)au(F)ac(F)au
(F)ggau(F)c(F)c(F)u(F)c(F)a SEQ ID NO: 45:
gggagaac(F)u(F)u(F)c(F)gac(F)c(F)agaagagaau(F)g
aaac(F)u(F)c(F)c(F)c(F)aaau(F)c(F)aaggac(F)aau
(F)gau(F)au(F)gu(F)gc(F)gc(F)au(F)ac(F)au(F)gga
u(F)c(F)c(F)u(F)c(F)a SEQ ID NO: 46:
gggagaac(F)u(F)u(F)c(F)gac(F)c(F)agaagu(F)u(F)u
(F)gaaac(F)aaac(F)c(F)c(F)aaagu(F)u(F)ac(F)gc
(F)ac(F)aaaau(F)au(F)gu(F)gc(F)gc(F)au(F)ac(F)a
u(F)ggau(F)c(F)c(F)u(F)c(F)a SEQ ID NO: 47:
gggagaac(F)u(F)u(F)c(F)gac(F)c(F)agaagaagu(F)u
(F)u(F)gaaaagaac(F)c(F)c(F)aaaau(F)gagc(F)aaaau
(F)au(F)gu(F)gc(F)gc(F)au(F)ac(F)au(F)ggau(F)c
(F)c(F)u(F)c(F)a SEQ ID NO: 48:
gggagaac(F)u(F)u(F)c(F)gac(F)c(F)agaagu(F)u(F)u
(F)gaaaagaac(F)c(F)c(F)gaaaaac(F)gc(F)au(F)aau
(F)aau(F)au(F)gu(F)gc(F)gc(F)au(F)ac(F)au(F)gga
u(F)c(F)c(F)u(F)c(F)a SEQ ID NO: 49:
gggagaac(F)u(F)u(F)c(F)gac(F)c(F)agaagu(F)gaaag
aaac(F)u(F)c(F)c(F)c(F)aagac(F)ggu(F)aac(F)gaaa
gu(F)au(F)gu(F)gc(F)gc(F)au(F)ac(F)au(F)ggau(F)
c(F)c(F)u(F)c(F)a SEQ ID NO: 50:
gggagaac(F)u(F)u(F)c(F)gac(F)c(F)agaagu(F)gaaaa
aac(F)c(F)u(F)c(F)c(F)c(F)aau(F)ac(F)aaac(F)ac
(F)aaaaau(F)au(F)gu(F)gc(F)gc(F)au(F)ac(F)au(F)
ggau(F)c(F)c(F)u(F)c(F)a SEQ ID NO: 51:
gggagaac(F)u(F)u(F)c(F)gac(F)c(F)agaagu(F)u(F)u
(F)gaaagaaac(F)c(F)c(F)aaaaaaac(F)aac(F)au(F)au
(F)gaac(F)u(F)au(F)gu(F)gc(F)gc(F)au(F)ac(F)au
(F)ggau(F)c(F)c(F)u(F)c(F)a SEQ ID NO: 52:
gggagaac(F)u(F)u(F)c(F)gac(F)c(F)agaagu(F)u(F)u
(F)gaaagaaac(F)c(F)c(F)aaau(F)au(F)ac(F)aaaac
(F)ac(F)u(F)au(F)gu(F)gc(F)gc(F)au(F)ac(F)au(F)
ggau(F)c(F)c(F)u(F)c(F)a SEQ ID NO: 53:
gggagaac(F)u(F)u(F)c(F)gac(F)c(F)agaagu(F)u(F)u
(F)gaaaggaac(F)c(F)c(F)aaaaac(F)ac(F)aaaau(F)gu
(F)c(F)u(F)au(F)gu(F)gc(F)gc(F)au(F)ac(F)au(F)g
gau(F)c(F)c(F)u(F)c(F)a SEQ ID NO: 54:
gggagaac(F)u(F)u(F)c(F)gac(F)c(F)agaagu(F)c(F)g
aaagu(F)gaaagaaac(F)u(F)c(F)c(F)aac(F)gaaagc(F)
au(F)au(F)gu(F)gc(F)gc(F)au(F))ac(F)au(F)ggau
(F)c(F)c(F)u(F)c(F)a SEQ ID NO: 55:
gggagaac(F)u(F)u(F)c(F)gac(F)c(F)agaagu(F)u(F)u
(F)gaaagaaac(F)c(F)c(F)aaaaau(F)gaau(F)gc(F)aac
(F)u(F)au(F)gu(F)gc(F)au(F)ac(F)au(F)ggac
(F)c(F)u(F)c(F)a SEQ ID NO: 56:
gggagaac(F)u(F)u(F)c(F)gac(F)c(F)agaagu(F)gaaag
aaac(F)u(F)c(F)c(F)c(F)aac(F)ac(F)aaau(F)gc(F)a
c(F)aac(F)u(F)au(F)gu(F)gc(F)gc(F)au(F)ac(F)au
(F)ggau(F)c(F)c(F)u(F)c(F)a SEQ ID NO: 57:
gggagaac(F)u(F)u(F)c(F)gac(F)c(F)agaagu(F)u(F)u
(F)gaaaaaac(F)c(F)c(F)aaac(F)ac(F)c(F)gaagc(F)
ac(F)aaau(F)au(F)gu(F)gc(F)gc(F)au(F)ac(F)au(F)
ggau(F)c(F)c(F)u(F)c(F)a
```

```
SEQ ID NO: 58:
gggagaac(F)u(F)u(F)c(F)gac(F)c(F)agaagu(F)u(F)u
(F)gaaaagaac(F)c(F)c(F)aaau(F)ac(F)agaau(F)aaau
(F)gu(F)au(F)gu(F)gc(F)gc(F)au(F)ac(F)au(F)ggau
(F)c(F)c(F)u(F)c(F)a SEQ ID NO: 59:
gggagaac(F)u(F)u(F)c(F)gac(F)c(F)agaagu(F)c(F)g
aaac(F)gu(F)u(F)u(F)gaaaaaaac(F)c(F)c(F)aaggagg
au(F)au(F)gu(F)gc(F)gc(F)au(F)ac(F)au(F)ggau(F)
c(F)c(F)u(F)c(F)a SEQ ID NO: 60:
gggagaac(F)u(F)u(F)c(F)gac(F)c(F)agaagu(F)u(F)
u(F)gaaaaaaac(F)c(F)c(F)gaau(F)aaagau(F)aac(F)a
gu(F)au(F)gu(F)gc(F)gc(F)au(F)ac(F)au(F)ggau(F)
c(F)c(F)u(F)c(F)a SEQ ID NO: 61:
gggagaac(F)u(F)u(F)c(F)gac(F)c(F)agaaggu(F)c(F)
gu(F)aac(F)gaau(F)aaaac(F)u(F)c(F)c(F)u(F)gc(F)
ac(F)aaaaau(F)au(F)gu(F)gc(F)gc(F)au(F)ac(F)au
(F)ggau(F)c(F)c(F)u(F)c(F)a SEQ ID NO: 62:
gggagaac(F)u(F)u(F)c(F)gac(F)c(F)agaagu(F)u(F)u
(F)gaaagaac(F)c(F)c(F)aaau(F)u(F)aaagu(F)gaac
(F)agu(F)au(F)gu(F)gc(F)gc(F)au(F)ac(F)au(F)gga
u(F)c(F)c(F)u(F)c(F)a SEQ ID NO: 63:
gggagaac(F)u(F)u(F)c(F)gac(F)c(F)agaagau(F)u(F)
u(F)gaaagaaac(F)c(F)c(F)aaac(F)u(F)aagc(F)ac(F)
aaaau(F)au(F)gu(F)gc(F)gc(F)au(F)ac(F)au(F)ggau
(F)c(F)c(F)u(F)c(F)a SEQ ID NO: 64:
gggagaac(F)u(F)u(F)c(F)gac(F)c(F)agaagu(F)u(F)u
(F)gaaagaaac(F)c(F)c(F)aaaac(F)au(F)u(F)agc(F)a
c(F)ac(F)au(F)au(F)gu(F)gc(F)gc(F)au(F)ac(F)au
(F)ggau(F)c(F)c(F)u(F)c(F)a SEQ ID NO: 65:
gggagaac(F)u(F)u(F)c(F)gac(F)c(F)agaagu(F)gu(F)
gaaaaaaac(F)c(F)c(F)aaau(F)c(F)gagc(F)ac(F)aaaa
u(F)u(F)au(F)gu(F)gc(F)gc(F)au(F)ac(F)au(F)ggau
(F)c(F)c(F)u(F)c(F)a SEQ ID NO: 66:
gggagaac(F)u(F)u(F)c(F)gac(F)c(F)agaagu(F)u(F)u
(F)gaaaaaaac(F)c(F)c(F)aaagc(F)aagc(F)ac(F)aac
(F)au(F)u(F)au(F)gu(F)gc(F)gc(F)au(F)ac(F)au(F)
ggau(F)c(F)c(F)u(F)c(F)a SEQ ID NO: 67:
gggagaac(F)u(F)u(F)c(F)gac(F)c(F)agaagu(F)c(F)g
au(F)aac(F)gaac(F)aaaac(F)u(F)c(F)c(F)c(F)aaagg
aau(F)au(F)au(F)gu(F)gc(F)gc(F)au(F)ac(F)au(F)g
gau(F)c(F)c(F)u(F)c(F)a SEQ ID NO: 68:
gggagaac(F)u(F)u(F)c(F)gac(F)c(F)agaagu(F)c(F)g
agagc(F)gaaagaac(F)u(F)c(F)c(F)c(F)aaaac(F)ac
(F)agu(F)au(F)gu(F)gc(F)gc(F)au(F)ac(F)au(F)gga
u(F)c(F)c(F)u(F)c(F)a
```

The binding activities for NGF of the nucleic acids shown by SEQ ID NOs: 37-68 were evaluated by the surface plasmon resonance method. A method similar to that shown in Example 1 was used for the experiment. As a result, all the sequences were found to bind more significantly to NGF than 30N of the control.

Example 3

Preparation of RNA-DNA Mosaic Aptamer that Binds Specifically to NGF

Mosaic aptamer wherein RNA is purine nucleotide and DNA is pyrimidine nucleotide was produced according to the SELEX method. The template used contained a 40 nucleotide random sequence and the primers used were different from those used in Examples 1 and 2. The pool of RNA-DNA mosaic nucleic acid used in the first round was obtained by transcribing chemically synthesized DNA as a template, and rATP, rGTP, dCTP and dTTP as substrates. Here, rNTP is ribonucleotide, and dNTP is deoxyribonucleotide. Other experiment methods are almost the same as those shown in Example 1. The template and primer sequences used are shown below.

```
DNA-RNA template:
                                    (SEQ ID NO: 120)
5'-tcctaatgtctcttctcttcac-40N-gccctattcttgcctct
ccc-3' primer Fwd:
                                    (SEQ ID NO: 121)
5'-taatacgactcactatagggagaggcaagaatagggc-3' primer Rev:
                                    (SEQ ID NO: 122)
5'-tcctaatgtctcttctcttcac-3'
```

After 7 rounds of SELEX, the sequences were sequenced. Sequence convergence was not seen, but many sequences contained the consensus sequence of TGAAAAAAACC (SEQ ID NO: 91). After 10 rounds of SELEX, the sequences were sequenced again. Six sequences shown by SEQ ID NO: 72, 5 sequences shown by each of SEQ ID NOs: 70 and 71, and 2 sequences shown by SEQ ID NOs: 69 and 73 were present. In addition, 22 sequences were found only once (including a sequence shown by SEQ ID NO: 74), many of which contained the consensus sequence of TGAAAAAAACC (SEQ ID NO: 91).

The nucleotide sequences actually obtained, which correspond to SEQ ID NOs: 69-74, are shown below. T and C in capital letters show deoxyribonucleotides, and a and g in lower-case letters show ribonucleotides.

```
SEQ ID NO: 69:
gggagaggCaagaaTagggCCCagCTgaaaaaaaCCTggaCgTaCaCC
gTTCgCCgagCgggTgaagagaagagaCaTTagga SEQ ID NO: 70:
gggagaggCaagaaTagggCTggaaaTagaaCCgCgCTgTCTTCaTTa
agCCgCCCaaCggTgaagagaagagaCaTTagga SEQ ID NO: 71:
gggagaggCaagaaTagggCaCTTgaaaaaaaCCCaaaTTTaCCgTCT
TCagCgTCgggTgTgaagagaagagaCaTTagga SEQ ID NO: 72:
gggagaggCaagaaTagggCTggaTgggCagTaaCCTgaaaaaaaCCa
CCCaCCTCTaCCgTgaagagaagagaCaTTagga SEQ ID NO: 73:
gggagaggCaagaaTagggCaCTTgaaaaaaaCCCaagaaagaaTaC
TTaCCCggCgCgTgaagagaagagaCaTTagga SEQ ID NO: 74:
gggagaggCaagaaTagggCaTagTgTagaCCCCTCTCaagaTaCCCC
aTgaaTTgCCCCgTgaagagaagagaCaTTagga
```

The binding activities for NGF of the nucleic acids shown by SEQ ID NOs: 69-74 were evaluated by the surface plasmon resonance method. A method similar to that shown in Example 1 was used for the experiment. As a result, all of them were found to bind more significantly to NGF than 40N of the control.

Example 4

Preparation of NGF Aptamers Having Higher Activity

SELEX was performed using an RNA pool containing a sequence shown by SEQ ID NO: 36 doped with 30% random sequence and added with new primer sequences to the both ends thereof. SELEX was performed almost in the same manner as in Example 1. The sequences of the template and primers are shown below.

```
template:
                                    (SEQ ID NO: 123)
5'-GAGGATCCATGTATGCGCACATAgggttttttttcatcctgcagct
ccacaggcttcccCTTCTGGTCGAAGTTCT-3' a: a (70%), g (10%), c (10%), t (10%)
g: g (70%), a (10%), c (10%), t (10%)
c: c (70%), a (10%), g (10%), t (10%)
t: t (70%), a (10%), c (10%), g (10%)

primer Fwd:
                                    (SEQ ID NO: 124)
5'-CGGAATTCTAATACGACTCACTATAGGGAGAACTTCGACCAGAA
G-3' primer Rev:
                                    (SEQ ID NO: 125)
5'-GAGGATCCATGTATGCGCACATA-3'
```

After 10 rounds, the sequences of 48 clones were sequenced. Sequence convergence was not seen, but many sequences contained the consensus sequence of UGAAAAAAACC (SEQ ID NO: 91).

In addition, UGAAAGAAACC (SEQ ID NO: 92), UGAAAGAAACU (SEQ ID NO: 93), UGAAAACAACC (SEQ ID NO: 98), UGAAAUAAACC (SEQ ID NO: 99), UGAAAUAAACU (SEQ ID NO: 100), UGAAAAAAUCU (SEQ ID NO: 101) and the like, which contained mutation in the consensus sequence of UGAAAAAAACC (SEQ ID NO: 91), were also present.

Therefrom were selected 12 sequences at random, and the binding activities for NGF was measured by the surface plasmon resonance method. The measurement method is as shown in Example 1. As a result of the measurement, all of these 12 sequences were found to bind more significantly to NGF than the first template doped with 30% random sequence. The nucleotide sequences actually obtained, which correspond to each SEQ ID NO, are shown below.

```
SEQ ID NO: 75:
gggagaac(F)u(F)u(F)c(F)gac(F)c(F)agaagu(F)gaaag
aau(F)c(F)u(F)c(F)c(F)aaagac(F)aagau(F)aaaaac
(F)aac(F)c(F)gu(F)au(F)gu(F)gc(F)gc(F)au(F)ac
(F)au(F)ggau(F)c(F)c(F)u(F)c(F)

SEQ ID NO: 76:
gggagaac(F)u(F)u(F)c(F)gac(F)c(F)agaaggau(F)aaa
c(F)gc(F)au(F)gu(F)au(F)u(F)u(F)gc(F)agu(F)au
(F)u(F)aaaaau(F)gc(F)c(F)u(F)u(F)au(F)gu(F)gc
(F)gc(F)au(F)ac(F)au(F)ggau(F)c(F)c(F)u(F)c(F)

SEQ ID NO: 77:
gggagaac(F)u(F)u(F)c(F)gac(F)c(F)agaagu(F)gaaaa
aau(F)c(F)u(F)c(F)c(F)agu(F)u(F)gc(F)aagac(F)ga
aac(F)aaac(F)c(F)u(F)au(F)gu(F)gc(F)gc(F)au
(F)ac(F)au(F)ggau(F)c(F)c(F)u(F)c(F)

SEQ ID NO: 78:
gggagaac(F)u(F)u(F)c(F)gac(F)c(F)agaagu(F)gu(F)
gu(F)au(F)u(F)gu(F)u(F)c(F)agggu(F)gu(F)gc(F)c
(F)c(F)agc(F)c(F)u(F)au(F)aac(F)c(F)au(F)au(F)g
u(F)gc(F)gc(F)au(F)ac(F)au(F)ggau(F)c(F)c(F)u
(F)c(F)

SEQ ID NO: 79:
gggagaac(F)u(F)u(F)c(F)gac(F)c(F)agaaggau(F)agc
(F)c(F)au(F)gu(F)ggaggu(F)gaagac(F)u(F)gaaau(F)
aaac(F)c(F)au(F)au(F)gu(F)gc(F)gc(F)au(F)ac(F)a
u(F)ggau(F)c(F)c(F)u(F)c(F)

SEQ ID NO: 80:
gggagaac(F)u(F)u(F)c(F)gac(F)c(F)agaagu(F)gaaaa
c(F)aac(F)c(F)u(F)c(F)c(F)c(F)aau(F)aau(F)gau
(F)c(F)ac(F)agaaau(F)c(F)c(F)u(F)au(F)gu(F)gc
(F)gc(F)au(F)ac(F)au(F)ggau(F)c(F)c(F)u(F)c(F)

SEQ ID NO: 81:
gggagaac(F)u(F)u(F)c(F)gac(F)c(F)agaaggagau(F)g
ac(F)u(F)gu(F)gu(F)aac(F)c(F)ac(F)agu(F)au(F)ga
aau(F)aaac(F)u(F)c(F)u(F)au(F)gu(F)gc(F)gc(F)au
(F)ac(F)au(F)ggau(F)c(F)c(F)u(F)c(F)

SEQ ID NO: 82:
gggagaac(F)u(F)u(F)c(F)gac(F)c(F)agaagaggau(F)g
c(F)u(F)u(F)gu(F)u(F)u(F)ggu(F)u(F)ac(F)aagc(F)
u(F)gaaagaaac(F)c(F)u(F)u(F)au(F)gu(F)gc(F)gc
(F)au(F)ac(F)au(F)ggau(F)c(F)c(F)u(F)c(F)

SEQ ID NO: 83:
gggagaac(F)u(F)u(F)c(F)gac(F)c(F)agaagu(F)u(F)g
aagc(F)u(F)u(F)gaaaaaaac(F)c(F)c(F)aggau(F)u(F)
aaac(F)agac(F)agu(F)au(F)gu(F)gc(F)gc(F)au(F)ac
(F)au(F)ggau(F)c(F)c(F)u(F)c(F)

SEQ ID NO: 84:
gggagaac(F)u(F)u(F)c(F)gac(F)c(F)agaagu(F)gaaag
aaac(F)u(F)c(F)c(F)c(F)gau(F)gaaagau(F)gu(F)aac
(F)aaac(F)c(F)au(F)au(F)gu(F)gc(F)gc(F)au(F)ac
(F)au(F)ggau(F)c(F)c(F)u(F)c(F)

SEQ ID NO: 85:
gggagaac(F)u(F)u(F)c(F)gac(F)c(F)agagc(F)ggaag
c(F)c(F)u(F)gc(F)gu(F)aac(F)c(F)gc(F)aggau(F)ga
aaac(F)aac(F)c(F)gu(F)au(F)gu(F)gc(F)gc(F)au(F)
ac(F)au(F)ggau(F)c(F)c(F)u(F)c(F)

SEQ ID NO: 86:
gggagaac(F)u(F)u(F)c(F)gac(F)c(F)agaaggagu(F)ag
c(F)c(F)agu(F)gaac(F)c(F)u(F)ggaau(F)au(F)gaaaa
aaac(F)c(F)u(F)u(F)au(F)gu(F)gc(F)gc(F)au(F)ac
(F)au(F)ggau(F)c(F)c(F)u(F)c(F)
```

Example 5

Preparation of DNA Aptamers that Bind Specifically to NGF

DNA aptamers that bind specifically to NGF were prepared using the SELEX method. The SELEX method used was an improved method of the method of Fitzwater, Polisky et al. (Fitzwater and Polisky, Methods Enzymol. 267, 275-301, 1996). As a target substance, human NGF used in Example 1 was used. The pool for the first round was DNA with length 71 (40N-DNA) obtained by adding primer sequences to both ends of 40 nucleotide random sequence. To obtain single strand DNA, biotin(bio) was added to the 5' terminal of primer Rev.

```
template:
                                    (SEQ ID NO: 126)
5'-GGGATCGACAGGGCT-40N-CCGAGTCGTGCCATCT-3' primer Fwd:
                                    (SEQ ID NO: 127)
5'-GGGATCGACAGGGCT-3'
```

-continued primer Rev:
(SEQ ID NO: 128)
bio-AGATGGCACGACTCGG-3'

After the completion of 7 rounds, the sequences of 46 clones were sequenced in the same manner as in Example 1. As a result, 20 sequences shown by SEQ ID NO: 87 were present. The sequences thereof are shown below.

SEQ ID NO: 87:
GGGATCGACAGGGCTGCAGCACTGGCGTAGGTTGGAATATGGGTATTT
TTGTGGTCCGAGTCGTGCCATCT

Example 6

Aptamers that Inhibit the Binding of NGF and NGF Receptor

Figure 12:
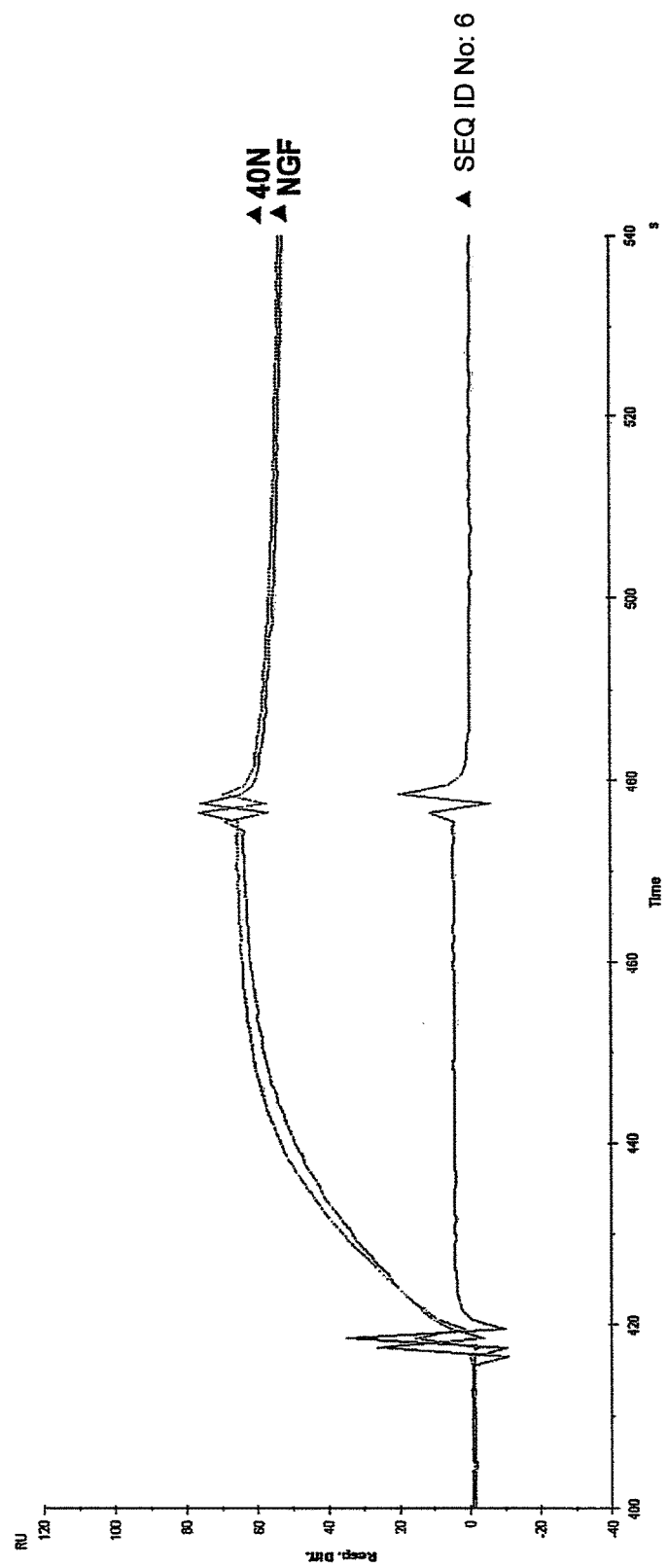
FIG. 12 is a drawing showing that the aptamer (Apt) shown by SEQ ID NO: 6 inhibits the binding of human NGF and human TrkA receptor, wherein 40N is an RNA containing a random sequence with 40 nucleotides. Using TrkA as a ligand, a mixture of NGF and Apt as an analyte, NGF alone as a negative control, and a mixture of NGF and 40N, the measurement was performed by BIAcore2000 manufactured by BIAcore.
Figure 13:
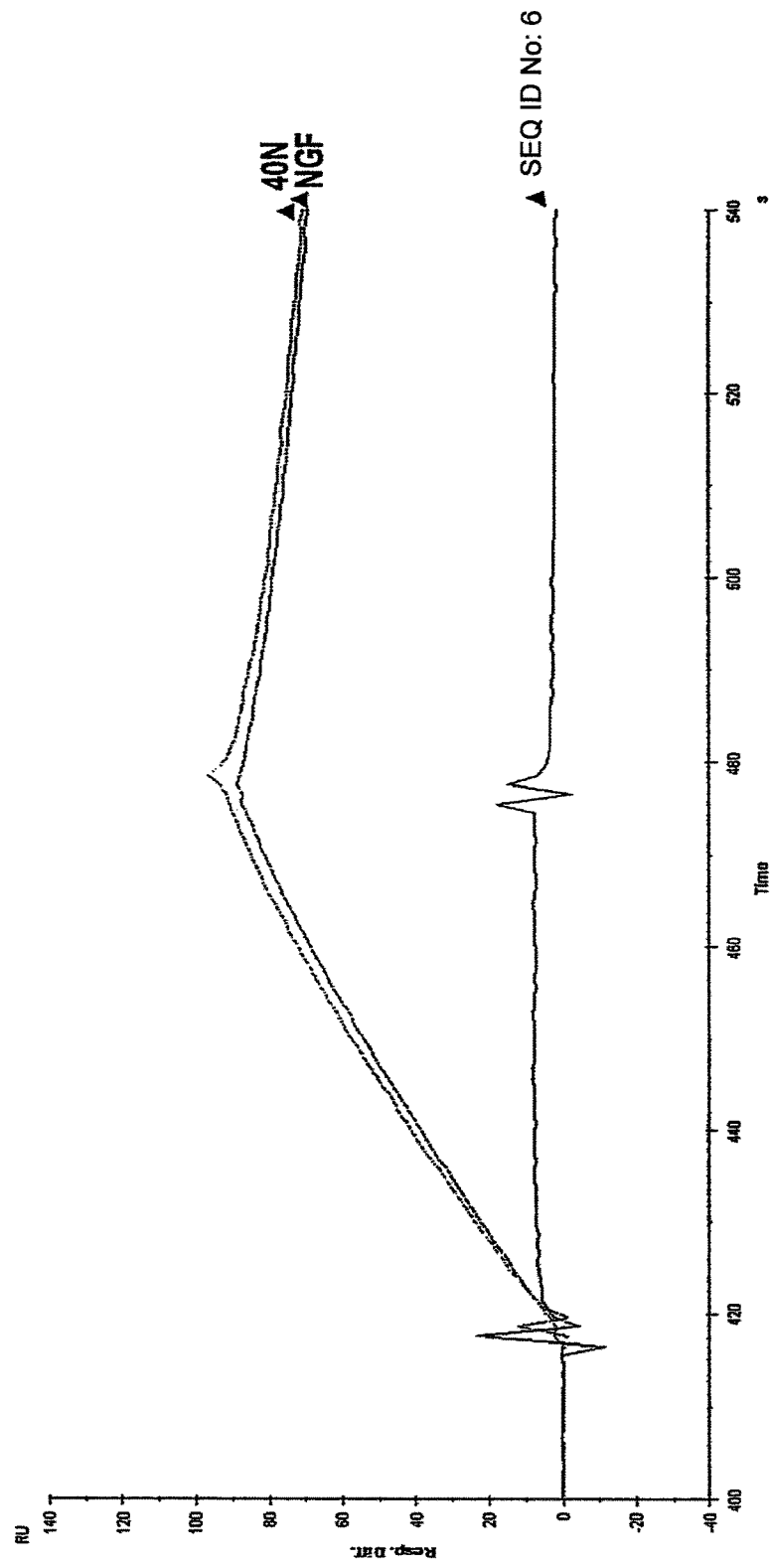
FIG. 13 is a drawing showing that the aptamer (Apt) shown by SEQ ID NO: 6 inhibits the binding of human NGF and human P75 receptor, wherein 40N is an RNA containing a random sequence with 40 nucleotides. Using TrkA as a ligand, a mixture of NGF and Apt as an analyte, NGF alone as a negative control, and a mixture of NGF and 40N, the measurement was performed by BIAcore2000 manufactured by BIAcore.

Whether the aptamers shown by SEQ ID NOs:1-9, 12 37-55 and 57-87 inhibit the binding of NGF and NGF receptor (TrkA and P75) was determined using the surface plasmon resonance method. As directed in BIAcore Company's protocol, Protein A (21181, PIERCE) was immobilized on a CM5 sensor chip. About 1100 RU of human Trk A-Fc fused with the Fc portion of IgG (175-TK, R&D systems) was immobilized thereon. As the analyte, a mixture of NGF (0.1 μM) and each aptamer (0.33 μM) was injected after being allowed to stand for 30 minutes. If the aptamer inhibits the binding of NGF and TrkA, the signal on the sensorgram is expected to not rise; if the aptamer does not inhibit the binding, a triple complex will be formed and the signal is expected to rise. When NGF binds stronger to a receptor than an aptamer, the aptamer may be removed and NGF may bind to the receptor. Before starting the inhibition experiment, binding of TrkA and NGF was confirmed. Using the binding amount of NGF and NGF receptor without an aptamer as 100, the binding amount of NGF and NGF receptor added with an aptamer was determined as a correction value. Here, the binding amount is the RU value at the peak top of the sensorgram of BIAcore (RU value immediately after completion of NGF injection). The correction value was subtracted from 100 to give an inhibitory activity %, where not less than 60% shows the presence of inhibitory activity. As a result of the experiment, all the aptamers shown by SEQ ID NOs: 1-9, 12, 37-55, 57-87 were found to inhibit the binding of NGF and TrkA (Table 1). As one example, inhibition of binding of NGF and TrkA by the aptamer shown by SEQ ID NO: 6 is shown in FIG. 12. A similar experiment was performed for another receptor P75 (p75-Fc; R&D systems). As a result, all the aptamers shown by SEQ ID NOs: 1-9, 12, 37-55, 57-87 were found to inhibit the binding of NGF and P75 by not less than 60% (Table 1). As one example, inhibition of binding of NGF and P75 by the aptamer shown by SEQ ID NO: 6 is shown in FIG. 13.

TABLE 1

|  | Length | inhibition experiment by BIACore | |
|---|---|---|---|
|  |  | TrKA | P75 |
| SEQ ID NO: 1 | 79 | + | + |
| SEQ ID NO: 2 | 78 | + | + |
| SEQ ID NO: 3 | 79 | + | + |
| SEQ ID NO: 4 | 79 | + | + |
| SEQ ID NO: 5 | 79 | + | + |
| SEQ ID NO: 6 | 79 | + | + |
| SEQ ID NO: 7 | 79 | + | + |
| SEQ ID NO: 8 | 78 | + | + |
| SEQ ID NO: 9 | 79 | + | + |
| SEQ ID NO: 12 | 79 | + | + |
| SEQ ID NO: 24 | 69 | + | + |
| SEQ ID NO: 25 | 47 | + | + |
| SEQ ID NO: 26 | 46 | + | + |
| SEQ ID NO: 27 | 45 | + | + |
| SEQ ID NO: 28 | 40 | + | + |
| SEQ ID NO: 29 | 61 | + | + |
| SEQ ID NO: 30 | 41 | + | + |
| SEQ ID NO: 31 | 34 | + | + |
| SEQ ID NO: 32 | 38 | + | + |
| SEQ ID NO: 33 | 36 | + | + |
| SEQ ID NO: 34 | 34 | + | + |
| SEQ ID NO: 35 | 38 | + | + |
| SEQ ID NO: 36 | 35 | + | + |
| SEQ ID NO: 37 | 74 | + | + |
| SEQ ID NO: 38 | 74 | + | + |
| SEQ ID NO: 39 | 74 | + | + |
| SEQ ID NO: 40 | 74 | + | + |
| SEQ ID NO: 41 | 74 | + | + |
| SEQ ID NO: 42 | 74 | + | + |
| SEQ ID NO: 43 | 73 | + | + |
| SEQ ID NO: 44 | 73 | + | + |
| SEQ ID NO: 45 | 74 | + | + |
| SEQ ID NO: 46 | 74 | + | + |
| SEQ ID NO: 47 | 74 | + | + |
| SEQ ID NO: 48 | 74 | + | + |
| SEQ ID NO: 49 | 74 | + | + |
| SEQ ID NO: 50 | 74 | + | + |
| SEQ ID NO: 51 | 77 | + | + |
| SEQ ID NO: 52 | 73 | + | + |
| SEQ ID NO: 53 | 74 | + | + |
| SEQ ID NO: 54 | 74 | + | + |
| SEQ ID NO: 55 | 72 | + | + |
| SEQ ID NO: 57 | 75 | + | + |
| SEQ ID NO: 58 | 74 | + | + |
| SEQ ID NO: 59 | 74 | + | + |
| SEQ ID NO: 60 | 74 | + | + |
| SEQ ID NO: 61 | 74 | + | + |
| SEQ ID NO: 62 | 74 | + | + |
| SEQ ID NO: 63 | 74 | + | + |
| SEQ ID NO: 64 | 74 | + | + |
| SEQ ID NO: 65 | 74 | + | + |
| SEQ ID NO: 66 | 74 | + | + |
| SEQ ID NO: 67 | 74 | + | + |
| SEQ ID NO: 68 | 74 | + | + |
| SEQ ID NO: 69 | 83 | + | + |
| SEQ ID NO: 70 | 82 | + | + |
| SEQ ID NO: 71 | 82 | + | + |
| SEQ ID NO: 72 | 82 | + | + |
| SEQ ID NO: 73 | 81 | + | + |
| SEQ ID NO: 74 | 82 | + | + |
| SEQ ID NO: 75 | 78 | + | + |
| SEQ ID NO: 76 | 78 | + | + |
| SEQ ID NO: 77 | 78 | + | + |
| SEQ ID NO: 78 | 78 | + | + |
| SEQ ID NO: 79 | 78 | + | + |
| SEQ ID NO: 80 | 78 | + | + |
| SEQ ID NO: 81 | 78 | + | + |
| SEQ ID NO: 82 | 78 | + | + |
| SEQ ID NO: 83 | 79 | + | + |
| SEQ ID NO: 84 | 78 | + | + |
| SEQ ID NO: 85 | 78 | + | + |
| SEQ ID NO: 86 | 78 | + | + |
| SEQ ID NO: 87 | 71 | + | + |

TABLE 1-continued

|  | Length | inhibition experiment by BIACore | |
|---|---|---|---|
|  |  | TrKA | P75 |
| SEQ ID NO: 88 | 33 | + | + |
| SEQ ID NO: 89 | 34 | + | + |
| SEQ ID NO: 90 | 32 | + | + |

Table 1 shows aptamers that inhibit binding of TrkA or p75 and NGF. "+" shows an inhibitory activity (%) of not less than 60%, and "−" shows that of less than 60%.

As to the aptamer shown by SEQ ID NO: 87, an inhibitory experiment similar to the above-mentioned was performed under conditions of NGF-aptamer molar ratio of 1:1 (0.1 μM). The same, prepared mixed solution of NGF and aptamer was used for the experiments of TrkA and P75, and the experiment was performed under no influence of variation in the sample preparation. As a result, the aptamer shown by SEQ ID NO: 87 inhibited the binding of NGF and TrkA by 93%, but inhibited the binding of NGF and p75 only by 29%.

Example 7

Evaluation of Physiological Activity of Aptamer by Using PC-12 Cells

The physiological activity of aptamer was evaluated by a neurite outgrowth suppressive experiment using PC-12 cells. PC-12 cell, which is a cell line derived from rat adrenal gland pheochromocytoma, is a model cell of the nervous system, elongates neurite by NGF stimulation, and differentiates like nerve cells. Whether or not an aptamer inhibits the neurite outgrowth was evaluated. PC-12 cells were seeded on a 96 well flat-bottom plate coated with collagen, and a mixed solution of NGF (final concentration 25 ng/ml, or 1.9 nM) prereacted for 1 hr at 37° C. and an aptamer (final concentration 500 nM) was added to start the cell culture. Thereafter, the same amount of the aptamer was added twice every 24 hr and the level of neurite outgrowth was observed and evaluated on day 3 with a microscope. For evaluation, scores 0-3 were used, where score 0 is no neurite outgrowth, score 1 is slight neurite outgrowth, score 2 is neurite outgrowth to the nearby cell, and score 3 is markedly reticulated neurite outgrowth. The system wherein PC-12 cells were cultivated for 3 days with the addition of NGF alone was taken as a negative control, and system capable wherein the cells for 3 days without addition of NGF was taken as a positive control. To confirm suppression of neurite outgrowth by an NGF inhibitor, 133 nM anti-NGF antibody (MAB2561, R&D Systems) as a control NGF inhibitor was added with NGF, the cells were cultured for 3 days and suppression of neurite outgrowth was confirmed. Setting the score of the negative control as inhibitory activity 0%, and the score of the positive control as inhibitory activity 100%, the inhibitory activity (%) of the aptamer was calculated. The results are shown in Table 2. An inhibitory activity of not less than 50% is shown with +, and that of less than 50% is shown with −. It was clarified that the aptamers shown by SEQ ID NOs: 1, 3-9 and 12 remarkably inhibit the neurite outgrowth (Table 2). The aptamer shown by SEQ ID NO: 2 free of a consensus sequence did not show an inhibitory activity. On the other hand, the aptamers shown by SEQ ID NOs: 5, 6 and the like containing a consensus sequence showed an inhibitory activity. The aptamer shown by SEQ ID NO: 8 showed an inhibitory activity, even though it was free of a consensus sequence. The foregoing shows that the aptamers shown by SEQ ID NOs: 1, 3-9 and 12 can be NGF inhibitors.

TABLE 2

|  | inhibitory activity |
|---|---|
| SEQ ID NO:1 | + |
| SEQ ID NO:2 | − |
| SEQ ID NO:3 | + |
| SEQ ID NO:4 | + |
| SEQ ID NO:5 | + |
| SEQ ID NO:6 | + |
| SEQ ID NO:7 | + |
| SEQ ID NO:8 | + |
| SEQ ID NO:9 | + |
| SEQ ID NO:12 | + |
| SEQ ID NO:24 | − |
| SEQ ID NO:25 | − |
| SEQ ID NO:26 | − |
| SEQ ID NO:27 | − |
| SEQ ID NO:28 | + |
| SEQ ID NO:29 | + |
| SEQ ID NO:30 | + |
| SEQ ID NO: 30(1) | + |
| SEQ ID NO: 30(2) | + |
| SEQ ID NO: 30(3) | + |
| SEQ ID NO: 31 | − |
| SEQ ID NO: 32 | + |
| SEQ ID NO: 32(1) | + |
| SEQ ID NO: 32(2) | + |
| SEQ ID NO: 32(3) | + |
| SEQ ID NO: 33 | − |
| SEQ ID NO: 34 | − |
| SEQ ID NO: 35 |  |
| SEQ ID NO: 35(1) | + |
| SEQ ID NO: 35(2) | + |
| SEQ ID NO: 35(3) | + |
| SEQ ID NO: 36 | − |
| SEQ ID NO: 88 | − |
| SEQ ID NO: 89 | − |
| SEQ ID NO: 90 | − |
| anti-NGF antibody | + |

Table 2 shows aptamers capable of inhibiting neurite outgrowth of PC12 cells. An inhibitory activity of not less than 50% is "+", and that less than 50% is "−".

Example 8

Evaluation of Physiological Activity of Aptamer by Using Neuroscreen-1 Cells

The neurite outgrowth inhibitory activity of aptamer was evaluated by using Neuroscreen-1 cell, which is a subclone of PC-12 cells. 2500 Cells per well were cultured for one day in an RPMI-1640 medium containing 2.5% horse serum and 1.25% fetal bovine serum in a 96 well flat-bottom plate coated with collagen type IV. A mixed solution of NGF (final concentration 15 ng/ml or 1.1 nM) prereacted in a serum-free RPMI-1640 medium at room temperature or 37° C. for 30 min to 1 hr and an aptamer (final concentration 500-3 nM) was added. Two or three days later, the cytoplasm and nuclei were stained using Cellomics Neurite Outgrowth Kits (manufactured by Thermo Scientific), and neurite length per cell was measured by Cellomics ArrayScan VTI (manufactured by Thermo Scientific). With the neurite length per cell obtained by culturing the cell for 2 days with the addition of NGF alone as inhibitory activity 0%, and that of the cell obtained by NGF free culture as inhibitory activity 100%, the inhibitory activity of the aptamer was calculated from the neurite length per cell obtained by culturing with the addition of NGF and the aptamer in mixture. The inhibitory activity when the aptamer concentrations were 100 n14 and 10 nM, and the 50% inhibitory concentration (IC50) are shown in Table 3. When the inhibitory activity was 0% or below, '0%' is indicated. When it was not less than 100%, '100%' is indicated. The 50% inhibitory concentration was determined from the concentrations at two, above and below points sandwiching the 50% inhibitory activity. An IC50 value indicated as < means an inhibitory activity of not less than 50% even at the lowest measurement concentration, and the indicated number shows the lowest measurement concentration. As a result of the experiment, the presence of aptamers having a high activity showing an IC50 of 10 nM or below was confirmed.

Such aptamers contained consensus sequences of UGAAAAAAACC (SEQ ID NO: 91), UGAAAGAAACC (SEQ ID NO: 92), UGAAAGAAACU (SEQ ID NO: 93), UGAAAAGAACC (SEQ ID NO: 95), UGAAAAAACCC (SEQ ID NO: 96), UGAAAGGAACC (SEQ ID NO: 105), CGAACAAAACU (SEQ ID NO: 103), CGAAAGAAACU (SEQ ID NO: 104) and AGAAUGAAACU (SEQ ID NO: 102). Six kinds and 5 kinds of aptamers contained UGAAAAAAACC (SEQ ID NO: 91) and UGAAAGAAACC (SEQ ID NO: 92), respectively.

TABLE 3

|  | 100 nM | 10 nM | IC50 (nM) |
|---|---|---|---|
| SEQ ID NO: 5 | 96.5 | 0.0 | 21.0 |
| SEQ ID NO: 6 | 98.6 | 20.1 | 17.7 |
| SEQ ID NO: 12 | 92.8 | 0.0 | 43.4 |
| SEQ ID NO: 30 | 81.9 | 29.2 | 57.6 |
| SEQ ID NO: 30(5) | 93.7 | N.D. | <100 |
| SEQ ID NO: 30(6) | 98.2 | 16.2 | 58.9 |
| SEQ ID NO: 32 | 64.0 | 0.0 | 84.7 |
| SEQ ID NO: 35 | 57.0 | 0.0 | 91.5 |
| SEQ ID NO: 35(1) | 54.1 | 0.0 | 94.7 |
| SEQ ID NO: 35(5) | 70.3 | 0.0 | 79.8 |
| SEQ ID NO: 35(6) | 80.4 | 0.0 | 73.5 |
| SEQ ID NO: 37 | 98.9 | 96.0 | 6.6 |
| SEQ ID NO: 38 | 98.1 | 82.2 | 7.3 |
| SEQ ID NO: 39 | 99.0 | 98.8 | 6.3 |
| SEQ ID NO: 40 | 99.6 | 100.0 | 2.4 |
| SEQ ID NO: 42 | 96.1 | 98.3 | 6.6 |
| SEQ ID NO: 43 | 97.3 | 67.4 | <10 |
| SEQ ID NO: 44 | 99.4 | 0.0 | 26.1 |
| SEQ ID NO: 45 | 99.1 | 12.3 | 20.2 |
| SEQ ID NO: 46 | 99.3 | 0.0 | 25.4 |
| SEQ ID NO: 47 | 98.2 | 35.9 | 14.6 |
| SEQ ID NO: 48 | 97.8 | 0.0 | 46.4 |
| SEQ ID NO: 49 | 98.3 | 97.9 | 4.6 |
| SEQ ID NO: 50 | 97.5 | 0.0 | 25.4 |
| SEQ ID NO: 51 | 99.4 | 45.1 | 11.9 |
| SEQ ID NO: 52 | 99.8 | 95.3 | 6.7 |
| SEQ ID NO: 53 | 100.0 | 53.4 | <10 |
| SEQ ID NO: 54 | 94.4 | 76.0 | 7.6 |
| SEQ ID NO: 55 | 96.2 | 0.0 | 49.9 |
| SEQ ID NO: 56 | 92.8 | 19.2 | 18.8 |
| SEQ ID NO: 57 | 94.1 | 96.8 | 6.4 |
| SEQ ID NO: 59 | 84.4 | 0.0 | 71.5 |
| SEQ ID NO: 60 | 99.8 | 99.1 | 2.2 |
| SEQ ID NO: 61 | 99.7 | 0.0 | 20.7 |
| SEQ ID NO: 62 | 100.0 | 99.6 | 2.0 |
| SEQ ID NO: 63 | 100.0 | 52.0 | <10 |
| SEQ ID NO: 64 | 100.0 | 96.1 | 4.8 |
| SEQ ID NO: 65 | 100.0 | 0.0 | 22.2 |
| SEQ ID NO: 66 | 100.0 | 68.7 | <10 |
| SEQ ID NO: 67 | 99.6 | 96.1 | 2.7 |

TABLE 3-continued

|  | 100 nM | 10 nM | IC50 (nM) |
|---|---|---|---|
| SEQ ID NO: 68 | 100.0 | 99.8 | 1.9 |
| SEQ ID NO: 83 | 90.0 | 84.6 | 7.1 |
| SEQ ID NO: 84 | 92.7 | 37.5 | 14.6 |

(N.D. in Table means not measured.)

Table 3 shows the inhibitory activity (%) when the concentrations of the aptamer inhibiting the neurite outgrowth of the Neuroscreen-1 cells were 100 nM and 10 nM, and 50% inhibitory concentration (IC50).

Example 9

Chain Shortening of Aptamer

Chain shortening of the aptamers shown by SEQ ID NOs: 2, 5, 6, 8 was performed. The aptamers shown by SEQ ID NOs: 5, 6 contain a consensus sequence of UGAAAAAAACC (SEQ ID NO: 91). The aptamers shown by SEQ ID NOs: 2 and 8 do not contain such consensus sequence. The sequences of the variants are as described below.

SEQ ID NO: 24: 69 nucleotide aptamer which is a variant of the aptamer shown by SEQ ID NO: 2 gggaagc(F)c(F)u(F)gu(F)ggagc(F)u(F)gc(F)c(F)u(F)ac(F)ac(F)u(F)u(F)u(F)agu(F)au(F)gac(F)aaac(F)c(F)u(F)agagu(F)gu(F)aaau(F)gc(F)u(F)u(F)c(F)gc(F)au(F)u(F)gu(F)c(F)ac(F)c(F)

SEQ ID NO: 25: 47 nucleotide aptamer which is a variant of the aptamer shown by SEQ ID NO: 2 ggagc(F)u(F)gc(F)c(F)u(F)ac(F)ac(F)u(F)u(F)u(F)agu(F)au(F)gac(F)aaac(F)c(F)u(F)agagu(F)gu(F)aaau(F)gc(F)u(F)u(F)c(F)

SEQ ID NO: 26: 46 nucleotide aptamer which is a variant of the aptamer shown by SEQ ID NO: 5 gggc(F)u(F)gu(F)ggagc(F)u(F)gc(F)u(F)u(F)aaac(F)aagc(F)aagu(F)gaaaaaaac(F)c(F)ac(F)agc(F)c(F)c(F)

SEQ ID NO: 27: 45 nucleotide aptamer which is a variant of the aptamer shown by SEQ ID NO: 6 gggaagc(F)c(F)u(F)gu(F)ggagc(F)u(F)gc(F)aggau(F)gaaaaaaac(F)c(F)c(F)aaaau(F)u(F)aaau(F)

SEQ ID NO: 28: 40 nucleotide aptamer which is a variant of the aptamer shown by SEQ ID NO: 6 gggaagc(F)c(F)u(F)gu(F)ggagc(F)u(F)gc(F)aggau(F)gaaaaaaac(F)c(F)c(F)aaaau(F)

SEQ ID NO: 29: 61 nucleotide aptamer which is a variant of the aptamer shown by SEQ ID NO: 8 ggu(F)ggagc(F)u(F)gc(F)ggau(F)aaaaau(F)agagu(F)u(F)u(F)gau(F)aaac(F)ac(F)c(F)u(F)gu(F)au(F)u(F)aaaac(F)c(F)gc(F)au(F)u(F)gu(F)c(F)ac(F)c(F)

SEQ ID NO: 30: 41 nucleotide aptamer which is a variant of the aptamer shown by SEQ ID NO: 8 gggau(F)aaaaau(F)agagu(F)u(F)u(F)gau(F)aaac(F)ac(F)c(F)u(F)gu(F)au(F)u(F)aaaac(F)c(F)c(F)

SEQ ID NO: 31: 34 nucleotide aptamer which is a variant of the aptamer shown by SEQ ID NO: 26 gggagc(F)u(F)gc(F)u(F)u(F)aaac(F)aagc(F)aagu(F)gaaaaaaac(F)c(F)c(F)

SEQ ID NO: 32: 38 nucleotide aptamer which is a variant of the aptamer shown by SEQ ID NO: 26 u(F)gu(F)ggagc(F)u(F)gc(F)u(F)u(F)aaac(F)aagc(F)aagu(F)gaaaaaaac(F)c(F)ac(F)a SEQ ID NO: 33: 36 nucleotide aptamer which is a variant of the aptamer shown by SEQ ID NO: 26 u(F)gu(F)ggagc(F)u(F)gc(F)u(F)aaac(F)agc(F)aagu(F)gaaaaaaac(F)c(F)ac(F)a SEQ ID NO: 34: 34 nucleotide aptamer which is a variant of the aptamer shown by SEQ ID NO: 26 gu(F)ggagc(F)u(F)gu(F)u(F)aaac(F)aac(F)aagu(F)gaaaaaaac(F)c(F)ac(F)

SEQ ID NO: 35: 38 nucleotide aptamer which is a variant of the aptamer shown by SEQ ID NO: 28 gggaagc(F)c(F)u(F)gu(F)ggagc(F)u(F)gc(F)aggau(F)gaaaaaaac(F)c(F)c(F)aaa SEQ ID NO: 36: 35 nucleotide aptamer which is a variant of the aptamer shown by SEQ ID NO: 28 gggaagc(F)c(F)u(F)gu(F)ggagc(F)u(F)gc(F)aggau(F)gaaaaaaac(F)c(F)c(F)

SEQ ID NO: 88: 33 nucleotide aptamer which is a variant of the aptamer shown by SEQ ID NO: 36 gggaagc(F)c(F)gu(F)ggagc(F)u(F)gc(F)ggau(F)gaaaaaaac(F)c(F)c(F)

SEQ ID NO: 89: 34 nucleotide aptamer which is a variant of the aptamer shown by SEQ ID NO: 36 gggaagc(F)c(F)u(F)gu(F)aaac(F)agc(F)aggau(F)gaaaaaaac(F)c(F)c(F)

SEQ ID NO: 90: 32 nucleotide aptamer which is a variant of the aptamer shown by SEQ ID NO: 36 gggagc(F)c(F)u(F)gu(F)aaac(F)agc(F)aggu(F)gaaaaaaac(F)c(F)c(F)

Figure 14:
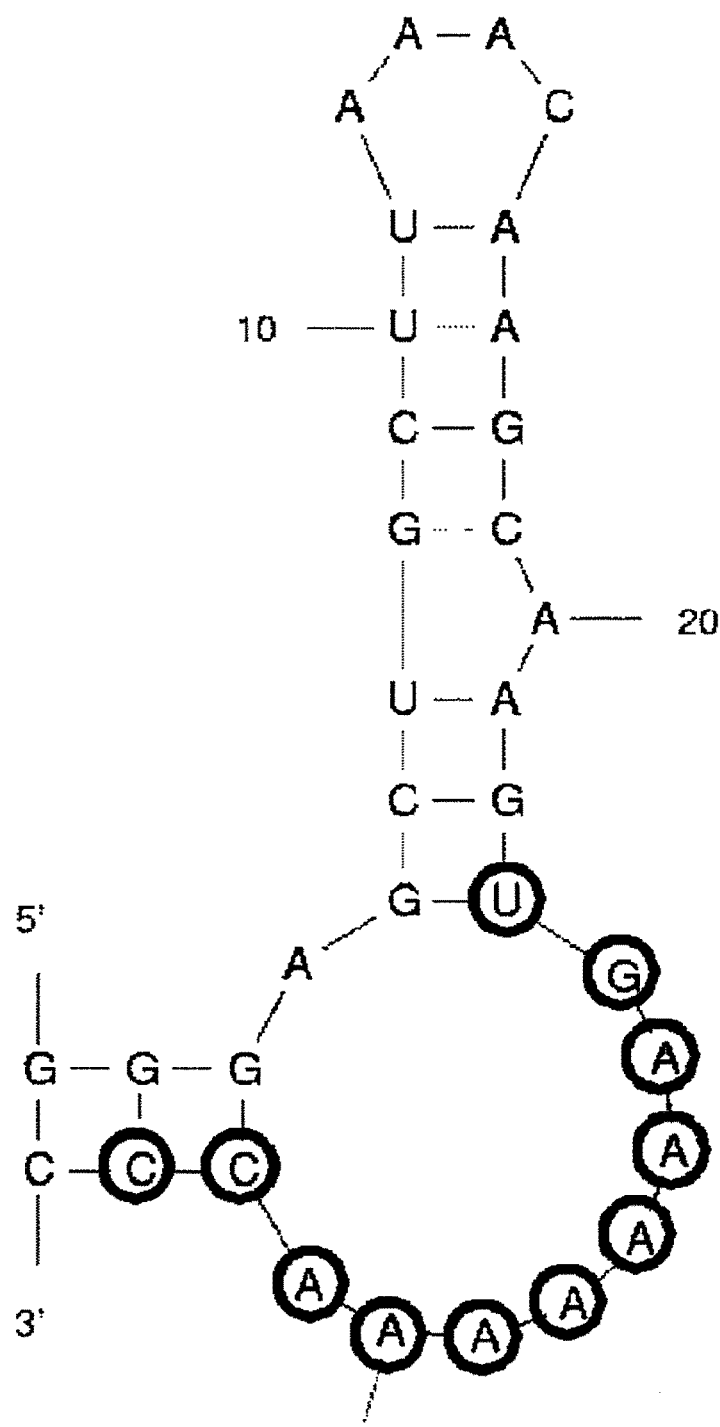
FIG. 14 shows the secondary structure of aptamer shown by SEQ ID NO: 31 predicted by the MFOLD program, wherein the part enclosed in a black circle shows a consensus sequence.
Figure 15:
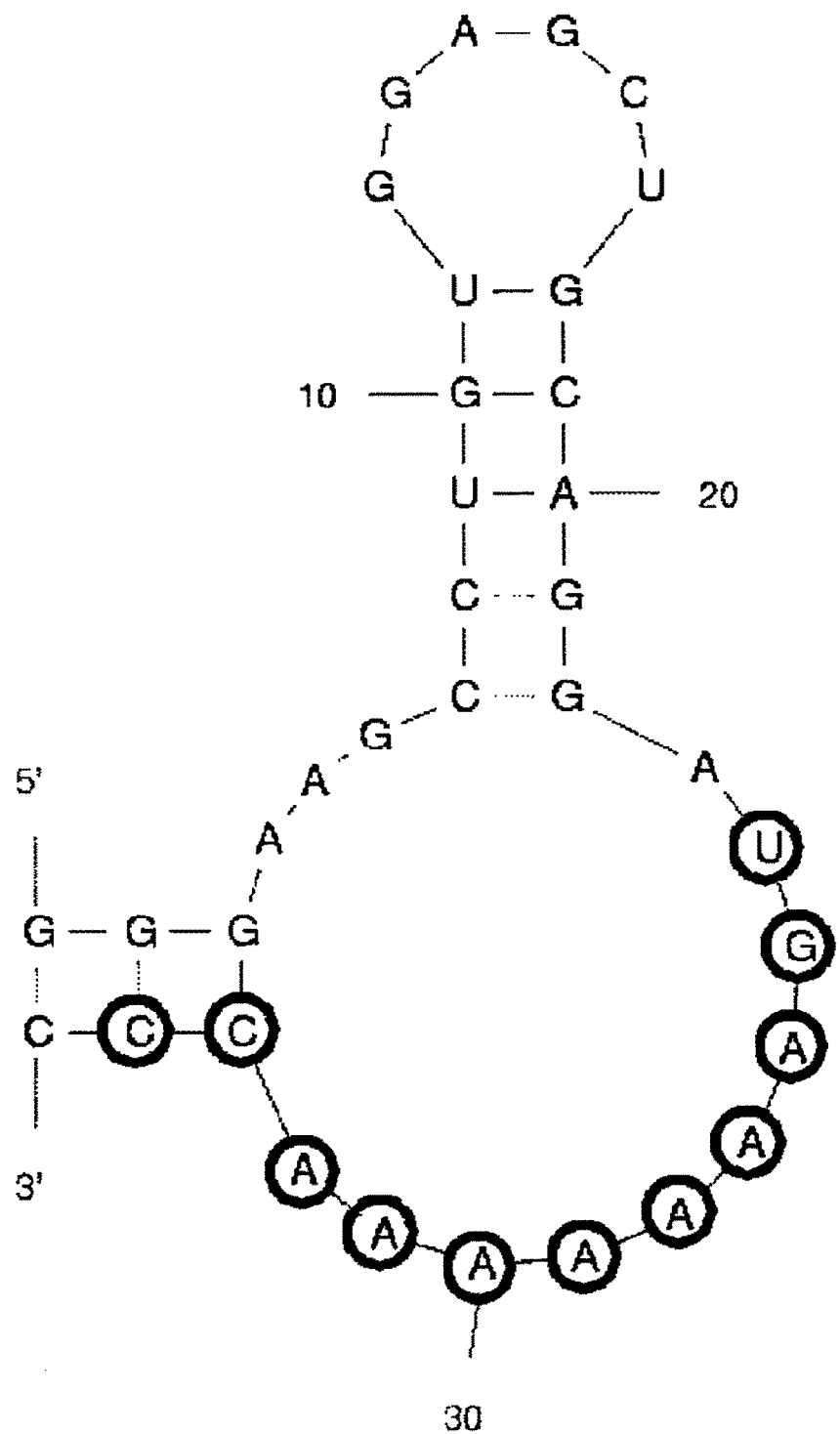
FIG. 15 shows the secondary structure of aptamer shown by SEQ ID NO: 36 predicted by the MFOLD program, wherein the part enclosed in a black circle shows a consensus sequence.

Putative secondary structures of the aptamers shown by SEQ ID NOs: 31 and 36 are shown in FIG. 14 and FIG. 15. The consensus sequence is shown with a black circle.

Aptamers with a length of 40 nucleotides or longer were prepared by transcription and aptamers with a length shorter than that were prepared by chemical synthesis. Whether these nucleic acids inhibit the binding of NGF and NGF receptor was examined in the same manner as in Example 6 by surface plasmon resonance method. As a result, all these nucleic acids were found to have an inhibitory activity (Table 1).

In addition, the neurite outgrowth inhibitory activity against PC12 cells was examined in the same manner as in Example 7. As a result, a strong inhibitory activity was found in SEQ ID NOs: 28-30, 32, 35 (Table 2).

The aptamer shown by SEQ ID NO: 32 has been shortened to 38 nucleotides maintaining the consensus sequence of the aptamer shown by SEQ ID NO: 5. In addition, the aptamer shown by SEQ ID NO: 35 has been shortened to 38 nucleotides maintaining the consensus sequence of the aptamer shown by SEQ ID NO: 6. From the above, it has been shown that the consensus sequence is important at least for SEQ ID NOs: 5 and 6.

On the other hand, the aptamer shown by SEQ ID NO: 30 is a chain-shortened sequence of the aptamer shown by SEQ ID NO: 8 free of the consensus sequence, and the activity was confirmed with the length of 41 nucleotides. These aptamers were shown to be usable as NGF inhibitors.

Example 10

Modification of Chain-Shortened Aptamers

To enhance the stability of the aptamers shown by SEQ ID NOs: 30, 32, 35 in blood, variants wherein the hydroxyl group at the 2'-position of ribose has been replaced by an o-methyl group were prepared. In the same manner as in Example 7, the neurite outgrowth inhibition by PC12 cells was examined. As a result, all these aptamers showed a strong inhibitory activity.

The sequences of the modified forms are shown below. The parentheses in the nucleotides show the 2'-position modification, F is fluorine atom, M is o-methyl group, and idT is inverted dT.

SEQ ID NO: 30(1):
idT-gggau(F)aaaaau(F)a(M)g(M)a(M)g(M)u(F)u(F)g(M)a(M)u(F)a(M)a(M)a(M)c(F)a(M)c(F)c(F)u(F)gu(F)au(F)u(F)aaaac(F)c(F)c(F)-idT SEQ ID NO: 30(2):
gggau(F)aaaa(M)a(M)u(F)agagu(F)u(F)u(F)gau(F)aaac(F)ac(F)c(F)u(F)gu(F)au(F)u(F)aaaac(F)c(F)c(F)

SEQ ID NO: 30(3):
gggau(F)aaaaau(F)agagu(F)u(F)u(F)gau(F)aaac(F)ac(F)c(F)u(F)gu(F)au(F)u(F)a(M)aac(F)c(F)c(F)

SEQ ID NO: 30(4):
idT-gggau(F)aaaa(M)a(M)u(F)a(M)g(M)a(M)g(M)u(F)u(F)u(F)g(M)a(M)u(F)a(M)a(M)a(M)c(F)a(M)c(F)c(F)u(F)gu(F)au(F)u(F)a (M)a(M)aac(F)c(F)c(F)-idT SEQ ID NO: 30(5):
idT-gggau(F)aaaa(M)a(M)u(F)a(M)g(M)a(M)g(M)u(F)u(F)u(F)g(M)a(M)u(F)a(M)a(M)a(M)c(F)a(M)c(F)c(F)u(F)gu(F)a(F)u(F)u(F)a(M)a(M)a(F)a(F)c(F)c(F)c(F)-idT SEQ ID NO: 30(6):
idT-g(M)g(M)g(M)au(F)a(M)as(M)a(M)a(M)u(F)a(M)g(M)a(M)g(M)u(F)u(F)u(F)g(M)a(M)u(F)a(M)a(M)a(M)c(F)a(M)c(F)c(F)u(F)gu(F)a(M)u(F)u(F)a(M)a(M)a(F)a(F)c(F)c(F)c(F)-idT SEQ ID NO: 32(1):
idT-u(F)gu(F)ggagc(F)u(F)g(M)c(F)u(F)u(F)a(M)a(M)a(M)c(F)a(M)a(M)g(M)c(F)a(M)a(M)g(M)u(F)gaaaaaac(F)c(F)ac(F)a-idT SEQ ID NO: 32(2):
u(F)g(M)u(F)ggagc(F)u(F)gc(F)u(F)u(F)aaac(F)aagc(F)aagu(F)gaaaaaaac(F)c(F)ac(F)a(M)

SEQ ID NO: 32(3):
u(F)gu(F)ggagc(F)u(F)gc(F)u(F)u(F)aaac(F)aagc(F)aagu(F)gaaaa(M)a(M)aac(F)c(F)ac(F)a SEQ ID NO: 32(4):
u(F)gu(F)gga(M)gc(F)u(F)gc(F)u(F)u(F)aaac(F)aagc(F)aagu(F)gaaaaaaac(F)c(F)ac(F)a SEQ ID NO: 32(5):
idT-u(F)g(M)u(F)gga(M)gc(F)u(F)g(M)c(F)u(F)u(F)a(M)a(M)a(M)c(F)a(M)a(M)g(M)c(F)aagu(F)gaaaa(M)a(M)a(M)a(M)c(F)c(F)ac(F)a-idT SEQ ID NO: 32(6):
idT-u(F)g(M)u(F)g(M)ga(M)gc(F)u(F)g(M)c(F)u(F)u(F)a(M)a(M)a(M)c(F)a(M)a(M)g(M)c(F)a(M)a(M)g(M)u(F)gaaaa(M)a(M)a(M)a(M)c(F)c(F)ac(F)a-idT SEQ ID NO: 35(1):
idT-ggga(M)a(M)g(M)c(F)c(F)u(F)g(M)u(F)g(M)g(M)a(M)g(M)c(F)u(F)g(M)c(F)a(M)g(M)g(M)au(F)gaaaaaac(F)c(F)c(F)aaa-idT SEQ ID NO: 35(2):
idT-ggga(M)a(M)g(M)c(F)c(F)u(F)g(M)u(F)ggagc(F)u(F)g(M)c(F)a(M)g(M)g(M)au(F)gaaaa(M)a(M)a(M)a(M)c(F)c(F)c(F)aaa-idT SEQ ID NO: 35(3):
gggaagc(F)c(F)u(F)gu(F)ggagc(F)u(F)gc(F)aggau(F)gaaaaaaac(F)c(F)c(F)a(M)a(M)a(M)

SEQ ID NO: 35(4):
idT-ggga(M)a(M)g(M)c(F)u(F)g(M)u(F)g(M)g(M)a(M)g(M)c(F)u(F)g(M)c(F)a(M)g(M)g(M)au(F)gaaaa(M)a(M)a(M)a(M)c(F)c(F)c(F)a(M)a(M)a(M)-idT -continued SEQ ID NO: 35(5):
idT-g(M)g(M)ga(M)a(M)g(M)c(F)c(F)u(F)g(M)u(F)g
(M)g(M)a(M)g(M)c(F)u(F)g(M)c(F)a (M)g(M)g(M)au
(F)gaaaa(M)a(M)a(M)a(M)c(F)c(F)c(F)a(M)a(M)a
(M)-idT SEQ ID NO: 35(6):
idT-g(M)g(M)ga(M)a(M)g(M)c(F)c(F)u(F)g(M)u(F)g
(M)g(M)a(M)g(M)c(F)u(F)g(M)c(F)a(M)g(M)g(M)a(F)
u(F)gaaaa(M)a(M)a(M)a(M)c(F)c(F)c(F)a(M)a(M)a
(M)-idT Example 11

Identification of NGF Binding Site of Aptamer by Footprint Method

To confirm that the consensus sequence is an NGF binding site, an enzyme digestion experiment was performed in the absence of NGF and in the presence of NGF. When the consensus sequence is an NGF binding site, the results should be that enzyme digestion occurs in the absence of NGF; nuclease cannot bind to a consensus sequence in the presence of NGF and enzyme digestion does not occur. Using an aptamer wherein a fluorescent substance (FAM6) was conjugated with the 5' terminal or 3' terminal of the aptamer shown by SEQ ID NO: 62, the experiment was performed. The aptamer shown by SEQ ID NO: 62 contains a consensus sequence of UGAAAGAAACC (SEQ ID NO: 92). As the nuclease, 3 kinds of S1 nuclease (manufactured by TAKARA BIO) that selectively cleaves single strands, V1 nuclease (manufactured by Ambion) that selectively cleaves double strands, and T1 nuclease (manufactured by Ambion) that selectively cleaves G of single strands were used. Each enzyme reaction was performed under the conditions of Table 4 in reference to the attached specification document. To the reaction solution of S1 nuclease was added 0.833 mM $ZnCl_2$.

TABLE 4

| nuclease | enzyme amount (U/μL) | aptamer amount (μM) | time | temperature |
|---|---|---|---|---|
| S1 | 8.33 | 8 | 3 min, 10 min | room temperature |
| V1 | 0.009 | 9 | 1 min, 3 min | room temperature |
| T1 | 0.91 | 9 | 1 min, 3 min | room temperature |

In the experiment with addition of NGF, the molar ratio of aptamer and NGF was set to 1:2, and they were dissolved in solution B, a binding buffer. Here, solution B is a mixed solution of 145 mM sodium chloride, 5.4 mM potassium chloride, 1.8 mM calcium chloride, 0.8 mM magnesium chloride, and 20 mM Tris (pH 7.6).

After an enzyme reaction, the reaction was discontinued by a phenol.chloroform treatment, and a water-soluble fraction was recovered and concentrated. Then, the terminal phosphoric acid was removed by alkaline phosphatase (manufactured by TAKARA BIO). The enzyme treatment with alkaline phosphatase was performed at 37° C. for 1.5 hr by reference to the attached specification document. These samples were analyzed by 20% denatured polyacrylamide electrophoresis. For fluorescence detection, Storm850 (manufactured by GE Healthcare) was used. As a result of the experiment, GAAAGA of UGAAAGAAACC (SEQ ID NO: 92) was cleaved by S1 and T1 nucleases in the absence of NGF. On the other hand, the cleavage was remarkably suppressed in the presence of NGF. Here, pyrimidine nucleotide is a fluoro-modified form. The above reveals that the consensus sequence part is an NGF binding site.

Example 12

Changes in Activity by Introduction of Mutation into Consensus Sequence Part

Mutation was introduced into the consensus sequence part, and changes in the activity were evaluated using Neuroscreen-1 cells in the same manner as in Example 8. As an aptamer containing a consensus sequence UGAAAAAAACC (SEQ ID NO: 91), a 38 nucleotide long sequence shown by SEQ ID NO: 35 was used. The results thereof are shown in Table 5.

When an aptamer free of mutation introduction was added at 300 nM, inhibition of neurite outgrowth by 92% was seen. On the other hand, the activity disappeared completely by the introduction of a mutation of one nucleotide. When A at the 3rd to 5th of UGAAAAAAACC (SEQ ID NO: 91) was substituted by DNA type, the activity disappeared completely. From the above, it was shown that the consensus sequence is important for inhibition of NGF activity.

TABLE 5

| consensus sequence | 300 nM (% Inhibition) |
|---|---|
| UGAAAAAAACC | 92 |
| UCAAAAAAACC | 0 |
| UgAAAAAAACC | 0 |
| UGGAAAAAACC | 0 |
| UGaAAAAAACC | 0 |
| UGAaAAAAACC | 0 |
| UGAAaAAAACC | 0 |

Table 5 shows the results of the neurite outgrowth inhibitory experiment using Neuroscreen-1 cells. The aptamer shown by SEQ ID NO: 35 and a variant thereof were added at 300 nM. The pyrimidine nucleotide is a fluoro-modified form, the capital letters of purine nucleotide show RNA type, and lower-case letters show DNA type. The mutation was introduced into the underlined parts.

Example 13

Consideration Relating to Consensus Sequences

In this experiment, consensus sequences appeared at high frequency in SELEX under different conditions such as different pools, primer sequences and the like (Examples 1-4). Of the 74 sequences obtained by SELEX, 59 sequences contained aptamers having a consensus sequence of UGAAANNANCY (SEQ ID NO: 107), wherein N is any nucleotide of A, G, C and U, and U may be T. Y is a pyrimidine nucleotide. Of these, 29 sequences contained UGAAAGAAACY (SEQ ID NO: 110) and 13 sequences contained UGAAAGAAACY (SEQ ID NO: 111).

On the other hand, consensus sequences shown by the formulas CGAANNAAACY (SEQ ID NO: 108) and AGAANNAAACY (SEQ ID NO: 109) were found in 3 sequences and 2 sequences, respectively. Of these, one sequence contained CGAACAAAACY (SEQ ID NO: 112), and one sequence contained CGAAAGAAACY (SEQ ID NO: 113). They can be shown by the formula HGAANN-NANCY (SEQ ID NO: 106).

Since these consensus sequences are necessary for 38 nucleotide chain-shortened form (Example 9), protected by the addition of NGF in an enzyme digestion experiment (Example 11), and physiological activity markedly decreases by the introduction of a mutation (Example 12), it is clear that they are important for inhibiting NGF function.

Example 14

Introduction of Mutation into Chain-Shortened Aptamer

Whether the activity can be maintained after introduction of a mutation into a chain-shortened aptamer was confirmed. The aptamer of SEQ ID NO: 30(6) has a length of 41 nucleotides and does not contain a consensus sequence. Inverted dT is added to the 5' and 3' terminals. The activity was evaluated using Neuroscreen-1 cells in the same manner as in Example 8. The results are shown in Table 6.

When the G1:C41, A10:U33, A12:U31 base pairs in the stem part predicted by the MFOLD program were substituted by C1:G41, U10:A33, U12:A31, the activity did not decrease markedly. When G20 and G23 in the loop part were substituted by A20 and A23, the activity did not decrease markedly, either. From the above, it was shown that the activity of the aptamer shown by SEQ ID NO: 30(6) was maintained even after introduction of several mutations.

TABLE 6

|  | (% Inhibition) | | |
| --- | --- | --- | --- |
|  | 300 nM | 100 nM | 30 nM |
| G1:C41→C:G | 98.1 | 92.0 | 19.5 |
| A10:U33→U:A | 98.3 | 80.8 | 12.1 |
| A12:U31→U:A | 96.0 | 93.1 | 35.8 |
| G20→A | 98.1 | 96.1 | 47.7 |
| G23→A | 98.0 | 91.2 | 31.0 |
| SEQ ID NO: 30 | 98.6 | 92.7 | 28.4 |

Example 15

Comparison with NGF Aptamer Described in Prior Art Reference

The aptamers shown by SEQ ID NOs: 30, 32, 35 and NGF aptamers described in prior art reference (Binkley J et al., (1995) Nucleic Acids Res. 23, 3198) were compared for NGF binding activity, NGF-NGF receptor binding inhibitory activity and neurite outgrowth inhibitory activity.

The aptamers described in the prior art reference were all unmodified RNAs, and the sequences thereof do not match with the sequences described in the present specification. As the aptamers described in the prior art reference, H1, L2 and L6 showing high binding activity were selected, and transcribed with T7 polymerase. The binding activity was evaluated by a method similar to that in Example 1, NGF-NGF receptor binding inhibitory activity was evaluated by a method similar to that in Example 6, and the neurite outgrowth inhibitory activity was evaluated by a method similar to that in Example 8.

As a result, it was found that H1, L2 and L6 bind to NGF but the activity is lower than the aptamers shown by SEQ ID NOs: 30, 32, 35 (Table 7). Moreover, H1, L2 and L6 did not inhibit binding of NGF and NGF receptor, and did not show an inhibitory activity even when added at 500 nM in the neurite outgrowth inhibitory experiment (Table 7). From the above, it was shown that the aptamers described in the present specification have higher activity than the aptamers described in the prior art reference.

TABLE 7

|  | binding with NGF (BIACore) | NGF-NGF receptor binding inhibition | | NGF neurite outgrowth inhibitory activity (%) | |
| --- | --- | --- | --- | --- | --- |
|  |  | TrkA | P75 | 500 nM | 250 nM |
| SEQ ID NO: 30 | ++ | + | + | 100.0 | 100.0 |
| SEQ ID NO: 32 | ++ | + | + | 100.0 | 97.4 |
| SEQ ID NO: 35 | ++ | + | 100.0 | 94.5 |  |
| H1 | + | − | − | 0.0 | 0.0 |
| L2 | − | − | − | 0.0 | 0.0 |
| L6 | − | − | − | 0.0 | 0.0 |

Table 7 shows NGF binding activity, NGF-NGF receptor binding inhibition, and NGF neurite outgrowth inhibitory activity of the aptamers shown by SEQ ID NOs: 30, 32, 35 and the aptamers H1, L2, L6 described in non-patent document 1.

The NGF binding activity was evaluated based on the maximum RU value obtained by the binding of NGF and SEQ ID NO: 35 as 100%. When it is not less than 80%, "++" is indicated, when it is not less than 50%, "+" is indicated, and when it is 50% or below, "−" is indicated. As for NGF-NGF receptor binding inhibition, "+" means an inhibitory activity (%) of not less than 60%, and "−" means an inhibitory activity (%) of less than 60%.

The NGF neurite outgrowth inhibitory activity is the inhibitory activity (%) when the final concentration of the aptamer is 500 nM or 250 nM.

INDUSTRIAL APPLICABILITY

The aptamer and the complex of the present invention can be useful as medicaments, diagnostic agents or reagents for diseases such as pain, inflammatory disease and the like. The aptamer and the complex of the present invention can also be useful for the purification and concentration of NGF, as well as detection and quantification of NGF.

This application is based on a patent application No. 2008-244982 filed in Japan (filing date: Sep. 24, 2008), the contents of which are incorporated in full herein.

The invention claimed is:

1. An aptamer that binds to NGF and inhibits binding of NGF and an NGF receptor, comprising a nucleotide sequence of:
UGAAAAAAACC (SEQ ID NO: 91),
UGAAAGAAACC (SEQ ID NO: 92),
UGAAAGAAACU (SEQ ID NO: 93),
UGAAACAAACC (SEQ ID NO: 94),
UGAAAAGAACC (SEQ ID NO: 95),
UGAAAAAACCC (SEQ ID NO: 96),
UGAAAAAACCU (SEQ ID NO: 97),
UGAAAACAACC (SEQ ID NO: 98),
UGAAAUAAACC (SEQ ID NO: 99),
UGAAAUAAACU (SEQ ID NO: 100),
UGAAAAAAUCU (SEQ ID NO: 101),
AGAAUGAAACU (SEQ ID NO: 102),
CGAACAAAACU (SEQ ID NO: 103),
CGAAAGAAACU (SEQ ID NO: 104),
UGAAAGGAACC (SEQ ID NO: 105),
UGAAAAAAACY (SEQ ID NO: 110),
UGAAAGAAACY (SEQ ID NO: 111),
CGAACAAAACY (SEQ ID NO: 112), or
CGAAAGAAACY (SEQ ID NO: 113);
wherein Y is a pyrimidine nucleotide,
wherein the 11th pyrimidine nucleotide (C, U or Y) is modified at 2'-, 3'- and/or 4'-position of the sugar residue, and wherein the modification is selected from the group consisting of fluorination, O-alkylation, O-arylation, S-alkylation, S-arylation, and amination, and
wherein the length of the aptamer is 32 to 50 nucleotides.

2. The aptamer according to claim 1, wherein at least one nucleotide other than the 11th pyrimidine nucleotide is modified.

3. The aptamer according to claim 1, comprising a sequence UGAAAAAAACY (SEQ ID NO: 110), UGAAAGAAACY (SEQ ID NO: 111), CGAACAAAACY (SEQ ID NO: 112), CGAAAGAAACY (SEQ ID NO: 113) or AGAAUGAAACU (SEQ ID NO: 102), wherein at least one nucleotide other than the 11th pyrimidine nucleotide of the aforementioned sequence is modified.

4. The aptamer according to claim 2, wherein the groups at the 2'-position of a ribose of respective pyrimidine nucleotides are the same or different and is a hydroxyl group, hydrogen atom, fluorine atom or methoxy group.

5. The aptamer according to claim 2, wherein the groups at the 2'-position of a ribose of respective purine nucleotides are the same or different and is a hydroxyl group, hydrogen atom, fluorine atom or methoxy group.

6. The aptamer according to claim 1, comprising a sequence UGAAAAAAACC (SEQ ID NO: 91), UGAAAGAAACC (SEQ ID NO: 92), UGAAAGAAACU (SEQ ID NO: 93), CGAACAAAACU (SEQ ID NO: 103), CGAAAGAAACU (SEQ ID NO: 104) or AGAAUGAAACU (SEQ ID NO: 102), wherein at least one nucleotide other than the 11th pyrimidine nucleotide of the aforementioned sequence is modified.

7. The aptamer according to claim 1, wherein the aptamer comprises from 1 to 20 nucleotides on the 5' end of the nucleotide sequence such that the length of the aptamer is 32 to 50 nucleotides.

8. The aptamer according to claim 1, wherein the aptamer comprises from 1 to 20 nucleotides on the 3' end of the nucleotide sequence such that the length of the aptamer is 32 to 50 nucleotides.

9. The aptamer according to claim 7, wherein the aptamer comprises from 1 to 20 nucleotides on the 3' end of the nucleotide sequence such that the length of the aptamer is 32 to 50 nucleotides.

10. The aptamer according to claim 1, wherein the modification of the 11th pyrimidine nucleotide is fluorination at 2'-, 3'-and/or 4'-position of the sugar residue.

11. The aptamer according to claim 1, wherein the modification of the 11th pyrimidine nucleotide is fluorination at 2'-position of the sugar residue.

12. A method of treating or preventing a disease accompanied by pain or inflammation caused by signaling via NGF and an NGF receptor comprising administering to a subject in need thereof an aptamer that binds to NGF and inhibits binding of NGF and an NGF receptor, comprising a nucleotide sequence of:

UGAAAAAAACC (SEQ ID NO: 91),
UGAAAGAAACC (SEQ ID NO: 92),
UGAAAGAAACU (SEQ ID NO: 93),
UGAAACAAACC (SEQ ID NO: 94),
UGAAAAGAACC (SEQ ID NO: 95),
UGAAAAAACCC (SEQ ID NO: 96),
UGAAAAAACCU (SEQ ID NO: 97),
UGAAAACAACC (SEQ ID NO: 98),
UGAAAUAAACC (SEQ ID NO: 99),
UGAAAUAAACU (SEQ ID NO: 100),
UGAAAAAAUCU (SEQ ID NO: 101),
AGAAUGAAACU (SEQ ID NO: 102),
CGAACAAAACU (SEQ ID NO: 103),
CGAAAGAAACU (SEQ ID NO: 104),
UGAAAGGAACC (SEQ ID NO: 105),
UGAAAAAAACY (SEQ ID NO: 110),
UGAAAGAAACY (SEQ ID NO: 111),
CGAACAAAACY (SEQ ID NO: 112), or
CGAAAGAAACY (SEQ ID NO: 113);

wherein Y is a pyrimidine nucleotide, wherein the 11th pyrimidine nucleotide (C, U or Y) of SEQ ID NOs: 91-105 and 110-113, is modified at 2'-, 3'- and/or 4'-position of the sugar residue, and wherein the modification is selected from the group consisting of fluorination, O-alkylation, O-arylation, S-alkylation, S-arylation, and amination, wherein the length of the aptamer is 32 nucleotides or more, and wherein the disease accompanied by pain or inflammation is selected from the group consisting of nociceptive pain, inflammatory pain, neuropathic pain, fibromyalgia pain, systemic lupus erythematosus, multiple sclerosis, psoriasis, osteoarthritis, chronic rheumatoid arthritis, interstitial cystitis, and asthma.

13. The method according to claim 12, wherein the modification of the 11th pyrimidine nucleotide of SEQ ID NOs: 91, 92 and 100 is fluorination at 2'-, 3'-and/or 4'-position of the sugar residue.

14. The method according to claim 12, wherein the modification of the 11th pyrimidine nucleotide of SEQ ID NOs: 91, 92 and 100 is fluorination at 2'-position of the sugar residue.

* * * * *

SEQUENCE LISTING

<160> NUMBER OF SEQ ID NOS: 128

<210> SEQ ID NO 1
<211> LENGTH: 79
<212> TYPE: RNA
<213> ORGANISM: Artificial Sequence
<220> FEATURE:
<223> OTHER INFORMATION: nucleic acid having binding activity against NGF

<400> SEQUENCE: 1

```
gggaagccug uggagcugca ggaugaaaaa aacccaaaaa caaagacaau gauugaguag    60
cauugucacc aacaacugg                                                 79
```

<210> SEQ ID NO 2
<211> LENGTH: 78
<212> TYPE: RNA
<213> ORGANISM: Artificial Sequence
<220> FEATURE:
<223> OTHER INFORMATION: nucleic acid having binding activity against NGF

<400> SEQUENCE: 2

```
gggaagccug uggagcugcc uacacuuuag uaugacaaac cuagagugua aaugcuucgc    60
auugucacca acaacugg                                                  78
```

<210> SEQ ID NO 3
<211> LENGTH: 79
<212> TYPE: RNA
<213> ORGANISM: Artificial Sequence
<220> FEATURE:
<223> OTHER INFORMATION: nucleic acid having binding activity against NGF

<400> SEQUENCE: 3

```
gggaagccug uggagcugca ggaugaaaaa aacccaaaau aaguagaaau gacagaaugg    60
cauugucacc aacaacugg                                                 79
```

<210> SEQ ID NO 4
<211> LENGTH: 79
<212> TYPE: RNA
<213> ORGANISM: Artificial Sequence
<220> FEATURE:
<223> OTHER INFORMATION: nucleic acid having binding activity against NGF

<400> SEQUENCE: 4

```
gggaagccug uggagcugca ggaugaaaaa aacccaaaua ugacaaauaa aacggcaacg    60
cauugucacc aacaacugg                                                 79
```

<210> SEQ ID NO 5
<211> LENGTH: 79
<212> TYPE: RNA
<213> ORGANISM: Artificial Sequence
<220> FEATURE:
<223> OTHER INFORMATION: nucleic acid having binding activity against NGF

<400> SEQUENCE: 5

```
gggaagccug uggagcugcu uaaacaagca agugaaaaaa accacagcaa auguaaaaag    60
cauugucacc aacaacugg                                                 79
```

<210> SEQ ID NO 6

```
<211> LENGTH: 79
<212> TYPE: RNA
<213> ORGANISM: Artificial Sequence
<220> FEATURE:
<223> OTHER INFORMATION: nucleic acid having binding activity against
      NGF

<400> SEQUENCE: 6
gggaagccug uggagcugca ggaugaaaaa aacccaaaau uaaauaaaaa auagacggug    60
cauugucacc aacaacugg                                                79

<210> SEQ ID NO 7
<211> LENGTH: 79
<212> TYPE: RNA
<213> ORGANISM: Artificial Sequence
<220> FEATURE:
<223> OTHER INFORMATION: nucleic acid having binding activity against
      NGF

<400> SEQUENCE: 7
gggaagccug uggagcugca ggaugaaaaa aacccaaaau uagauaaaaa auagacggug    60
cauugucacc aacaacugg                                                79

<210> SEQ ID NO 8
<211> LENGTH: 78
<212> TYPE: RNA
<213> ORGANISM: Artificial Sequence
<220> FEATURE:
<223> OTHER INFORMATION: nucleic acid having binding activity against
      NGF

<400> SEQUENCE: 8
gggaagccug uggagcugcg gauaaaaaua gaguuugaua aacaccugua uuaaaaccgc    60
auugucacca acaacugg                                                 78

<210> SEQ ID NO 9
<211> LENGTH: 79
<212> TYPE: RNA
<213> ORGANISM: Artificial Sequence
<220> FEATURE:
<223> OTHER INFORMATION: nucleic acid having binding activity against
      NGF

<400> SEQUENCE: 9
gggaagccug uggagcugcu ccacaaggau gaaaaaaacc caaauaauau auuuaaucag    60
cauugucacc aacaacugg                                                79

<210> SEQ ID NO 10
<211> LENGTH: 79
<212> TYPE: RNA
<213> ORGANISM: Artificial Sequence
<220> FEATURE:
<223> OTHER INFORMATION: nucleic acid having binding activity against
      NGF

<400> SEQUENCE: 10
gggaagccug uggagcugca ggaugaaaaa aacccaaauu aaagagcuug acaaaacaug    60
cauugucacc aacaacugg                                                79

<210> SEQ ID NO 11
<211> LENGTH: 80
<212> TYPE: RNA
<213> ORGANISM: Artificial Sequence
<220> FEATURE:
```

```
<223> OTHER INFORMATION: nucleic acid having binding activity against
      NGF

<400> SEQUENCE: 11
gggaagccug uggagcugcu ccacaaggau gaaaaaaaac ccaaauaaua uauuuaauca    60
gcauugucac caacaacugg                                               80

<210> SEQ ID NO 12
<211> LENGTH: 79
<212> TYPE: RNA
<213> ORGANISM: Artificial Sequence
<220> FEATURE:
<223> OTHER INFORMATION: nucleic acid having binding activity against
      NGF

<400> SEQUENCE: 12
gggaagccug uggagcugcg aaacagugaa acaaaccaca gacugagaaa gcaguaacag    60
cauugucacc aacaacugg                                                79

<210> SEQ ID NO 13
<211> LENGTH: 82
<212> TYPE: RNA
<213> ORGANISM: Artificial Sequence
<220> FEATURE:
<223> OTHER INFORMATION: nucleic acid having binding activity against
      NGF

<400> SEQUENCE: 13
gggaagccug uggagcugca ggaugaaaaa aacccaaaau uaaauaaaaa aaaauggacg    60
gugcauuguc accaacaacu gg                                            82

<210> SEQ ID NO 14
<211> LENGTH: 77
<212> TYPE: RNA
<213> ORGANISM: Artificial Sequence
<220> FEATURE:
<223> OTHER INFORMATION: nucleic acid having binding activity against
      NGF

<400> SEQUENCE: 14
gggaagccug uggagcugcu gaauuggaua cagauaguug aaaaaaacca augaucagca    60
uugucaccaa caacugg                                                  77

<210> SEQ ID NO 15
<211> LENGTH: 79
<212> TYPE: RNA
<213> ORGANISM: Artificial Sequence
<220> FEATURE:
<223> OTHER INFORMATION: nucleic acid having binding activity against
      NGF

<400> SEQUENCE: 15
gggaagccug uggagcugcu ccacaaggau gaaaaaaacc caaauaauau auuugaucag    60
cauugucacc aacaacugg                                                79

<210> SEQ ID NO 16
<211> LENGTH: 80
<212> TYPE: RNA
<213> ORGANISM: Artificial Sequence
<220> FEATURE:
<223> OTHER INFORMATION: nucleic acid having binding activity against
      NGF

<400> SEQUENCE: 16
```
gggaagccug uggagcugcu ccacaaggau gaaaaaaacc ccaaauaaug uauuuaauca    60
gcauugucac caacaacugg                                               80

<210> SEQ ID NO 17
<211> LENGTH: 79
<212> TYPE: RNA
<213> ORGANISM: Artificial Sequence
<220> FEATURE:
<223> OTHER INFORMATION: nucleic acid having binding activity against
      NGF

<400> SEQUENCE: 17
gggaagccug uggagcugca ggauggaaaa aacccaaaau aaguagaaau gacagaaugg    60
cauugucacc aacaacugg                                                79

<210> SEQ ID NO 18
<211> LENGTH: 80
<212> TYPE: RNA
<213> ORGANISM: Artificial Sequence
<220> FEATURE:
<223> OTHER INFORMATION: nucleic acid having binding activity against
      NGF

<400> SEQUENCE: 18
gggaagccug uggagcugcc gaaauggacu guaaagcaug aaaaaaacca uucaaucgag    60
gcauugucac caacaacugg                                               80

<210> SEQ ID NO 19
<211> LENGTH: 80
<212> TYPE: RNA
<213> ORGANISM: Artificial Sequence
<220> FEATURE:
<223> OTHER INFORMATION: nucleic acid having binding activity against
      NGF

<400> SEQUENCE: 19
gggaagccug uggagcugca ggaugaaaaa aacccaaacu aaaguuuaaa acugauacga    60
gcauugucac caacaacugg                                               80

<210> SEQ ID NO 20
<211> LENGTH: 73
<212> TYPE: RNA
<213> ORGANISM: Artificial Sequence
<220> FEATURE:
<223> OTHER INFORMATION: nucleic acid having binding activity against
      NGF

<400> SEQUENCE: 20
gggaagccug uggagcugca ggaugaaaaa aacccaaauu aaaaacuugc cgagcauugu    60
caccaacaac ugg                                                      73

<210> SEQ ID NO 21
<211> LENGTH: 80
<212> TYPE: RNA
<213> ORGANISM: Artificial Sequence
<220> FEATURE:
<223> OTHER INFORMATION: nucleic acid having binding activity against
      NGF

<400> SEQUENCE: 21
gggaagccug uggagcugca ggaugaaaaa aacccaaaa acaaagacaa cgauugagua    60
gcauugucac caacaacugg                                               80

<210> SEQ ID NO 22
<211> LENGTH: 79
<212> TYPE: RNA
<213> ORGANISM: Artificial Sequence
<220> FEATURE:
<223> OTHER INFORMATION: nucleic acid having binding activity against
      NGF

<400> SEQUENCE: 22
gggaagccug uggagcugca ggaugaaaaa aacccaaaau uguccacaga aaauggauug    60
cauugucacc aacaacugg                                                79

<210> SEQ ID NO 23
<211> LENGTH: 79
<212> TYPE: RNA
<213> ORGANISM: Artificial Sequence
<220> FEATURE:
<223> OTHER INFORMATION: nucleic acid having binding activity against
      NGF

<400> SEQUENCE: 23
gggaagccug uggagcugcg aaacagugaa acaaaccaca gacugagaaa gcaguaaaag    60
cauugucacc aacaacugg                                                79

<210> SEQ ID NO 24
<211> LENGTH: 69
<212> TYPE: RNA
<213> ORGANISM: Artificial Sequence
<220> FEATURE:
<223> OTHER INFORMATION: nucleic acid having binding activity against
      NGF

<400> SEQUENCE: 24
gggaagccug uggagcugcc uacacuuuag uaugacaaac cuagagugua aaugcuucgc    60
auugucacc                                                           69

<210> SEQ ID NO 25
<211> LENGTH: 47
<212> TYPE: RNA
<213> ORGANISM: Artificial Sequence
<220> FEATURE:
<223> OTHER INFORMATION: nucleic acid having binding activity against
      NGF

<400> SEQUENCE: 25
ggagcugccu acacuuuagu augacaaacc uagaguguaa augcuuc                 47

<210> SEQ ID NO 26
<211> LENGTH: 46
<212> TYPE: RNA
<213> ORGANISM: Artificial Sequence
<220> FEATURE:
<223> OTHER INFORMATION: nucleic acid having binding activity against
      NGF

<400> SEQUENCE: 26
gggcugugga gcugcuuaaa caagcaagug aaaaaaacca cagccc                  46

<210> SEQ ID NO 27
<211> LENGTH: 45
<212> TYPE: RNA
<213> ORGANISM: Artificial Sequence
<220> FEATURE:
<223> OTHER INFORMATION: nucleic acid having binding activity against

NGF

<400> SEQUENCE: 27
gggaagccug uggagcugca ggaugaaaaa aacccaaaau uaaau          45

<210> SEQ ID NO 28
<211> LENGTH: 40
<212> TYPE: RNA
<213> ORGANISM: Artificial Sequence
<220> FEATURE:
<223> OTHER INFORMATION: nucleic acid having binding activity against
      NGF

<400> SEQUENCE: 28
gggaagccug uggagcugca ggaugaaaaa aacccaaaau          40

<210> SEQ ID NO 29
<211> LENGTH: 61
<212> TYPE: RNA
<213> ORGANISM: Artificial Sequence
<220> FEATURE:
<223> OTHER INFORMATION: nucleic acid having binding activity against
      NGF

<400> SEQUENCE: 29
gguggagcug cggauaaaaa uagaguuuga uaaacaccug uauuaaaacc gcauugucac          60
c                                                                         61

<210> SEQ ID NO 30
<211> LENGTH: 41
<212> TYPE: RNA
<213> ORGANISM: Artificial Sequence
<220> FEATURE:
<223> OTHER INFORMATION: nucleic acid having binding activity against
      NGF

<400> SEQUENCE: 30
gggauaaaaa uagaguuuga uaaacaccug uauuaaaacc c          41

<210> SEQ ID NO 31
<211> LENGTH: 34
<212> TYPE: RNA
<213> ORGANISM: Artificial Sequence
<220> FEATURE:
<223> OTHER INFORMATION: nucleic acid having binding activity against
      NGF

<400> SEQUENCE: 31
gggagcugcu uaaacaagca agugaaaaaa accc          34

<210> SEQ ID NO 32
<211> LENGTH: 38
<212> TYPE: RNA
<213> ORGANISM: Artificial Sequence
<220> FEATURE:
<223> OTHER INFORMATION: nucleic acid having binding activity against
      NGF

<400> SEQUENCE: 32
uguggagcug cuuaaacaag caagugaaaa aaaccaca          38

<210> SEQ ID NO 33
<211> LENGTH: 36
<212> TYPE: RNA
<213> ORGANISM: Artificial Sequence
<220> FEATURE:

```
<223> OTHER INFORMATION: nucleic acid having binding activity against
      NGF

<400> SEQUENCE: 33
uguggagcug cuaaacagca agugaaaaaa accaca                                36

<210> SEQ ID NO 34
<211> LENGTH: 34
<212> TYPE: RNA
<213> ORGANISM: Artificial Sequence
<220> FEATURE:
<223> OTHER INFORMATION: nucleic acid having binding activity against
      NGF

<400> SEQUENCE: 34
guggagcugu uaaacaacaa gugaaaaaaa ccac                                  34

<210> SEQ ID NO 35
<211> LENGTH: 38
<212> TYPE: RNA
<213> ORGANISM: Artificial Sequence
<220> FEATURE:
<223> OTHER INFORMATION: nucleic acid having binding activity against
      NGF

<400> SEQUENCE: 35
gggaagccug uggagcugca ggaugaaaaa aacccaaa                              38

<210> SEQ ID NO 36
<211> LENGTH: 35
<212> TYPE: RNA
<213> ORGANISM: Artificial Sequence
<220> FEATURE:
<223> OTHER INFORMATION: nucleic acid having binding activity against
      NGF

<400> SEQUENCE: 36
gggaagccug uggagcugca ggaugaaaaa aaccc                                 35

<210> SEQ ID NO 37
<211> LENGTH: 74
<212> TYPE: RNA
<213> ORGANISM: Artificial Sequence
<220> FEATURE:
<223> OTHER INFORMATION: nucleic acid having binding activity against
      NGF

<400> SEQUENCE: 37
gggagaacuu cgaccagaag uuugaaagaa acccaaaggu gaaacaacaa uaugugcgca      60
uacauggauc cuca                                                        74

<210> SEQ ID NO 38
<211> LENGTH: 74
<212> TYPE: RNA
<213> ORGANISM: Artificial Sequence
<220> FEATURE:
<223> OTHER INFORMATION: nucleic acid having binding activity against
      NGF

<400> SEQUENCE: 38
gggagaacuu cgaccagaag agaaugaaac uccacaaagu acauaaaaca uaugugcgca      60
uacauggauc cuca                                                        74

<210> SEQ ID NO 39
<211> LENGTH: 74
```

<212> TYPE: RNA
<213> ORGANISM: Artificial Sequence
<220> FEATURE:
<223> OTHER INFORMATION: nucleic acid having binding activity against
      NGF

<400> SEQUENCE: 39
gggagaacuu cgaccagaag ugugaaaaga acccaaauaa aacaacaaug uaugugcgca    60
uacauggauc cuca                                                      74

<210> SEQ ID NO 40
<211> LENGTH: 74
<212> TYPE: RNA
<213> ORGANISM: Artificial Sequence
<220> FEATURE:
<223> OTHER INFORMATION: nucleic acid having binding activity against
      NGF

<400> SEQUENCE: 40
gggagaacuu cgaccagaag uuugaaaaaa acccaggaaa auggaagacg uaugugcgca    60
uacauggauc cuca                                                      74

<210> SEQ ID NO 41
<211> LENGTH: 74
<212> TYPE: RNA
<213> ORGANISM: Artificial Sequence
<220> FEATURE:
<223> OTHER INFORMATION: nucleic acid having binding activity against
      NGF

<400> SEQUENCE: 41
gggagaacuu cgaccagaag uuugaaagga acccaaagcg aaacaaaacg uaugugcgca    60
uacauggauc cuca                                                      74

<210> SEQ ID NO 42
<211> LENGTH: 74
<212> TYPE: RNA
<213> ORGANISM: Artificial Sequence
<220> FEATURE:
<223> OTHER INFORMATION: nucleic acid having binding activity against
      NGF

<400> SEQUENCE: 42
gggagaacuu cgaccagaag uuugaaaaaa acccaaaaga gcagcagaga uaugugcgca    60
uacauggauc cuca                                                      74

<210> SEQ ID NO 43
<211> LENGTH: 73
<212> TYPE: RNA
<213> ORGANISM: Artificial Sequence
<220> FEATURE:
<223> OTHER INFORMATION: nucleic acid having binding activity against
      NGF

<400> SEQUENCE: 43
gggagaacuu cgaccagaag cuugaaaaaa ccccaauaug agaaucauau augugcgcau    60
acauggaucc uca                                                       73

<210> SEQ ID NO 44
<211> LENGTH: 73
<212> TYPE: RNA
<213> ORGANISM: Artificial Sequence
<220> FEATURE:
<223> OTHER INFORMATION: nucleic acid having binding activity against

```
                              NGF

<400> SEQUENCE: 44
ggggaacuuc gaccagaagu uugaaagaaa cccaaaauua gcaccauaau augugcgcau      60
acauggaucc uca                                                        73

<210> SEQ ID NO 45
<211> LENGTH: 74
<212> TYPE: RNA
<213> ORGANISM: Artificial Sequence
<220> FEATURE:
<223> OTHER INFORMATION: nucleic acid having binding activity against
      NGF

<400> SEQUENCE: 45
gggagaacuu cgaccagaag agaaugaaac ucccaaauca aggacaauga uaugugcgca      60
uacauggauc uca                                                        74

<210> SEQ ID NO 46
<211> LENGTH: 74
<212> TYPE: RNA
<213> ORGANISM: Artificial Sequence
<220> FEATURE:
<223> OTHER INFORMATION: nucleic acid having binding activity against
      NGF

<400> SEQUENCE: 46
gggagaacuu cgaccagaag uuugaaacaa acccaaaguu acgcacaaaa uaugugcgca      60
uacauggauc cuca                                                       74

<210> SEQ ID NO 47
<211> LENGTH: 74
<212> TYPE: RNA
<213> ORGANISM: Artificial Sequence
<220> FEATURE:
<223> OTHER INFORMATION: nucleic acid having binding activity against
      NGF

<400> SEQUENCE: 47
gggagaacuu cgaccagaag aaguuugaaa agaacccaaa augagcaaaa uaugugcgca      60
uacauggauc cuca                                                       74

<210> SEQ ID NO 48
<211> LENGTH: 74
<212> TYPE: RNA
<213> ORGANISM: Artificial Sequence
<220> FEATURE:
<223> OTHER INFORMATION: nucleic acid having binding activity against
      NGF

<400> SEQUENCE: 48
gggagaacuu cgaccagaag uuugaaaaga acccgaaaaa cgcauaauaa uaugugcgca      60
uacauggauc cuca                                                       74

<210> SEQ ID NO 49
<211> LENGTH: 74
<212> TYPE: RNA
<213> ORGANISM: Artificial Sequence
<220> FEATURE:
<223> OTHER INFORMATION: nucleic acid having binding activity against
      NGF

<400> SEQUENCE: 49
```
gggagaacuu cgaccagaag ugaaagaaac ucccaagacg guaacgaaag uaugugcgca    60
uacauggauc cuca    74

<210> SEQ ID NO 50
<211> LENGTH: 74
<212> TYPE: RNA
<213> ORGANISM: Artificial Sequence
<220> FEATURE:
<223> OTHER INFORMATION: nucleic acid having binding activity against
      NGF

<400> SEQUENCE: 50
gggagaacuu cgaccagaag ugaaaaaacc ucccaauaca aacacaaaaa uaugugcgca    60
uacauggauc cuca    74

<210> SEQ ID NO 51
<211> LENGTH: 77
<212> TYPE: RNA
<213> ORGANISM: Artificial Sequence
<220> FEATURE:
<223> OTHER INFORMATION: nucleic acid having binding activity against
      NGF

<400> SEQUENCE: 51
gggagaacuu cgaccagaag uuugaaagaa acccaaaaaa acaacauaug aacuaugugc    60
gcauacaugg auccuca    77

<210> SEQ ID NO 52
<211> LENGTH: 73
<212> TYPE: RNA
<213> ORGANISM: Artificial Sequence
<220> FEATURE:
<223> OTHER INFORMATION: nucleic acid having binding activity against
      NGF

<400> SEQUENCE: 52
gggagaacuu cgaccagaag uuugaaagaa acccaaauau acaaaacacu augugcgcau    60
acauggaucc uca    73

<210> SEQ ID NO 53
<211> LENGTH: 74
<212> TYPE: RNA
<213> ORGANISM: Artificial Sequence
<220> FEATURE:
<223> OTHER INFORMATION: nucleic acid having binding activity against
      NGF

<400> SEQUENCE: 53
gggagaacuu cgaccagaag uuugaaagga acccaaaaac acaaaauguc uaugugcgca    60
uacauggauc cuca    74

<210> SEQ ID NO 54
<211> LENGTH: 74
<212> TYPE: RNA
<213> ORGANISM: Artificial Sequence
<220> FEATURE:
<223> OTHER INFORMATION: nucleic acid having binding activity against
      NGF

<400> SEQUENCE: 54
gggagaacuu cgaccagaag ucgaaaguga aagaaacucc aacgaaagca uaugugcgca    60
uacauggauc cuca    74

<210> SEQ ID NO 55
<211> LENGTH: 72
<212> TYPE: RNA
<213> ORGANISM: Artificial Sequence
<220> FEATURE:
<223> OTHER INFORMATION: nucleic acid having binding activity against NGF

<400> SEQUENCE: 55
gggagaacuu cgaccagaag uuugaaagaa acccaaaaau gaaugcaacu augugcgcau    60
acauggaccu ca    72

<210> SEQ ID NO 56
<211> LENGTH: 74
<212> TYPE: RNA
<213> ORGANISM: Artificial Sequence
<220> FEATURE:
<223> OTHER INFORMATION: nucleic acid having binding activity against NGF

<400> SEQUENCE: 56
gggagaacuu cgaccagaag ugaaagaaac ucccaacaca aaugcacaac uaugugcgca    60
uacauggauc cuca    74

<210> SEQ ID NO 57
<211> LENGTH: 75
<212> TYPE: RNA
<213> ORGANISM: Artificial Sequence
<220> FEATURE:
<223> OTHER INFORMATION: nucleic acid having binding activity against NGF

<400> SEQUENCE: 57
gggagaacuu cgaccagaag uuugaaaaaa acccaaacac cgaagcacaa auaugugcgc    60
auacauggau ccuca    75

<210> SEQ ID NO 58
<211> LENGTH: 74
<212> TYPE: RNA
<213> ORGANISM: Artificial Sequence
<220> FEATURE:
<223> OTHER INFORMATION: nucleic acid having binding activity against NGF

<400> SEQUENCE: 58
gggagaacuu cgaccagaag uuugaaaaga acccaaauac agaauaaaug uaugugcgca    60
uacauggauc cuca    74

<210> SEQ ID NO 59
<211> LENGTH: 74
<212> TYPE: RNA
<213> ORGANISM: Artificial Sequence
<220> FEATURE:
<223> OTHER INFORMATION: nucleic acid having binding activity against NGF

<400> SEQUENCE: 59
gggagaacuu cgaccagaag ucgaaacguu ugaaaaaaac ccaaggagga uaugugcgca    60
uacauggauc cuca    74

<210> SEQ ID NO 60
<211> LENGTH: 74
<212> TYPE: RNA

<213> ORGANISM: Artificial Sequence
<220> FEATURE:
<223> OTHER INFORMATION: nucleic acid having binding activity against NGF

<400> SEQUENCE: 60
gggagaacuu cgaccagagg auuugaaaaa aacccgaaua aagauaacag uaugugcgca    60
uacauggauc cuca    74

<210> SEQ ID NO 61
<211> LENGTH: 74
<212> TYPE: RNA
<213> ORGANISM: Artificial Sequence
<220> FEATURE:
<223> OTHER INFORMATION: nucleic acid having binding activity against NGF

<400> SEQUENCE: 61
gggagaacuu cgaccagaag gucguaacga auaaaacucc ugcacaaaaa uaugugcgca    60
uacauggauc cuca    74

<210> SEQ ID NO 62
<211> LENGTH: 74
<212> TYPE: RNA
<213> ORGANISM: Artificial Sequence
<220> FEATURE:
<223> OTHER INFORMATION: nucleic acid having binding activity against NGF

<400> SEQUENCE: 62
gggagaacuu cgaccagaag uuugaaagaa acccaaauua aagugaacag uaugugcgca    60
uacauggauc cuca    74

<210> SEQ ID NO 63
<211> LENGTH: 74
<212> TYPE: RNA
<213> ORGANISM: Artificial Sequence
<220> FEATURE:
<223> OTHER INFORMATION: nucleic acid having binding activity against NGF

<400> SEQUENCE: 63
gggagaacuu cgaccagaag auuugaaaga aacccaaacu aagcacaaaa uaugugcgca    60
uacauggauc cuca    74

<210> SEQ ID NO 64
<211> LENGTH: 74
<212> TYPE: RNA
<213> ORGANISM: Artificial Sequence
<220> FEATURE:
<223> OTHER INFORMATION: nucleic acid having binding activity against NGF

<400> SEQUENCE: 64
gggagaacuu cgaccagaag uuugaaagaa acccaaaaca uuagcacaca uaugugcgca    60
uacauggauc cuca    74

<210> SEQ ID NO 65
<211> LENGTH: 74
<212> TYPE: RNA
<213> ORGANISM: Artificial Sequence
<220> FEATURE:
<223> OTHER INFORMATION: nucleic acid having binding activity against NGF

<400> SEQUENCE: 65
gggagaacuu cgaccagaag ugugaaaaaa acccaaaucg agcacaaaau uaugugcgca        60
uacauggauc cuca                                                         74

<210> SEQ ID NO 66
<211> LENGTH: 74
<212> TYPE: RNA
<213> ORGANISM: Artificial Sequence
<220> FEATURE:
<223> OTHER INFORMATION: nucleic acid having binding activity against
      NGF

<400> SEQUENCE: 66
gggagaacuu cgaccagaag uuugaaaaaa acccaaagca agcacaacau uaugugcgca        60
uacauggauc cuca                                                         74

<210> SEQ ID NO 67
<211> LENGTH: 74
<212> TYPE: RNA
<213> ORGANISM: Artificial Sequence
<220> FEATURE:
<223> OTHER INFORMATION: nucleic acid having binding activity against
      NGF

<400> SEQUENCE: 67
gggagaacuu cgaccagaag ucauaacga acaaaacucc caaggaaua uaugugcgca         60 uacauggauc cuca                                                         74

<210> SEQ ID NO 68
<211> LENGTH: 74
<212> TYPE: RNA
<213> ORGANISM: Artificial Sequence
<220> FEATURE:
<223> OTHER INFORMATION: nucleic acid having binding activity against
      NGF

<400> SEQUENCE: 68
gggagaacuu cgaccagaag ucgagagcga aagaaacucc caaaacacag uaugugcgca        60
uacauggauc cuca                                                         74

<210> SEQ ID NO 69
<211> LENGTH: 83
<212> TYPE: DNA
<213> ORGANISM: Artificial Sequence
<220> FEATURE:
<223> OTHER INFORMATION: nucleic acid having binding activity against
      NGF
<220> FEATURE:
<221> NAME/KEY: misc_feature
<223> OTHER INFORMATION: DNA/RNA binding molecule

<400> SEQUENCE: 69
gggagaggca agaatagggc ccagctgaaa aaaacctgga cgtacaccgt tcgccgagcg        60
ggtgaagaga agagacatta gga                                               83

<210> SEQ ID NO 70
<211> LENGTH: 82
<212> TYPE: DNA
<213> ORGANISM: Artificial Sequence
<220> FEATURE:
<223> OTHER INFORMATION: nucleic acid having binding activity against
      NGF
<220> FEATURE:

<221> NAME/KEY: misc_feature
<223> OTHER INFORMATION: DNA/RNA binding molecule

<400> SEQUENCE: 70
gggagaggca agaatagggc tggaaataga accgcgctgt cttcattaag ccgcccaacg    60
gtgaagagaa gagacattag ga                                            82

<210> SEQ ID NO 71
<211> LENGTH: 82
<212> TYPE: DNA
<213> ORGANISM: Artificial Sequence
<220> FEATURE:
<223> OTHER INFORMATION: nucleic acid having binding activity against
      NGF
<220> FEATURE:
<221> NAME/KEY: misc_feature
<223> OTHER INFORMATION: DNA/RNA binding molecule

<400> SEQUENCE: 71
gggagaggca agaatagggc acttgaaaaa aacccaaatt taccgtcttc agcgtcgggt    60
gtgaagagaa gagacattag ga                                            82

<210> SEQ ID NO 72
<211> LENGTH: 82
<212> TYPE: DNA
<213> ORGANISM: Artificial Sequence
<220> FEATURE:
<223> OTHER INFORMATION: nucleic acid having binding activity against
      NGF
<220> FEATURE:
<221> NAME/KEY: misc_feature
<223> OTHER INFORMATION: DNA/RNA binding molecule

<400> SEQUENCE: 72
gggagaggca agaatagggc tggatgggca gtaacctgaa aaaaccacc cacctctacc    60 gtgaagagaa gagacattag ga                                            82

<210> SEQ ID NO 73
<211> LENGTH: 81
<212> TYPE: DNA
<213> ORGANISM: Artificial Sequence
<220> FEATURE:
<223> OTHER INFORMATION: nucleic acid having binding activity against
      NGF
<220> FEATURE:
<221> NAME/KEY: misc_feature
<223> OTHER INFORMATION: DNA/RNA binding molecule

<400> SEQUENCE: 73
gggagaggca agaatagggc acttgaaaaa aacccaaaga aagaatactt acccggcgcg    60
tgaagagaag agacattagg a                                             81

<210> SEQ ID NO 74
<211> LENGTH: 82
<212> TYPE: DNA
<213> ORGANISM: Artificial Sequence
<220> FEATURE:
<223> OTHER INFORMATION: nucleic acid having binding activity against
      NGF
<220> FEATURE:
<221> NAME/KEY: misc_feature
<223> OTHER INFORMATION: DNA/RNA binding molecule

<400> SEQUENCE: 74
gggagaggca agaatagggc atagtgtaga cccctctcaa gatacccat gaattgcccc    60

```
gtgaagagaa gagacattag ga                                              82

<210> SEQ ID NO 75
<211> LENGTH: 78
<212> TYPE: RNA
<213> ORGANISM: Artificial Sequence
<220> FEATURE:
<223> OTHER INFORMATION: nucleic acid having binding activity against
      NGF

<400> SEQUENCE: 75
gggagaacuu cgaccagaag ugaaagaauc uccaaagaca agauaaaaac aaccguaugu    60
gcgcauacau ggauccuc                                                  78

<210> SEQ ID NO 76
<211> LENGTH: 78
<212> TYPE: RNA
<213> ORGANISM: Artificial Sequence
<220> FEATURE:
<223> OTHER INFORMATION: nucleic acid having binding activity against
      NGF

<400> SEQUENCE: 76
gggagaacuu cgaccagaag gauaaacgca uguauuugca guauuaaaaa ugccuuaugu    60
gcgcauacau ggauccuc                                                  78

<210> SEQ ID NO 77
<211> LENGTH: 78
<212> TYPE: RNA
<213> ORGANISM: Artificial Sequence
<220> FEATURE:
<223> OTHER INFORMATION: nucleic acid having binding activity against
      NGF

<400> SEQUENCE: 77
gggagaacuu cgaccagaag ugaaaaaauc uccaguugca agacgaaaca aaccuuaugu    60
gcgcauacau ggauccuc                                                  78

<210> SEQ ID NO 78
<211> LENGTH: 78
<212> TYPE: DNA
<213> ORGANISM: Artificial Sequence
<220> FEATURE:
<223> OTHER INFORMATION: nucleic acid having binding activity against
      NGF

<400> SEQUENCE: 78
gggagaacuu cgaccagaag uguguauugu ucagggugug cccagccuau aaccauaugu    60
gcgcauacau ggauccuc                                                  78

<210> SEQ ID NO 79
<211> LENGTH: 78
<212> TYPE: RNA
<213> ORGANISM: Artificial Sequence
<220> FEATURE:
<223> OTHER INFORMATION: nucleic acid having binding activity against
      NGF

<400> SEQUENCE: 79
gggagaacuu cgaccagaag gauagccaug uggaggugaa gacugaaaua aaccauaugu    60
gcgcauacau ggauccuc                                                  78

<210> SEQ ID NO 80
```

```
<211> LENGTH: 78
<212> TYPE: RNA
<213> ORGANISM: Artificial Sequence
<220> FEATURE:
<223> OTHER INFORMATION: nucleic acid having binding activity against
      NGF

<400> SEQUENCE: 80
gggagaacuu cgaccagaag ugaaacaac cucccaauaa ugaucacaga aauccuaugu      60
gcgcauacau ggauccuc                                                  78

<210> SEQ ID NO 81
<211> LENGTH: 78
<212> TYPE: RNA
<213> ORGANISM: Artificial Sequence
<220> FEATURE:
<223> OTHER INFORMATION: nucleic acid having binding activity against
      NGF

<400> SEQUENCE: 81
gggagaacuu cgaccagaag gagaugacug uguaaccaca guaugaaaua aacucuaugu    60
gcgcauacau ggauccuc                                                  78

<210> SEQ ID NO 82
<211> LENGTH: 78
<212> TYPE: RNA
<213> ORGANISM: Artificial Sequence
<220> FEATURE:
<223> OTHER INFORMATION: nucleic acid having binding activity against
      NGF

<400> SEQUENCE: 82
gggagaacuu cgaccagaag aggaugcuug uuugguuaca agcugaaaga aaccuuaugu    60
gcgcauacau ggauccuc                                                  78

<210> SEQ ID NO 83
<211> LENGTH: 79
<212> TYPE: RNA
<213> ORGANISM: Artificial Sequence
<220> FEATURE:
<223> OTHER INFORMATION: nucleic acid having binding activity against
      NGF

<400> SEQUENCE: 83
gggagaacuu cgaccagaag uugaagcuug aaaaaaaccc aggauuaaac agacaguaug    60
ugcgcauaca uggauccuc                                                 79

<210> SEQ ID NO 84
<211> LENGTH: 78
<212> TYPE: RNA
<213> ORGANISM: Artificial Sequence
<220> FEATURE:
<223> OTHER INFORMATION: nucleic acid having binding activity against
      NGF

<400> SEQUENCE: 84
gggagaacuu cgaccagaag ugaaagaaac ucccgaugaa agauguaaca aaccauaugu    60
gcgcauacau ggauccuc                                                  78

<210> SEQ ID NO 85
<211> LENGTH: 78
<212> TYPE: RNA
<213> ORGANISM: Artificial Sequence
<220> FEATURE:
```

```
<223> OTHER INFORMATION: nucleic acid having binding activity against
      NGF

<400> SEQUENCE: 85
gggagaacuu cgaccagaag cggaagccug cguaaccgca ggaugaaaac aaccguaugu    60
gcgcauacau ggauccuc                                                 78

<210> SEQ ID NO 86
<211> LENGTH: 78
<212> TYPE: RNA
<213> ORGANISM: Artificial Sequence
<220> FEATURE:
<223> OTHER INFORMATION: nucleic acid having binding activity against
      NGF

<400> SEQUENCE: 86
gggagaacuu cgaccagaag gaguagccag ugaaccugga auaugaaaaa aaccuuaugu    60
gcgcauacau ggauccuc                                                 78

<210> SEQ ID NO 87
<211> LENGTH: 71
<212> TYPE: DNA
<213> ORGANISM: Artificial Sequence
<220> FEATURE:
<223> OTHER INFORMATION: nucleic acid having binding activity against
      NGF

<400> SEQUENCE: 87
gggatcgaca gggctgcagc actggcgtag gttggaatat gggtattttt gtggtccgag    60
tcgtgccatc t                                                        71

<210> SEQ ID NO 88
<211> LENGTH: 33
<212> TYPE: RNA
<213> ORGANISM: Artificial Sequence
<220> FEATURE:
<223> OTHER INFORMATION: nucleic acid having binding activity against
      NGF

<400> SEQUENCE: 88
gggaagccgu ggagcugcgg augaaaaaaa ccc                                33

<210> SEQ ID NO 89
<211> LENGTH: 34
<212> TYPE: RNA
<213> ORGANISM: Artificial Sequence
<220> FEATURE:
<223> OTHER INFORMATION: nucleic acid having binding activity against
      NGF

<400> SEQUENCE: 89
gggaagccug uaaacagcag gaugaaaaaa accc                               34

<210> SEQ ID NO 90
<211> LENGTH: 32
<212> TYPE: RNA
<213> ORGANISM: Artificial Sequence
<220> FEATURE:
<223> OTHER INFORMATION: nucleic acid having binding activity against
      NGF

<400> SEQUENCE: 90
gggagccugu aaacagcagg ugaaaaaaac cc                                 32
```

-continued

```
<210> SEQ ID NO 91
<211> LENGTH: 11
<212> TYPE: RNA
<213> ORGANISM: Artificial
<220> FEATURE:
<223> OTHER INFORMATION: consensus sequence

<400> SEQUENCE: 91
ugaaaaaaac c                                                              11

<210> SEQ ID NO 92
<211> LENGTH: 11
<212> TYPE: RNA
<213> ORGANISM: Artificial
<220> FEATURE:
<223> OTHER INFORMATION: consensus sequence

<400> SEQUENCE: 92
ugaaagaaac c                                                              11

<210> SEQ ID NO 93
<211> LENGTH: 11
<212> TYPE: RNA
<213> ORGANISM: Artificial
<220> FEATURE:
<223> OTHER INFORMATION: consensus sequence

<400> SEQUENCE: 93
ugaaagaaac u                                                              11

<210> SEQ ID NO 94
<211> LENGTH: 11
<212> TYPE: RNA
<213> ORGANISM: Artificial
<220> FEATURE:
<223> OTHER INFORMATION: consensus sequence

<400> SEQUENCE: 94
ugaaacaaac c                                                              11

<210> SEQ ID NO 95
<211> LENGTH: 11
<212> TYPE: RNA
<213> ORGANISM: Artificial
<220> FEATURE:
<223> OTHER INFORMATION: consensus sequence

<400> SEQUENCE: 95
ugaaaagaac c                                                              11

<210> SEQ ID NO 96
<211> LENGTH: 11
<212> TYPE: RNA
<213> ORGANISM: Artificial
<220> FEATURE:
<223> OTHER INFORMATION: consensus sequence

<400> SEQUENCE: 96
ugaaaaaacc c                                                              11

<210> SEQ ID NO 97
<211> LENGTH: 11
<212> TYPE: RNA
<213> ORGANISM: Artificial
<220> FEATURE:
<223> OTHER INFORMATION: consensus sequence
```

```
<400> SEQUENCE: 97
ugaaaaaacc u                                                    11

<210> SEQ ID NO 98
<211> LENGTH: 11
<212> TYPE: RNA
<213> ORGANISM: Artificial
<220> FEATURE:
<223> OTHER INFORMATION: consensus sequence

<400> SEQUENCE: 98
ugaaaacaac c                                                    11

<210> SEQ ID NO 99
<211> LENGTH: 11
<212> TYPE: RNA
<213> ORGANISM: Artificial
<220> FEATURE:
<223> OTHER INFORMATION: consensus sequence

<400> SEQUENCE: 99
ugaaauaaac c                                                    11

<210> SEQ ID NO 100
<211> LENGTH: 11
<212> TYPE: RNA
<213> ORGANISM: Artificial
<220> FEATURE:
<223> OTHER INFORMATION: consensus sequence

<400> SEQUENCE: 100
ugaaauaaac u                                                    11

<210> SEQ ID NO 101
<211> LENGTH: 11
<212> TYPE: RNA
<213> ORGANISM: Artificial
<220> FEATURE:
<223> OTHER INFORMATION: consensus sequence

<400> SEQUENCE: 101
ugaaaaaauc u                                                    11

<210> SEQ ID NO 102
<211> LENGTH: 11
<212> TYPE: RNA
<213> ORGANISM: Artificial
<220> FEATURE:
<223> OTHER INFORMATION: consensus sequence

<400> SEQUENCE: 102
agaaugaaac u                                                    11

<210> SEQ ID NO 103
<211> LENGTH: 11
<212> TYPE: RNA
<213> ORGANISM: Artificial
<220> FEATURE:
<223> OTHER INFORMATION: consensus sequence

<400> SEQUENCE: 103
cgaacaaaac u                                                    11

<210> SEQ ID NO 104
<211> LENGTH: 11
```

```
<212> TYPE: RNA
<213> ORGANISM: Artificial
<220> FEATURE:
<223> OTHER INFORMATION: consensus sequence

<400> SEQUENCE: 104
cgaaagaaac u                                                              11

<210> SEQ ID NO 105
<211> LENGTH: 11
<212> TYPE: RNA
<213> ORGANISM: Artificial
<220> FEATURE:
<223> OTHER INFORMATION: consensus sequence

<400> SEQUENCE: 105
ugaaaggaac c                                                              11

<210> SEQ ID NO 106
<211> LENGTH: 11
<212> TYPE: RNA
<213> ORGANISM: Artificial
<220> FEATURE:
<223> OTHER INFORMATION: consensus sequence
<220> FEATURE:
<221> NAME/KEY: misc_feature
<222> LOCATION: (5)..(7)
<223> OTHER INFORMATION: n is a, c, g, or u
<220> FEATURE:
<221> NAME/KEY: misc_feature
<222> LOCATION: (9)..(9)
<223> OTHER INFORMATION: n is a, c, g, or u

<400> SEQUENCE: 106
hgaannnanc y                                                              11

<210> SEQ ID NO 107
<211> LENGTH: 11
<212> TYPE: RNA
<213> ORGANISM: Artificial
<220> FEATURE:
<223> OTHER INFORMATION: consensus sequence
<220> FEATURE:
<221> NAME/KEY: misc_feature
<222> LOCATION: (6)..(7)
<223> OTHER INFORMATION: n is a, c, g, or u
<220> FEATURE:
<221> NAME/KEY: misc_feature
<222> LOCATION: (9)..(9)
<223> OTHER INFORMATION: n is a, c, g, or u

<400> SEQUENCE: 107
ugaaannanc y                                                              11

<210> SEQ ID NO 108
<211> LENGTH: 11
<212> TYPE: RNA
<213> ORGANISM: Artificial
<220> FEATURE:
<223> OTHER INFORMATION: consensus sequence
<220> FEATURE:
<221> NAME/KEY: misc_feature
<222> LOCATION: (5)..(6)
<223> OTHER INFORMATION: n is a, c, g, or u

<400> SEQUENCE: 108
cgaannaaac y                                                              11

<210> SEQ ID NO 109
```

```
<211> LENGTH: 11
<212> TYPE: RNA
<213> ORGANISM: Artificial
<220> FEATURE:
<223> OTHER INFORMATION: consensus sequence
<220> FEATURE:
<221> NAME/KEY: misc_feature
<222> LOCATION: (5)..(6)
<223> OTHER INFORMATION: n is a, c, g, or u

<400> SEQUENCE: 109
agaannaaac y                                                               11

<210> SEQ ID NO 110
<211> LENGTH: 11
<212> TYPE: RNA
<213> ORGANISM: Artificial
<220> FEATURE:
<223> OTHER INFORMATION: consensus sequence

<400> SEQUENCE: 110
ugaaaaaaac y                                                               11

<210> SEQ ID NO 111
<211> LENGTH: 11
<212> TYPE: RNA
<213> ORGANISM: Artificial
<220> FEATURE:
<223> OTHER INFORMATION: consensus sequence

<400> SEQUENCE: 111
ugaaagaaac y                                                               11

<210> SEQ ID NO 112
<211> LENGTH: 11
<212> TYPE: RNA
<213> ORGANISM: Artificial
<220> FEATURE:
<223> OTHER INFORMATION: consensus sequence

<400> SEQUENCE: 112
cgaacaaaac y                                                               11

<210> SEQ ID NO 113
<211> LENGTH: 11
<212> TYPE: RNA
<213> ORGANISM: Artificial
<220> FEATURE:
<223> OTHER INFORMATION: consensus sequence

<400> SEQUENCE: 113
cgaaagaaac y                                                               11

<210> SEQ ID NO 114
<211> LENGTH: 79
<212> TYPE: DNA
<213> ORGANISM: Artificial
<220> FEATURE:
<223> OTHER INFORMATION: template DNA
<220> FEATURE:
<221> NAME/KEY: misc_feature
<222> LOCATION: (21)..(60)
<223> OTHER INFORMATION: n is a, c, g, or t

<400> SEQUENCE: 114
ccagttgttg gtgacaatgc nnnnnnnnnn nnnnnnnnnn nnnnnnnnnn nnnnnnnnnn    60
gcagctccac aggcttccc                                                       79
```

<210> SEQ ID NO 115
<211> LENGTH: 36
<212> TYPE: DNA
<213> ORGANISM: Artificial
<220> FEATURE:
<223> OTHER INFORMATION: primer

<400> SEQUENCE: 115
taatacgact cactataggg aagcctgtgg agctgc                    36

<210> SEQ ID NO 116
<211> LENGTH: 20
<212> TYPE: DNA
<213> ORGANISM: Artificial
<220> FEATURE:
<223> OTHER INFORMATION: primer

<400> SEQUENCE: 116
ccagttgttg gtgacaatgc                                       20

<210> SEQ ID NO 117
<211> LENGTH: 74
<212> TYPE: DNA
<213> ORGANISM: Artificial
<220> FEATURE:
<223> OTHER INFORMATION: template DNA
<220> FEATURE:
<221> NAME/KEY: misc_feature
<222> LOCATION: (25)..(54)
<223> OTHER INFORMATION: n is a, c, g, or t

<400> SEQUENCE: 117
tgaggatcca tgtatgcgca catannnnnn nnnnnnnnnn nnnnnnnnnn nnnncttctg    60
gtcgaagttc tccc                                            74

<210> SEQ ID NO 118
<211> LENGTH: 45
<212> TYPE: DNA
<213> ORGANISM: Artificial
<220> FEATURE:
<223> OTHER INFORMATION: primer

<400> SEQUENCE: 118
cggaattcta atacgactca ctatagggag aacttcgacc agaag           45

<210> SEQ ID NO 119
<211> LENGTH: 24
<212> TYPE: DNA
<213> ORGANISM: Artificial
<220> FEATURE:
<223> OTHER INFORMATION: primer

<400> SEQUENCE: 119
tgaggatcca tgtatgcgca cata                                  24

<210> SEQ ID NO 120
<211> LENGTH: 82
<212> TYPE: DNA
<213> ORGANISM: Artificial
<220> FEATURE:
<223> OTHER INFORMATION: template DNA
<220> FEATURE:
<221> NAME/KEY: misc_feature
<222> LOCATION: (23)..(62)
<223> OTHER INFORMATION: n is a, c, g, or t

<400> SEQUENCE: 120
tcctaatgtc tcttctcttc acnnnnnnnn nnnnnnnnnn nnnnnnnnnn nnnnnnnnnn    60
nngccctatt cttgcctctc cc    82

<210> SEQ ID NO 121
<211> LENGTH: 37
<212> TYPE: DNA
<213> ORGANISM: Artificial
<220> FEATURE:
<223> OTHER INFORMATION: primer

<400> SEQUENCE: 121
taatacgact cactataggg agaggcaaga atagggc    37

<210> SEQ ID NO 122
<211> LENGTH: 22
<212> TYPE: DNA
<213> ORGANISM: Artificial
<220> FEATURE:
<223> OTHER INFORMATION: primer

<400> SEQUENCE: 122
tcctaatgtc tcttctcttc ac    22

<210> SEQ ID NO 123
<211> LENGTH: 75
<212> TYPE: DNA
<213> ORGANISM: Artificial
<220> FEATURE:
<223> OTHER INFORMATION: template DNA

<400> SEQUENCE: 123
gaggatccat gtatgcgcac atagggtttt tttcatcctg cagctccaca ggcttcccct    60
tctggtcgaa gttct    75

<210> SEQ ID NO 124
<211> LENGTH: 45
<212> TYPE: DNA
<213> ORGANISM: Artificial
<220> FEATURE:
<223> OTHER INFORMATION: primer

<400> SEQUENCE: 124
cggaattcta atacgactca ctataggggag aacttcgacc agaag    45

<210> SEQ ID NO 125
<211> LENGTH: 23
<212> TYPE: DNA
<213> ORGANISM: Artificial
<220> FEATURE:
<223> OTHER INFORMATION: primer

<400> SEQUENCE: 125
gaggatccat gtatgcgcac ata    23

<210> SEQ ID NO 126
<211> LENGTH: 71
<212> TYPE: DNA
<213> ORGANISM: Artificial
<220> FEATURE:
<223> OTHER INFORMATION: template DNA
<220> FEATURE:
<221> NAME/KEY: misc_feature
<222> LOCATION: (16)..(55)
<223> OTHER INFORMATION: n is a, c, g, or t

```
<400> SEQUENCE: 126
gggatcgaca gggctnnnnn nnnnnnnnnn nnnnnnnnnn nnnnnnnnnn nnnnnccgag     60
tcgtgccatc t                                                          71

<210> SEQ ID NO 127
<211> LENGTH: 15
<212> TYPE: DNA
<213> ORGANISM: Artificial
<220> FEATURE:
<223> OTHER INFORMATION: primer

<400> SEQUENCE: 127
gggatcgaca gggct                                                      15

<210> SEQ ID NO 128
<211> LENGTH: 16
<212> TYPE: DNA
<213> ORGANISM: Artificial
<220> FEATURE:
<223> OTHER INFORMATION: primer

<400> SEQUENCE: 128
agatggcacg actcgg                                                     16
```